United States Patent
Graetzel et al.

(10) Patent No.: US 12,390,286 B2
(45) Date of Patent: Aug. 19, 2025

(54) INSTRUMENT SHAPE DETERMINATION

(71) Applicant: Auris Health, Inc., Santa Clara, CA (US)

(72) Inventors: Chauncey F. Graetzel, Palo Alto, CA (US); David Paul Noonan, San Francisco, CA (US)

(73) Assignee: Auris Health, Inc., Santa Clara, CA (US)

( * ) Notice: Subject to any disclaimer, the term of this patent is extended or adjusted under 35 U.S.C. 154(b) by 135 days.

(21) Appl. No.: 18/469,140

(22) Filed: Sep. 18, 2023

(65) Prior Publication Data

US 2024/0000520 A1      Jan. 4, 2024

Related U.S. Application Data

(63) Continuation of application No. 17/124,151, filed on Dec. 16, 2020, now Pat. No. 11,779,400, which is a (Continued)

(51) Int. Cl.
     *A61B 34/20*      (2016.01)
     *A61B 34/30*      (2016.01)
     *A61B 90/00*      (2016.01)

(52) U.S. Cl.
     CPC ...... *A61B 34/20* (2016.02); *A61B 2034/2051* (2016.02); *A61B 2034/2061* (2016.02); (Continued)

(58) Field of Classification Search
     CPC ............ A61B 34/20; A61B 2034/2051; A61B 2090/0809; A61B 2034/2065; (Continued)

(56) References Cited

U.S. PATENT DOCUMENTS

| | | | |
|---|---|---|---|
| 3,572,325 A | 3/1971 | Bazell et al. | |
| 3,913,565 A | 10/1975 | Kawahara | |

(Continued)

FOREIGN PATENT DOCUMENTS

| | | | |
|---|---|---|---|
| CN | 1846181 A | 10/2006 | |
| CN | 1857877 A | 11/2006 | |

(Continued)

OTHER PUBLICATIONS

CN Office Action for Appl. No. 201980066136.3, dated Feb. 2, 2024, 6 pages.

(Continued)

*Primary Examiner* — Jason Holloway
(74) *Attorney, Agent, or Firm* — Paradice & Li LLP

(57) ABSTRACT

A method of controlling an instrument involves measuring strain of one or more optical fibers associated with an elongate shaft of an instrument, determining a first shape estimation of the elongate shaft based on the measured strain, determining, based on the measured strain, a strain-indicated characteristic of the elongate shaft with respect to a mechanical condition of the elongate shaft, determining an expected range of the mechanical condition of the elongate shaft, determining that the strain-indicated characteristic is outside of the expected range of the mechanical condition, and in response to the determination that the strain-indicated characteristic is outside of the expected range, determining a second shape estimation of the elongate shaft, the second shape estimation being based to a lesser degree on the measured strain compared to the first shape estimation.

20 Claims, 27 Drawing Sheets

Related U.S. Application Data continuation of application No. 16/531,580, filed on Aug. 5, 2019, now Pat. No. 10,898,276.

(60) Provisional application No. 62/715,668, filed on Aug. 7, 2018.

(52) U.S. Cl.
CPC . *A61B 2034/2065* (2016.02); *A61B 2034/301* (2016.02); *A61B 2090/0809* (2016.02); *A61B 2090/0818* (2016.02); *A61B 2090/3782* (2016.02)

(58) Field of Classification Search
CPC ...... A61B 2034/301; A61B 2034/2061; A61B 2034/2072; A61B 2017/00809; A61B 2090/3735; A61B 2090/3614; A61B 2034/105; A61B 2034/2048; A61B 2034/107; A61B 2090/3782; A61B 2090/0818
See application file for complete search history.

(56) References Cited

U.S. PATENT DOCUMENTS

| | | |
|---|---|---|
| 4,294,234 A | 10/1981 | Matsuo |
| 4,392,485 A | 7/1983 | Hiltebrandt |
| 4,607,619 A | 8/1986 | Seike et al. |
| 4,690,175 A | 9/1987 | Ouchi et al. |
| 4,706,656 A | 11/1987 | Kuboto |
| 4,741,326 A | 5/1988 | Sidall et al. |
| 4,745,908 A | 5/1988 | Wardle |
| 4,748,969 A | 6/1988 | Wardle |
| 4,750,475 A | 6/1988 | Yoshihashi |
| 4,771,766 A | 9/1988 | Aoshiro et al. |
| 4,846,791 A | 7/1989 | Hattler et al. |
| 4,869,238 A | 9/1989 | Opie et al. |
| 4,906,496 A | 3/1990 | Hosono et al. |
| 4,907,168 A | 3/1990 | Boggs |
| 4,967,732 A | 11/1990 | Inoue |
| 5,050,585 A | 9/1991 | Takahashi |
| 5,083,549 A | 1/1992 | Cho et al. |
| 5,106,387 A | 4/1992 | Kittrell et al. |
| 5,108,800 A | 4/1992 | Koo |
| 5,125,909 A | 6/1992 | Heimberger |
| 5,168,864 A | 12/1992 | Shockey |
| 5,217,002 A | 6/1993 | Katsurada et al. |
| 5,251,611 A | 10/1993 | Zehel et al. |
| 5,257,617 A | 11/1993 | Takahashi |
| 5,261,391 A | 11/1993 | Inoue |
| 5,287,861 A | 2/1994 | Wilk |
| 5,313,934 A | 5/1994 | Wiita et al. |
| 5,386,818 A | 2/1995 | Schneebaum et al. |
| 5,448,988 A | 9/1995 | Watanabe |
| 5,478,330 A | 12/1995 | Imran et al. |
| 5,482,029 A | 1/1996 | Sekiguchi et al. |
| 5,489,270 A | 2/1996 | Erp |
| 5,507,725 A | 4/1996 | Savage et al. |
| 5,533,985 A | 7/1996 | Wang |
| 5,580,200 A | 12/1996 | Fullerton |
| 5,681,296 A | 10/1997 | Ishida |
| 5,704,534 A | 1/1998 | Huitema et al. |
| 5,720,775 A | 2/1998 | Larnard |
| 5,741,429 A | 4/1998 | Donadio, III et al. |
| 5,749,889 A | 5/1998 | Bacich et al. |
| 5,873,817 A | 2/1999 | Kokish et al. |
| 5,876,325 A | 3/1999 | Mizuno et al. |
| 5,879,287 A | 3/1999 | Yoshihashi |
| 5,882,347 A | 3/1999 | Mouris-Laan et al. |
| 5,888,191 A | 3/1999 | Akiba et al. |
| 5,910,129 A | 6/1999 | Koblish et al. |
| 5,938,586 A | 8/1999 | Wilk et al. |
| 5,938,587 A | 8/1999 | Taylor et al. |
| 6,012,494 A | 1/2000 | Balazs |
| 6,143,013 A | 11/2000 | Samson et al. |
| 6,157,853 A | 12/2000 | Blume et al. |
| 6,174,280 B1 | 1/2001 | Oneda et al. |
| 6,197,015 B1 | 3/2001 | Wilson |
| 6,198,974 B1 | 3/2001 | Webster, Jr. |
| 6,234,958 B1 | 5/2001 | Snoke et al. |
| 6,315,715 B1 | 11/2001 | Taylor et al. |
| 6,389,187 B1 | 5/2002 | Greenaway et al. |
| 6,404,497 B1 | 6/2002 | Backman et al. |
| 6,436,107 B1 | 8/2002 | Wang et al. |
| 6,464,632 B1 | 10/2002 | Taylor |
| 6,485,411 B1 | 11/2002 | Konstorum et al. |
| 6,491,626 B1 | 12/2002 | Stone et al. |
| 6,537,205 B1 | 3/2003 | Smith |
| 6,545,760 B1 | 4/2003 | Froggatt et al. |
| 6,554,793 B1 | 4/2003 | Pauker et al. |
| 6,716,178 B1 | 4/2004 | Kilpatrick et al. |
| 6,746,422 B1 | 6/2004 | Noriega et al. |
| 6,749,560 B1 | 6/2004 | Konstorum et al. |
| 6,790,173 B2 | 9/2004 | Saadat et al. |
| 6,827,710 B1 | 12/2004 | Mooney et al. |
| 6,827,712 B2 | 12/2004 | Tovey et al. |
| 6,837,846 B2 | 1/2005 | Jaffe et al. |
| 6,908,428 B2 | 6/2005 | Aizenfeld et al. |
| 6,921,362 B2 | 7/2005 | Ouchi |
| 6,958,035 B2 | 10/2005 | Friedman et al. |
| 7,008,401 B2 | 3/2006 | Thompson et al. |
| 7,130,700 B2 | 10/2006 | Gardeski et al. |
| 7,594,903 B2 | 9/2009 | Webler et al. |
| 7,645,230 B2 | 1/2010 | Mikkaichi et al. |
| 7,645,231 B2 | 1/2010 | Akiba |
| 7,781,724 B2 | 8/2010 | Childers et al. |
| 7,789,827 B2 | 9/2010 | Landry |
| 7,930,065 B2 | 4/2011 | Larkin et al. |
| 8,046,049 B2 | 10/2011 | Govari et al. |
| 8,052,636 B2 | 11/2011 | Moll et al. |
| 8,246,536 B2 | 8/2012 | Ochi et al. |
| 8,444,637 B2 | 5/2013 | Podmore et al. |
| 8,460,236 B2 | 6/2013 | Roelle et al. |
| 8,498,691 B2 | 7/2013 | Moll et al. |
| 8,515,215 B2 | 8/2013 | Younge et al. |
| 8,652,030 B2 | 2/2014 | Matsuura et al. |
| 8,686,747 B2 | 4/2014 | Berner et al. |
| 8,758,231 B2 | 6/2014 | Bunch et al. |
| 8,827,947 B2 | 9/2014 | Bosman et al. |
| 9,186,046 B2 | 11/2015 | Ramamurthy et al. |
| 9,314,953 B2 | 4/2016 | Lauer et al. |
| 9,427,551 B2 | 8/2016 | Leeflang et al. |
| 9,504,604 B2 | 11/2016 | Alvarez |
| 9,561,083 B2 | 2/2017 | Yu et al. |
| 9,591,990 B2 | 3/2017 | Chen et al. |
| 9,622,827 B2 | 4/2017 | Yu et al. |
| 9,636,184 B2 | 5/2017 | Lee et al. |
| 9,713,509 B2 | 7/2017 | Schuh et al. |
| 9,726,476 B2 | 8/2017 | Ramamurthy et al. |
| 9,727,963 B2 | 8/2017 | Mintz et al. |
| 9,737,371 B2 | 8/2017 | Romo et al. |
| 9,737,373 B2 | 8/2017 | Schuh |
| 9,744,335 B2 | 8/2017 | Jiang |
| 9,763,741 B2 | 9/2017 | Alvarez et al. |
| 9,788,910 B2 | 10/2017 | Schuh |
| 9,844,353 B2 | 12/2017 | Walker et al. |
| 9,844,412 B2 | 12/2017 | Bogusky et al. |
| 9,867,635 B2 | 1/2018 | Alvarez et al. |
| 9,918,659 B2 | 3/2018 | Chopra et al. |
| 9,918,681 B2 | 3/2018 | Wallace et al. |
| 9,931,025 B1 | 4/2018 | Graetzel et al. |
| 9,949,749 B2 | 4/2018 | Noonan et al. |
| 9,955,986 B2 | 5/2018 | Shah |
| 9,962,228 B2 | 5/2018 | Schuh et al. |
| 9,980,785 B2 | 5/2018 | Schuh |
| 9,993,313 B2 | 6/2018 | Schuh et al. |
| 10,016,900 B1 | 7/2018 | Meyer et al. |
| 10,022,192 B1 | 7/2018 | Ummalaneni |
| 10,080,576 B2 | 9/2018 | Romo et al. |
| 10,130,427 B2 | 11/2018 | Tanner et al. |
| 10,136,959 B2 | 11/2018 | Mintz et al. |
| 10,145,747 B1 | 12/2018 | Lin et al. |
| 10,149,720 B2 | 12/2018 | Romo |

(56) References Cited

U.S. PATENT DOCUMENTS

| | | |
|---|---|---|
| 10,159,532 B1 | 12/2018 | Ummalaneni |
| 10,159,533 B2 | 12/2018 | Moll et al. |
| 10,169,875 B2 | 1/2019 | Mintz et al. |
| 10,219,874 B2 | 3/2019 | Yu et al. |
| 10,231,793 B2 | 3/2019 | Romo |
| 10,231,867 B2 | 3/2019 | Alvarez et al. |
| 10,244,926 B2 | 4/2019 | Noonan et al. |
| 10,271,915 B2 | 4/2019 | Diolaiti et al. |
| 10,285,574 B2 | 5/2019 | Landey et al. |
| 10,299,870 B2 | 5/2019 | Connolly et al. |
| 10,314,463 B2 | 6/2019 | Agrawal et al. |
| 10,363,103 B2 | 7/2019 | Alvarez et al. |
| 10,376,672 B2 | 8/2019 | Yu |
| 10,383,765 B2 | 8/2019 | Alvarez et al. |
| 10,398,518 B2 | 9/2019 | Yu et al. |
| 10,405,908 B2 | 9/2019 | Redmond |
| 10,405,939 B2 | 9/2019 | Romo |
| 10,405,940 B2 | 9/2019 | Romo |
| 10,426,559 B2 | 10/2019 | Graetzel et al. |
| 10,426,661 B2 | 10/2019 | Kintz |
| 10,434,660 B2 | 10/2019 | Meyer et al. |
| 10,463,439 B2 | 11/2019 | Joseph et al. |
| 10,464,209 B2 | 11/2019 | Ho et al. |
| 10,470,830 B2 | 11/2019 | Hill et al. |
| 10,482,599 B2 | 11/2019 | Mintz et al. |
| 10,493,241 B2 | 12/2019 | Jiang |
| 10,500,001 B2 | 12/2019 | Yu et al. |
| 10,517,692 B2 | 12/2019 | Eyre et al. |
| 10,524,866 B2 | 1/2020 | Srinivasan et al. |
| 10,539,478 B2 | 1/2020 | Lin et al. |
| 10,543,048 B2 | 1/2020 | Noonan |
| 10,555,778 B2 | 2/2020 | Ummalaneni |
| 10,555,780 B2 | 2/2020 | Tanner et al. |
| 10,631,949 B2 | 4/2020 | Schuh et al. |
| 10,639,108 B2 | 5/2020 | Romo et al. |
| 10,639,109 B2 | 5/2020 | Bovay et al. |
| 10,639,114 B2 | 5/2020 | Schuh et al. |
| 10,667,720 B2 | 6/2020 | Wong et al. |
| 10,667,871 B2 | 6/2020 | Romo et al. |
| 10,667,875 B2 | 6/2020 | DeFonzo et al. |
| 10,682,189 B2 | 6/2020 | Schuh et al. |
| 10,702,348 B2 | 7/2020 | Moll et al. |
| 10,716,461 B2 | 7/2020 | Jenkins |
| 10,743,751 B2 | 8/2020 | Landey et al. |
| 10,744,035 B2 | 8/2020 | Alvarez et al. |
| 10,751,140 B2 | 8/2020 | Wallace et al. |
| 10,765,303 B2 | 9/2020 | Graetzel et al. |
| 10,765,487 B2 | 9/2020 | Ho et al. |
| 10,779,898 B2 | 9/2020 | Hill et al. |
| 10,786,329 B2 | 9/2020 | Schuh et al. |
| 10,786,432 B2 | 9/2020 | Jornitz et al. |
| 10,792,464 B2 | 10/2020 | Romo et al. |
| 10,792,466 B2 | 10/2020 | Landey et al. |
| 10,813,539 B2 | 10/2020 | Graetzel et al. |
| 10,814,101 B2 | 10/2020 | Jiang |
| 10,820,947 B2 | 11/2020 | Julian |
| 10,820,954 B2 | 11/2020 | Marsot et al. |
| 10,827,913 B2 | 11/2020 | Ummalaneni et al. |
| 10,828,118 B2 | 11/2020 | Schuh et al. |
| 10,835,153 B2 | 11/2020 | Rafii-Tari et al. |
| 10,850,013 B2 | 12/2020 | Hsu et al. |
| 10,881,280 B2 | 1/2021 | Baez, Jr. |
| 2001/0004676 A1 | 6/2001 | Ouchi |
| 2003/0036748 A1 | 2/2003 | Cooper et al. |
| 2003/0130564 A1 | 7/2003 | Martone et al. |
| 2003/0158545 A1 | 8/2003 | Hovda et al. |
| 2003/0163199 A1 | 8/2003 | Boehm et al. |
| 2003/0195664 A1 | 10/2003 | Nowlin et al. |
| 2004/0015122 A1 | 1/2004 | Zhang et al. |
| 2004/0054322 A1 | 3/2004 | Vargas |
| 2004/0072066 A1 | 4/2004 | Cho et al. |
| 2004/0138525 A1 | 7/2004 | Saadat et al. |
| 2004/0193013 A1 | 9/2004 | Iwasaka et al. |
| 2004/0249246 A1 | 12/2004 | Campos |
| 2004/0257021 A1 | 12/2004 | Chang et al. |
| 2005/0004515 A1 | 1/2005 | Hart et al. |
| 2005/0025005 A1 | 2/2005 | Hwang et al. |
| 2005/0125005 A1 | 6/2005 | Fujikura |
| 2005/0131279 A1 | 6/2005 | Boulais et al. |
| 2005/0154262 A1 | 7/2005 | Banik et al. |
| 2005/0159646 A1 | 7/2005 | Nordstrom et al. |
| 2005/0165366 A1 | 7/2005 | Brustad et al. |
| 2005/0222581 A1 | 10/2005 | Fischer et al. |
| 2005/0234293 A1 | 10/2005 | Yamamoto et al. |
| 2005/0256452 A1 | 11/2005 | DeMarchi et al. |
| 2005/0272975 A1 | 12/2005 | McWeeney et al. |
| 2005/0273085 A1 | 12/2005 | Hinman et al. |
| 2005/0288549 A1 | 12/2005 | Mathis |
| 2006/0013523 A1 | 1/2006 | Childers et al. |
| 2006/0041188 A1 | 2/2006 | Dirusso et al. |
| 2006/0111692 A1 | 5/2006 | Hlavka et al. |
| 2006/0241368 A1 | 10/2006 | Fichtinger et al. |
| 2006/0264708 A1 | 11/2006 | Horne |
| 2006/0276827 A1 | 12/2006 | Mitelberg et al. |
| 2006/0287769 A1 | 12/2006 | Yanagita et al. |
| 2007/0060879 A1 | 3/2007 | Weitzner et al. |
| 2007/0112355 A1 | 5/2007 | Salahieh et al. |
| 2007/0135733 A1 | 6/2007 | Soukup et al. |
| 2007/0135763 A1 | 6/2007 | Musbach et al. |
| 2007/0135803 A1 | 6/2007 | Belson |
| 2007/0156019 A1 | 7/2007 | Larkin et al. |
| 2007/0270645 A1 | 11/2007 | Ikeda |
| 2007/0270679 A1 | 11/2007 | Nguyen et al. |
| 2007/0282167 A1 | 12/2007 | Barenboym et al. |
| 2007/0287886 A1 | 12/2007 | Saadat |
| 2008/0008869 A1 | 1/2008 | Good et al. |
| 2008/0039255 A1 | 2/2008 | Jinno et al. |
| 2008/0051629 A1 | 2/2008 | Sugiyama et al. |
| 2008/0065103 A1 | 3/2008 | Cooper et al. |
| 2008/0097293 A1 | 4/2008 | Chin et al. |
| 2008/0108869 A1 | 5/2008 | Sanders et al. |
| 2008/0139887 A1 | 6/2008 | Fitzpatrick |
| 2008/0146874 A1 | 6/2008 | Chen |
| 2008/0147089 A1 | 6/2008 | Loh et al. |
| 2008/0177285 A1 | 7/2008 | Brock et al. |
| 2008/0208001 A1 | 8/2008 | Hadani |
| 2008/0212082 A1 | 9/2008 | Froggatt et al. |
| 2008/0218770 A1 | 9/2008 | Moll et al. |
| 2008/0285909 A1 | 11/2008 | Younge et al. |
| 2009/0099420 A1 | 4/2009 | Woodley et al. |
| 2009/0163851 A1 | 6/2009 | Holloway et al. |
| 2009/0247880 A1 | 10/2009 | Naruse et al. |
| 2009/0254083 A1 | 10/2009 | Wallace et al. |
| 2009/0262109 A1 | 10/2009 | Markowitz et al. |
| 2009/0299344 A1 | 12/2009 | Lee et al. |
| 2009/0306587 A1 | 12/2009 | Milijasevic et al. |
| 2010/0030023 A1 | 2/2010 | Yoshie |
| 2010/0073150 A1 | 3/2010 | Olson et al. |
| 2010/0114115 A1 | 5/2010 | Schlesinger et al. |
| 2010/0130823 A1 | 5/2010 | Ando |
| 2010/0168918 A1 | 7/2010 | Zhao et al. |
| 2010/0217184 A1 | 8/2010 | Koblish et al. |
| 2010/0234831 A1 | 9/2010 | Hinman et al. |
| 2010/0249497 A1 | 9/2010 | Peine et al. |
| 2010/0249506 A1 | 9/2010 | Prisco et al. |
| 2011/0009863 A1 | 1/2011 | Marczyk et al. |
| 2011/0046441 A1 | 2/2011 | Wiltshire et al. |
| 2011/0077681 A1 | 3/2011 | Nagano et al. |
| 2011/0098533 A1 | 4/2011 | Onoda et al. |
| 2011/0130718 A1 | 6/2011 | Kidd et al. |
| 2011/0148442 A1 | 6/2011 | Berner et al. |
| 2011/0152880 A1 | 6/2011 | Alvarez et al. |
| 2011/0196199 A1 | 8/2011 | Donhowe et al. |
| 2011/0245844 A1 | 10/2011 | Jinno |
| 2011/0261183 A1 | 10/2011 | Ma et al. |
| 2011/0270084 A1 | 11/2011 | Choi et al. |
| 2011/0306836 A1 | 12/2011 | Ohline et al. |
| 2011/0319714 A1 | 12/2011 | Roelle et al. |
| 2012/0071821 A1 | 3/2012 | Yu |
| 2012/0071894 A1 | 3/2012 | Tanner et al. |
| 2012/0071895 A1 | 3/2012 | Stahler et al. |
| 2012/0123327 A1 | 5/2012 | Miller |
| 2012/0136372 A1 | 5/2012 | Girbau et al. |
| 2012/0136419 A1 | 5/2012 | Zarembo et al. |

(56) References Cited

U.S. PATENT DOCUMENTS

| | | |
|---|---|---|
| 2012/0143226 A1 | 6/2012 | Belson et al. |
| 2012/0190976 A1 | 7/2012 | Kleinstreuer |
| 2012/0191107 A1 | 7/2012 | Tanner et al. |
| 2012/0197097 A1 | 8/2012 | Chan et al. |
| 2012/0239012 A1 | 9/2012 | Laurent et al. |
| 2012/0259244 A1 | 10/2012 | Roberts et al. |
| 2012/0283747 A1 | 11/2012 | Popovic |
| 2012/0289777 A1 | 11/2012 | Chopra et al. |
| 2013/0018400 A1 | 1/2013 | Milton et al. |
| 2013/0030519 A1 | 1/2013 | Tran et al. |
| 2013/0035537 A1 | 2/2013 | Wallace et al. |
| 2013/0090552 A1 | 4/2013 | Ramamurthy et al. |
| 2013/0109957 A1 | 5/2013 | Hooft et al. |
| 2013/0144116 A1 | 6/2013 | Cooper et al. |
| 2013/0165854 A1 | 6/2013 | Sandhu et al. |
| 2013/0165908 A1 | 6/2013 | Purdy et al. |
| 2013/0204124 A1 | 8/2013 | Duindam et al. |
| 2013/0226151 A1 | 8/2013 | Suehara |
| 2013/0303892 A1 | 11/2013 | Zhao et al. |
| 2013/0304091 A1 | 11/2013 | Straehnz et al. |
| 2013/0317276 A1 | 11/2013 | D'Andrea |
| 2013/0317519 A1 | 11/2013 | Romo et al. |
| 2013/0345519 A1 | 12/2013 | Piskun et al. |
| 2013/0345719 A1 | 12/2013 | Donhowe et al. |
| 2014/0012288 A1 | 1/2014 | Darisse et al. |
| 2014/0046313 A1 | 2/2014 | Pederson et al. |
| 2014/0142591 A1 | 5/2014 | Alvarez et al. |
| 2014/0187949 A1 | 7/2014 | Zhao et al. |
| 2014/0200402 A1 | 7/2014 | Snoke et al. |
| 2014/0235943 A1 | 8/2014 | Paris et al. |
| 2014/0276594 A1 | 9/2014 | Tanner et al. |
| 2014/0316397 A1 | 10/2014 | Brown |
| 2014/0343416 A1 | 11/2014 | Panescu et al. |
| 2014/0357984 A1 | 12/2014 | Wallace et al. |
| 2014/0364870 A1 | 12/2014 | Alvarez et al. |
| 2014/0379000 A1 | 12/2014 | Romo et al. |
| 2015/0031950 A1 | 1/2015 | Drontle et al. |
| 2015/0255782 A1 | 9/2015 | Kim et al. |
| 2016/0000414 A1 | 1/2016 | Brown et al. |
| 2016/0001038 A1 | 1/2016 | Romo et al. |
| 2016/0007881 A1 | 1/2016 | Wong et al. |
| 2016/0067450 A1 | 3/2016 | Kowshik |
| 2016/0183841 A1 | 6/2016 | Duindam et al. |
| 2016/0227982 A1 | 8/2016 | Takahashi et al. |
| 2016/0270865 A1 | 9/2016 | Landey et al. |
| 2016/0287279 A1 | 10/2016 | Bovay et al. |
| 2016/0287346 A1 | 10/2016 | Hyodo et al. |
| 2016/0346049 A1 | 12/2016 | Allen et al. |
| 2016/0349044 A1 | 12/2016 | Marell et al. |
| 2016/0372743 A1 | 12/2016 | Cho et al. |
| 2016/0374590 A1 | 12/2016 | Wong et al. |
| 2017/0007337 A1 | 1/2017 | Dan |
| 2017/0010084 A1 | 1/2017 | Falchieri et al. |
| 2017/0100084 A1 | 4/2017 | Walker et al. |
| 2017/0119481 A1 | 5/2017 | Romo et al. |
| 2017/0151027 A1 | 6/2017 | Walker et al. |
| 2017/0165011 A1 | 6/2017 | Bovay et al. |
| 2017/0172673 A1 | 6/2017 | Yu et al. |
| 2017/0202627 A1 | 7/2017 | Sramek et al. |
| 2017/0209073 A1 | 7/2017 | Sramek et al. |
| 2017/0281218 A1 | 10/2017 | Timm |
| 2017/0290631 A1 | 10/2017 | Lee et al. |
| 2017/0333679 A1 | 11/2017 | Jiang |
| 2017/0340396 A1 | 11/2017 | Romo et al. |
| 2017/0367782 A1 | 12/2017 | Schuh et al. |
| 2018/0025666 A1 | 1/2018 | Ho et al. |
| 2018/0055589 A1 | 3/2018 | Joseph et al. |
| 2018/0177556 A1 | 6/2018 | Noonan |
| 2018/0214011 A1 | 8/2018 | Graetzel et al. |
| 2018/0221038 A1 | 8/2018 | Noonan et al. |
| 2018/0221039 A1 | 8/2018 | Shah |
| 2018/0250083 A1 | 9/2018 | Schuh et al. |
| 2018/0271616 A1 | 9/2018 | Schuh et al. |
| 2018/0279852 A1 | 10/2018 | Rafii-Tari et al. |
| 2018/0280660 A1 | 10/2018 | Landey et al. |
| 2018/0289431 A1 | 10/2018 | Draper et al. |
| 2018/0325499 A1 | 11/2018 | Landey et al. |
| 2018/0333044 A1 | 11/2018 | Jenkins |
| 2018/0360435 A1 | 12/2018 | Romo |
| 2019/0000559 A1 | 1/2019 | Berman et al. |
| 2019/0000560 A1 | 1/2019 | Berman et al. |
| 2019/0000576 A1 | 1/2019 | Mintz et al. |
| 2019/0083183 A1 | 3/2019 | Moll et al. |
| 2019/0105110 A1 | 4/2019 | Tanner et al. |
| 2019/0105776 A1 | 4/2019 | Ho et al. |
| 2019/0107454 A1 | 4/2019 | Lin et al. |
| 2019/0110839 A1 | 4/2019 | Rafii-Tari et al. |
| 2019/0110843 A1 | 4/2019 | Ummalaneni |
| 2019/0151148 A1 | 5/2019 | Alvarez et al. |
| 2019/0167366 A1 | 6/2019 | Ummalaneni et al. |
| 2019/0175009 A1 | 6/2019 | Mintz et al. |
| 2019/0175062 A1 | 6/2019 | Rafii-Tari et al. |
| 2019/0175287 A1 | 6/2019 | Hill et al. |
| 2019/0175799 A1 | 6/2019 | Hsu et al. |
| 2019/0183585 A1 | 6/2019 | Rafii-Tari et al. |
| 2019/0183587 A1 | 6/2019 | Rafii-Tari et al. |
| 2019/0216548 A1 | 7/2019 | Ummalaneni |
| 2019/0216550 A1 | 7/2019 | Eyre et al. |
| 2019/0216576 A1 | 7/2019 | Eyre et al. |
| 2019/0223974 A1 | 7/2019 | Romo et al. |
| 2019/0228525 A1 | 7/2019 | Mintz et al. |
| 2019/0228528 A1 | 7/2019 | Mintz et al. |
| 2019/0246882 A1 | 8/2019 | Graetzel et al. |
| 2019/0262086 A1 | 8/2019 | Connolly et al. |
| 2019/0269468 A1 | 9/2019 | Hsu et al. |
| 2019/0274764 A1 | 9/2019 | Romo |
| 2019/0290109 A1 | 9/2019 | Agrawal et al. |
| 2019/0298160 A1 | 10/2019 | Ummalaneni et al. |
| 2019/0298458 A1 | 10/2019 | Srinivasan et al. |
| 2019/0298460 A1 | 10/2019 | Al-Jadda et al. |
| 2019/0298465 A1 | 10/2019 | Chin et al. |
| 2019/0307987 A1 | 10/2019 | Yu |
| 2019/0328213 A1 | 10/2019 | Landey et al. |
| 2019/0336238 A1 | 11/2019 | Yu et al. |
| 2019/0365201 A1 | 12/2019 | Noonan et al. |
| 2019/0365209 A1 | 12/2019 | Ye et al. |
| 2019/0365479 A1 | 12/2019 | Rafii-Tari |
| 2019/0365486 A1 | 12/2019 | Srinivasan et al. |
| 2019/0374297 A1 | 12/2019 | Wallace et al. |
| 2019/0375383 A1 | 12/2019 | Auer |
| 2019/0380787 A1 | 12/2019 | Ye et al. |
| 2019/0380797 A1 | 12/2019 | Yu et al. |
| 2020/0000530 A1 | 1/2020 | DeFonzo et al. |
| 2020/0000533 A1 | 1/2020 | Schuh et al. |
| 2020/0007894 A1 | 1/2020 | Zhao et al. |
| 2020/0022767 A1 | 1/2020 | Hill et al. |
| 2020/0038123 A1 | 2/2020 | Graetzel et al. |
| 2020/0038128 A1 | 2/2020 | Joseph et al. |
| 2020/0039086 A1 | 2/2020 | Meyer et al. |
| 2020/0046942 A1 | 2/2020 | Alvarez et al. |
| 2020/0054408 A1 | 2/2020 | Schuh et al. |
| 2020/0060516 A1 | 2/2020 | Baez, Jr. |
| 2020/0085516 A1 | 3/2020 | DeFonzo et al. |
| 2020/0093549 A1 | 3/2020 | Chin et al. |
| 2020/0093554 A1 | 3/2020 | Schuh et al. |
| 2020/0100845 A1 | 4/2020 | Julian |
| 2020/0100853 A1 | 4/2020 | Ho et al. |
| 2020/0100855 A1 | 4/2020 | Leparmentier et al. |
| 2020/0101264 A1 | 4/2020 | Jiang |
| 2020/0107894 A1 | 4/2020 | Wallace et al. |
| 2020/0121502 A1 | 4/2020 | Kintz |
| 2020/0146769 A1 | 5/2020 | Eyre et al. |
| 2020/0170720 A1 | 6/2020 | Ummalaneni |
| 2020/0171660 A1 | 6/2020 | Ho et al. |
| 2020/0188043 A1 | 6/2020 | Yu et al. |
| 2020/0197112 A1 | 6/2020 | Chin et al. |
| 2020/0206472 A1 | 7/2020 | Ma et al. |
| 2020/0217733 A1 | 7/2020 | Lin et al. |
| 2020/0222134 A1 | 7/2020 | Schuh et al. |
| 2020/0237458 A1 | 7/2020 | DeFonzo et al. |
| 2020/0261172 A1 | 8/2020 | Romo et al. |
| 2020/0268459 A1 | 8/2020 | Noonan |
| 2020/0268460 A1 | 8/2020 | Tse et al. |
| 2020/0281787 A1 | 9/2020 | Ruiz |

(56) References Cited

U.S. PATENT DOCUMENTS

| | | |
|---|---|---|
| 2020/0297437 A1 | 9/2020 | Schuh et al. |
| 2020/0297444 A1 | 9/2020 | Camarillo et al. |
| 2020/0305983 A1 | 10/2020 | Yampolsky et al. |
| 2020/0305989 A1 | 10/2020 | Schuh et al. |
| 2020/0305992 A1 | 10/2020 | Schuh et al. |
| 2020/0315717 A1 | 10/2020 | Bovay et al. |
| 2020/0315723 A1 | 10/2020 | Hassan et al. |
| 2020/0323596 A1 | 10/2020 | Moll et al. |
| 2020/0330167 A1 | 10/2020 | Romo et al. |
| 2020/0337593 A1 | 10/2020 | Wong et al. |
| 2020/0345216 A1 | 11/2020 | Jenkins |
| 2020/0352420 A1 | 11/2020 | Graetzel et al. |
| 2020/0360183 A1 | 11/2020 | Alvarez et al. |
| 2020/0367726 A1 | 11/2020 | Landey et al. |
| 2020/0367981 A1 | 11/2020 | Ho et al. |
| 2020/0375678 A1 | 12/2020 | Wallace et al. |
| 2020/0405317 A1 | 12/2020 | Wallace |
| 2020/0405411 A1 | 12/2020 | Draper et al. |
| 2020/0405419 A1 | 12/2020 | Mao et al. |
| 2020/0405420 A1 | 12/2020 | Purohit et al. |
| 2020/0405423 A1 | 12/2020 | Schuh |
| 2020/0405424 A1 | 12/2020 | Schuh |
| 2020/0405434 A1 | 12/2020 | Schuh et al. |
| 2020/0406002 A1 | 12/2020 | Romo et al. |

FOREIGN PATENT DOCUMENTS

| | | |
|---|---|---|
| CN | 102316817 A | 1/2012 |
| CN | 102458295 A | 5/2012 |
| CN | 102665590 A | 9/2012 |
| CN | 102711586 A | 10/2012 |
| CN | 102711587 A | 10/2012 |
| CN | 102973317 A | 3/2013 |
| CN | 103767659 A | 5/2014 |
| CN | 103930063 A | 7/2014 |
| EP | 0543539 A1 | 5/1993 |
| EP | 0776739 A2 | 6/1997 |
| EP | 0904796 A2 | 3/1999 |
| EP | 1442720 A1 | 8/2004 |
| EP | 2626029 A2 | 8/2013 |
| JP | 2006525087 A | 11/2006 |
| JP | 2007511247 A | 5/2007 |
| JP | 2010046384 A | 3/2010 |
| JP | 2011015992 A | 1/2011 |
| JP | 2011200341 A | 10/2011 |
| JP | 2012105793 A | 6/2012 |
| KR | 10-2008-0027256 A | 3/2008 |
| WO | 9414494 A2 | 7/1994 |
| WO | 0067640 A2 | 11/2000 |
| WO | 02074178 A2 | 9/2002 |
| WO | 2004039273 A2 | 5/2004 |
| WO | 2004096015 A2 | 11/2004 |
| WO | 2004103430 A2 | 12/2004 |
| WO | 2004105849 A1 | 12/2004 |
| WO | 2005032637 A2 | 4/2005 |
| WO | 2005081202 A2 | 9/2005 |
| WO | 2006099056 A2 | 9/2006 |
| WO | 2007146987 A2 | 12/2007 |
| WO | 2008097540 A2 | 8/2008 |
| WO | 2009092059 A2 | 7/2009 |
| WO | 2009097461 A1 | 8/2009 |
| WO | 2010081187 A1 | 7/2010 |
| WO | 2011005335 A1 | 1/2011 |
| WO | 2012101551 A1 | 8/2012 |
| WO | 2012131550 A1 | 10/2012 |
| WO | 2013107468 A1 | 7/2013 |
| WO | 2014001977 A2 | 1/2014 |
| WO | 2015093602 A1 | 6/2015 |
| WO | 2016003052 A1 | 1/2016 |
| WO | 2017139621 A1 | 8/2017 |
| WO | 2018057633 A1 | 3/2018 |

OTHER PUBLICATIONS

CN Search Report for Appl. No. 201980066136.3, dated Feb. 9, 2024, 3 pages.

Notification to Grant Patent Right for Invention from China Patent Application No. 201980066136.3, dated Feb. 28, 2025, 8 pages.

Second Office Action, issued on Aug. 8, 2024, in China Patent Application No. 201980066136.3, pp. 1-23.

First Office Action, issued on Aug. 30, 2024, in Korean Patent Application No. 10-2023-7041982, pp. 1-9.

European Search Report for appl. No. 19848401.6, dated Mar. 29, 2022, 9 pages.

International Search Report and Written Opinion in application No. PCT/US2019/45125, dated Oct. 24, 2019, 9 pages.

KR Final Rejection for Appl. No. 10-2021-7006777, dated Apr. 25, 2023, 3 pages.

KR Preliminary Rejection for Appl. No. 1020217006777, dated Dec. 21, 8 pages.

Non-Final Rejection for U.S. Appl. No. 16/531,580, dated Apr. 17, 2020, 13 pages.

Non-Final Rejection for U.S. Appl. No. 17/124,151, dated Dec. 7, 2022, 10 pages.

Notice of Allowance for U.S. Appl. No. 16/531,580, dated Sep. 17, 2020, 5 pages.

Notice of Allowance for U.S. Appl. No. 17/124,151 dated Aug. 3, 2023, 2 pages.

Notice of Allowance for U.S. Appl. No. 17/124,151 dated Jun. 7, 2023, 7 pages.

Office Action from European Patent Application No. 19848401.6, dated Apr. 25, 2025, 7 pages.

Office Action from Korean Patent Application No. 10-2023-7041982, dated May 26, 2025, 12 pages.

INSTRUMENT SHAPE DETERMINATION

CROSS-REFERENCE TO RELATED APPLICATION

This application is a continuation of U.S. patent application Ser. No. 17/124,151, filed Dec. 16, 2020, now U.S. Pat. No. 11,779,400, which is a continuation of U.S. patent application Ser. No. 16/531,580, filed Aug. 5, 2019, now U.S. Pat. No. 10,898,276, which claims the benefit of U.S. Provisional Application No. 62/715,668, filed Aug. 7, 2018, the complete disclosures of which are hereby incorporated by reference in their entireties.

TECHNICAL FIELD

The systems and methods disclosed herein are directed to surgical robotics, and more particularly to navigation of a medical instrument within a tubular network of a patient's body.

BACKGROUND

Bronchoscopy is a medical procedure that allows a physician to examine the inside conditions of a patient's lung airways, such as bronchi and bronchioles. The lung airways carry air from the trachea, or windpipe, to the lungs. During the medical procedure, a thin, flexible tubular tool, known as a bronchoscope, may be inserted into the patient's mouth and passed down the patient's throat into his/her lung airways, and patients are generally anesthetized in order to relax their throats and lung cavities for surgical examinations and operations during the medical procedure.

A bronchoscope can include a light source and a small camera that allows a physician to inspect a patient's windpipe and airways, and a rigid tube may be used in conjunction with the bronchoscope for surgical purposes, e.g., when there is a significant amount of bleeding in the lungs of the patient or when a large object obstructs the throat of the patient. When the rigid tube is used, the patient is often anesthetized. Robotic bronchoscopes provide tremendous advantages in navigation through tubular networks. They can ease use and allow therapies and biopsies to be administered conveniently even during the bronchoscopy stage.

Apart from mechanical devices or platforms, e.g., robotic bronchoscopes described above, various methods and software models may be used to help with the surgical operations. As an example, a computerized tomography (CT) scan of the patient's lungs is often performed during pre-operation of a surgical examination. Data from the CT scan may be used to generate a three-dimensional (3D) model of airways of the patient's lungs, and the generated 3D model enables a physician to access a visual reference that may be useful during the operative procedure of the surgical examination.

However, previous techniques for navigation of tubular networks still have challenges, even when employing medical devices (e.g., robotic bronchoscopes) and when using existing methods (e.g., performing CT scans and generating 3D models). As one example, motion estimation of a medical device (e.g., a bronchoscope tool) inside a patient's body may not be accurate based on location and orientation change of the device, and as a result the device's position may not be accurately or correctly localized inside the patient's body in real time. Inaccurate location information for such an instrument may provide misleading information to the physician that uses the 3D model as a visual reference during medical operation procedures.

Thus, there is a need for improved techniques for navigating through a network of tubular structures.

SUMMARY

Robotic systems and methods for navigation of luminal network that can improve strain-based shape sensing are described. In one aspect, the system can compare strain-based shape data to shape data determined based on robotic data (e.g., command data, force and distance data, mechanical model data, kinematic model data, etc.) and adjust the strain-based shape data as necessary. Any portion of the strain-based shape data can be adjusted, weighted differently, or discarded based on the comparison. For example, data from trustworthy sources may indicate that the shape of an instrument exhibits or should exhibit one or more characteristics. If the system determines that any portion of the strain-based shape data is not in agreement with such characteristics, the system may adjust the portion of the strain-based shape data such that the adjusted strain-based shape data is in agreement with the characteristics of the instrument.

Accordingly, one aspect relates to a method of navigating an instrument within an interior region of a body. The method may include: accessing robotic data regarding the instrument; accessing strain data from an optical fiber positioned within the instrument that is indicative of a strain on a portion of the instrument positioned within the interior region of the body; determining shape data based on the strain data; comparing the robotic data and the shape data; adjusting the shape data based on the comparison of the robotic data and the shape data; determining an estimated state of the instrument based on the adjusted shape data; and outputting the estimated state of the instrument.

The aspect described in the above paragraph may also include one or more of the following features in any combination: (a) wherein adjusting the shape data comprises modifying at least a portion of the shape data such that the determination of the estimated state of the instrument is based on the modified portion of the shape data; (b) wherein adjusting the shape data comprises removing at least a portion of the shape data such that the determination of the estimated state of the instrument is not based on the removed portion of the shape data; (c) wherein the method further includes accessing electromagnetic (EM) data captured using (i) an EM sensor located proximal to a tip of the instrument and (ii) at least one external EM sensor or EM field generator located external to the body, comparing the EM data and the shape data, and further adjusting the shape data based on the comparison of the EM data and the shape data; (d) wherein the method further includes accessing image data captured by an imaging device located proximal to a tip of the instrument, comparing the image data and the shape data, and further adjusting the shape data based on the comparison of the image data and the shape data; (e) wherein the strain data is generated based on fiber Bragg gratings (FBGs) created on a portion of the optical fiber; (f) wherein the shape data comprises one of a curvature value of the portion of the instrument or time history data of the portion of the instrument; (g) wherein the method further includes adjusting the shape data based on a determination that the curvature value is greater than or equal to a threshold curvature value in the robotic data; (h) wherein the method further includes adjusting the shape data based on a determination that the time history data satisfies a threshold time history condition in the robotic data; (i) wherein the method further includes adjusting the shape data based on a change of temperature; (j) wherein the method further includes adjusting the shape data based on a determination that a tip of the instrument is being articulated; (k) wherein the method further includes adjusting the shape data based on a determination that non-shape-changing strain is being applied to the instrument; (l) wherein the method further includes assigning, based on a determination that a first portion of the instrument comprises a distal end of the instrument, a confidence value to the robotic data corresponding to the first portion that is higher than that assigned to the shape data corresponding to the first portion; (m) wherein the method further includes assigning, based on a determination that a first portion of the instrument comprises a proximal end of the instrument, a confidence value to the robotic data corresponding to the first portion that is lower than that assigned to the shape data corresponding to the first portion; (n) wherein the method further includes determining an estimated state of a sheath covering the instrument based on the estimated state of the instrument; (o) wherein the method further includes assigning a confidence value to the shape data based on a comparison of the shape data and additional data indicative of a shape of a sheath covering the instrument; (p) wherein the method further includes determining, based on the estimated state of the instrument, that a damage to the instrument is imminent, and controlling the instrument such that the damage is avoided; and (q) wherein the method further includes determining that a mismatch between the robotic data and the shape data has been detected for at least a threshold amount of time, and outputting an alert indicating that the instrument may be damaged.

Another aspect relates to a method of navigating an instrument within an interior region of a body. The method may include: accessing robotic data regarding the instrument; accessing strain data from an optical fiber positioned within the instrument that is indicative of a strain on a portion of the instrument positioned within the interior region of the body; determining shape data based on the strain data; comparing the robotic data and the shape data; adjusting a confidence value associated with the shape data based on the comparison of the robotic data and the shape data; determining an estimated state of the instrument based on the adjusted confidence value; and outputting the estimated state of the instrument.

The aspect described in the above paragraph may also include one or more of the following features in any combination: (a) wherein the method further includes accessing electromagnetic (EM) data captured using (i) an EM sensor located proximal to a tip of the instrument and (ii) at least one external EM sensor or EM field generator located external to the body, comparing the EM data and the shape data, and adjusting the confidence value associated with the shape data based further on the comparison of the EM data and the shape data; (b) wherein the method further includes accessing image data captured by an imaging device located proximal to a tip of the instrument, comparing the image data and the shape data, and adjusting the confidence value associated with the shape data based further on the comparison of the image data and the shape data; (c) wherein the strain data is generated based on fiber Bragg gratings (FBGs) created on a portion of the optical fiber; (d) wherein the shape data comprises one of a curvature value of the portion of the instrument or time history data of the portion of the instrument; (e) wherein the method further includes adjusting the confidence value based on a determination that the curvature value is greater than or equal to a threshold curvature value in the robotic data; (f) wherein the method further includes adjusting the confidence value based on a determination that the time history data satisfies a threshold time history condition in the robotic data; (g) wherein the method further includes adjusting the confidence value based on a change of temperature; (h) adjusting the confidence value based on a determination that a tip of the instrument is being articulated; (i) wherein the method further includes adjusting the confidence value based on a determination that non-shape-changing strain is being applied to the instrument; (j) wherein the method further includes assigning, based on a determination that a first portion of the instrument comprises a distal end of the instrument, a confidence value to the robotic data corresponding to the first portion that is higher than that assigned to the shape data corresponding to the first portion; (k) wherein the method further includes assigning, based on a determination that a first portion of the instrument comprises a proximal end of the instrument, a confidence value to the robotic data corresponding to the first portion that is lower than that assigned to the shape data corresponding to the first portion; (l) wherein the method further includes determining an estimated state of a sheath covering the instrument based on the estimated state of the instrument; (m) wherein the method further includes adjusting the confidence value based further on a comparison of the shape data and additional data indicative of a shape of a sheath covering the instrument; (n) wherein the method further includes determining, based on the estimated state of the instrument, that a damage to the instrument is imminent, and controlling the instrument such that the damage is avoided; and (o) wherein the method further includes determining that a mismatch between the robotic data and the shape data has been detected for at least a threshold amount of time, and outputting an alert indicating that the instrument may be damaged.

BRIEF DESCRIPTION OF THE DRAWINGS

The disclosed aspects will hereinafter be described in conjunction with the appended drawings, provided to illustrate and not to limit the disclosed aspects, wherein like designations denote like elements.

Reference will now be made in detail to several embodiments, examples of which are illustrated in the accompanying figures. It is noted that wherever practicable similar or like reference numbers may be used in the figures and may indicate similar or like functionality. The figures depict embodiments of the described system (or method) for purposes of illustration only. One skilled in the art will readily recognize from the following description that alternative embodiments of the structures and methods illustrated herein may be employed without departing from the principles described herein.

DETAILED DESCRIPTION

I. Surgical Robotic System

Figure 1A:
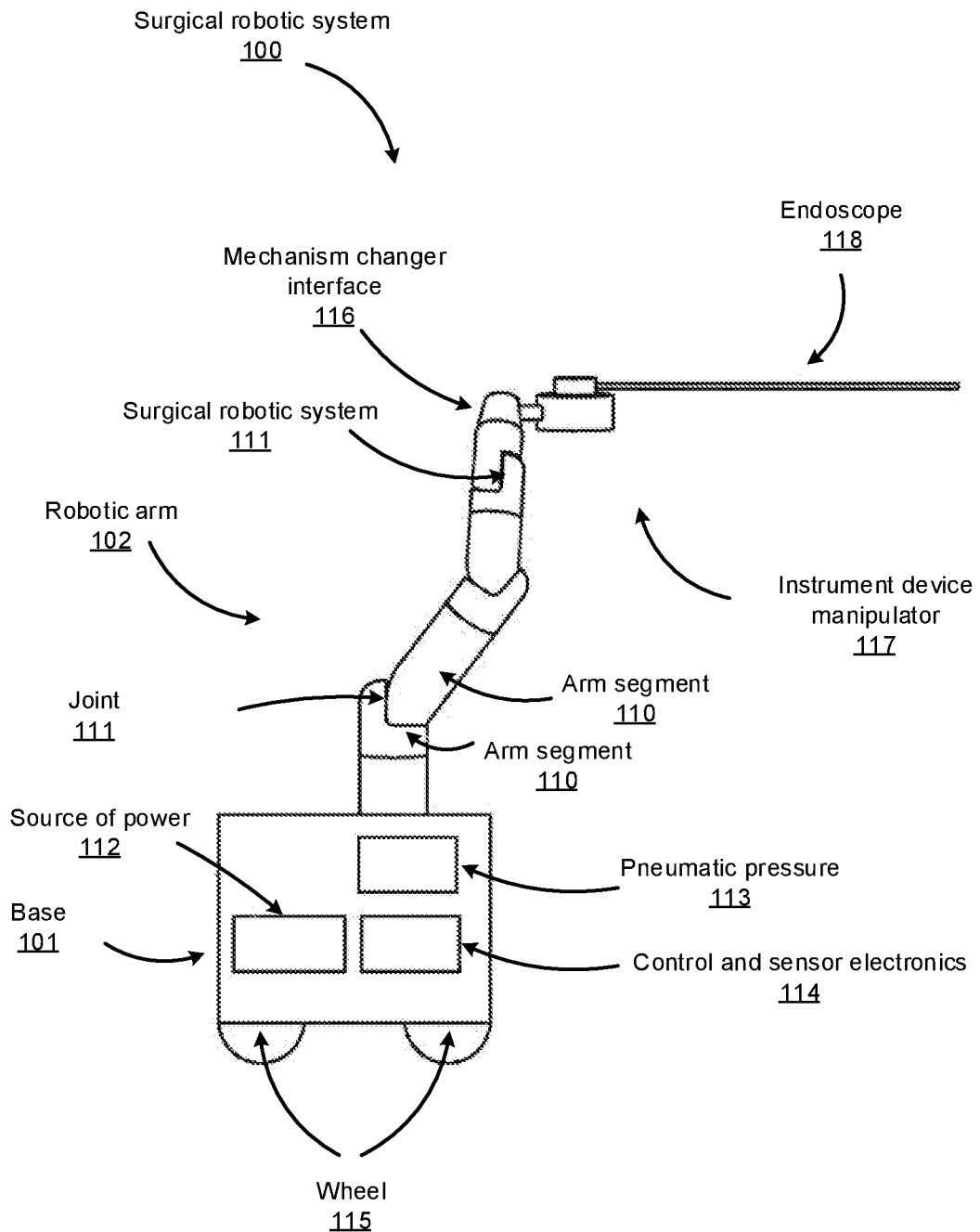
FIG. 1A shows an example surgical robotic system, according to one embodiment.

FIG. 1A shows an example surgical robotic system 100, according to one embodiment. The surgical robotic system 100 includes a base 101 coupled to one or more robotic arms, e.g., robotic arm 102. The base 101 is communicatively coupled to a command console, which is further described with reference to FIG. 2 in Section II. Command Console. The base 101 can be positioned such that the robotic arm 102 has access to perform a surgical procedure on a patient, while a user such as a physician may control the surgical robotic system 100 from the comfort of the command console. In some embodiments, the base 101 may be coupled to a surgical operating table or bed for supporting the patient. Though not shown in FIG. 1 for purposes of clarity, the base 101 may include subsystems such as control electronics, pneumatics, power sources, optical sources, and the like. The robotic arm 102 includes multiple arm segments 110 coupled at joints 111, which provides the robotic arm 102 multiple degrees of freedom, e.g., seven degrees of freedom corresponding to seven arm segments. The base 101 may contain a source of power 112, pneumatic pressure 113, and control and sensor electronics 114—including components such as a central processing unit, data bus, control circuitry, and memory—and related actuators such as motors to move the robotic arm 102. The electronics 114 in the base 101 may also process and transmit control signals communicated from the command console.

In some embodiments, the base 101 includes wheels 115 to transport the surgical robotic system 100. Mobility of the surgical robotic system 100 helps accommodate space constraints in a surgical operating room as well as facilitate appropriate positioning and movement of surgical equipment. Further, the mobility allows the robotic arms 102 to be configured such that the robotic arms 102 do not interfere with the patient, physician, anesthesiologist, or any other equipment. During procedures, a user may control the robotic arms 102 using control devices such as the command console.

In some embodiments, the robotic arm 102 includes set up joints that use a combination of brakes and counter-balances to maintain a position of the robotic arm 102. The counter-balances may include gas springs or coil springs. The brakes, e.g., fail safe brakes, may be include mechanical and/or electrical components. Further, the robotic arms 102 may be gravity-assisted passive support type robotic arms.

Each robotic arm 102 may be coupled to an instrument device manipulator (IDM) 117 using a mechanism changer interface (MCI) 116. The IDM 117 can be removed and replaced with a different type of IDM, for example, a first type of IDM manipulates an endoscope, while a second type of IDM manipulates a laparoscope. The MCI 116 includes connectors to transfer pneumatic pressure, electrical power, electrical signals, and optical signals from the robotic arm 102 to the IDM 117. The MCI 116 can be a set screw or base plate connector. The IDM 117 manipulates surgical instruments such as the endoscope 118 using techniques including direct drive, harmonic drive, geared drives, belts and pulleys, magnetic drives, and the like. The MCI 116 is interchangeable based on the type of IDM 117 and can be customized for a certain type of surgical procedure. The robotic arm 102 can include a joint level torque sensing and a wrist at a distal end, such as the KUKA AG® LBR5 robotic arm.

The endoscope 118 is a tubular and flexible surgical instrument that is inserted into the anatomy of a patient to capture images of the anatomy (e.g., body tissue). In particular, the endoscope 118 includes one or more imaging devices (e.g., cameras or other types of optical sensors) that capture the images. The imaging devices may include one or more optical components such as an optical fiber, fiber array, or lens. The optical components move along with the tip of the endoscope 118 such that movement of the tip of the endoscope 118 results in changes to the images captured by the imaging devices. The endoscope 118 is further described with reference to FIGS. 3A-4B in Section IV. Endoscope.

Robotic arms 102 of the surgical robotic system 100 manipulate the endoscope 118 using elongate movement members. The elongate movement members may include pull wires, also referred to as pull or push wires, cables, fibers, or flexible shafts. For example, the robotic arms 102 actuate multiple pull wires coupled to the endoscope 118 to deflect the tip of the endoscope 118. The pull wires may include both metallic and non-metallic materials such as stainless steel, Kevlar, tungsten, carbon fiber, and the like. The endoscope 118 may exhibit nonlinear behavior in response to forces applied by the elongate movement members. The nonlinear behavior may be based on stiffness and compressibility of the endoscope 118, as well as variability in slack or stiffness between different elongate movement members.

Figure 1B:
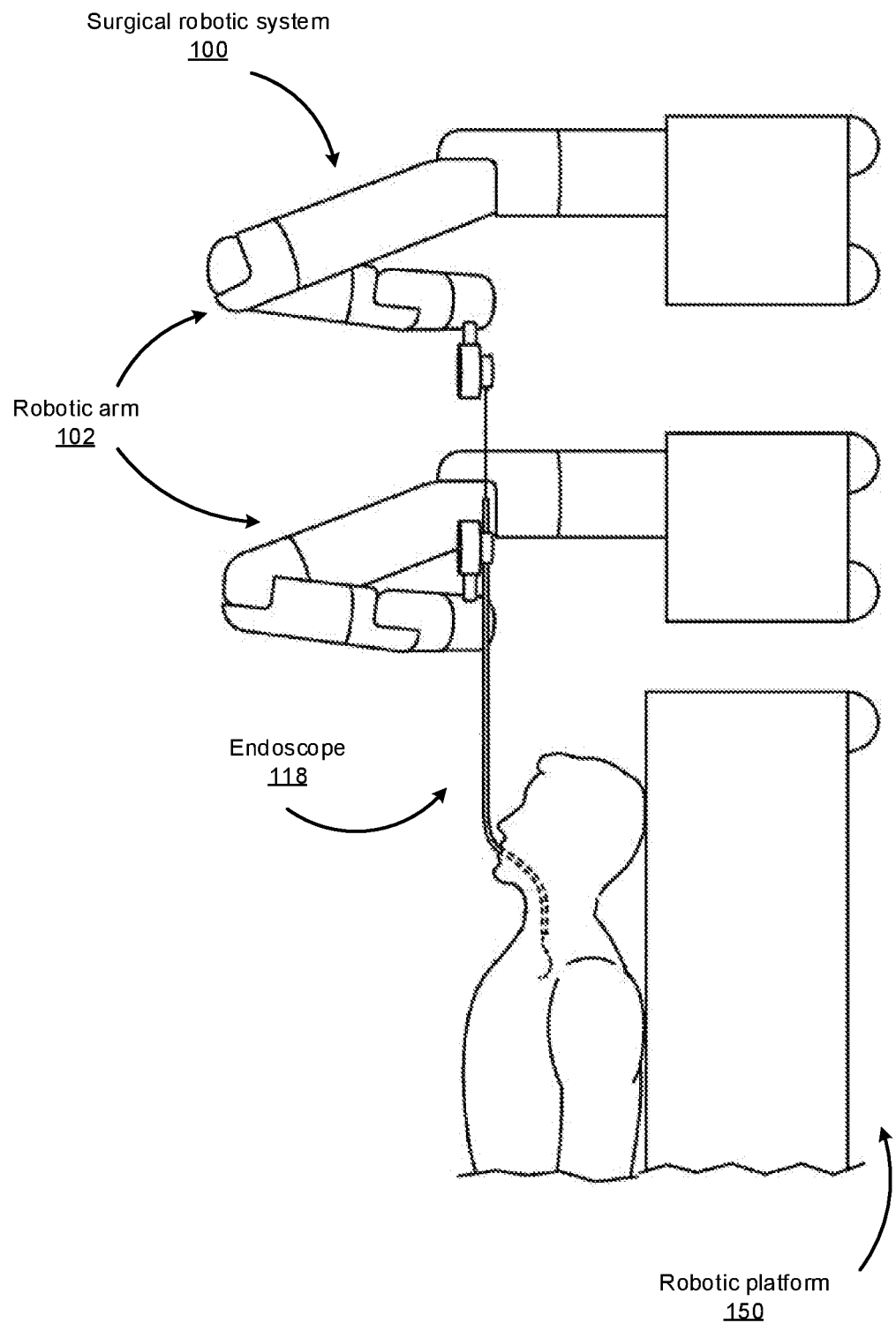
FIGS. 1B-1F show various perspective views of a robotic platform coupled to the surgical robotic system shown in FIG. 1A, according to one embodiment.
Figure 1C:
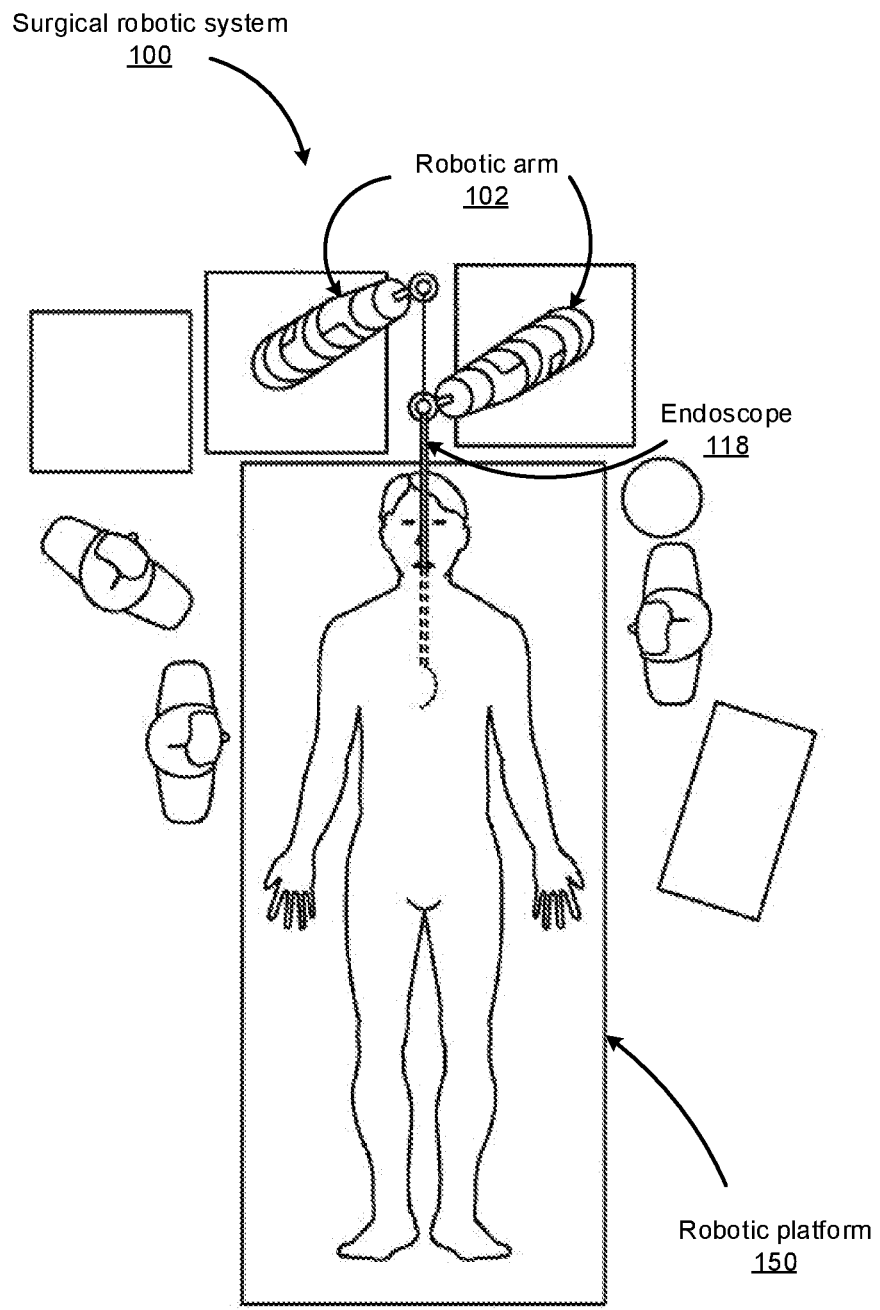
Figure 1D:
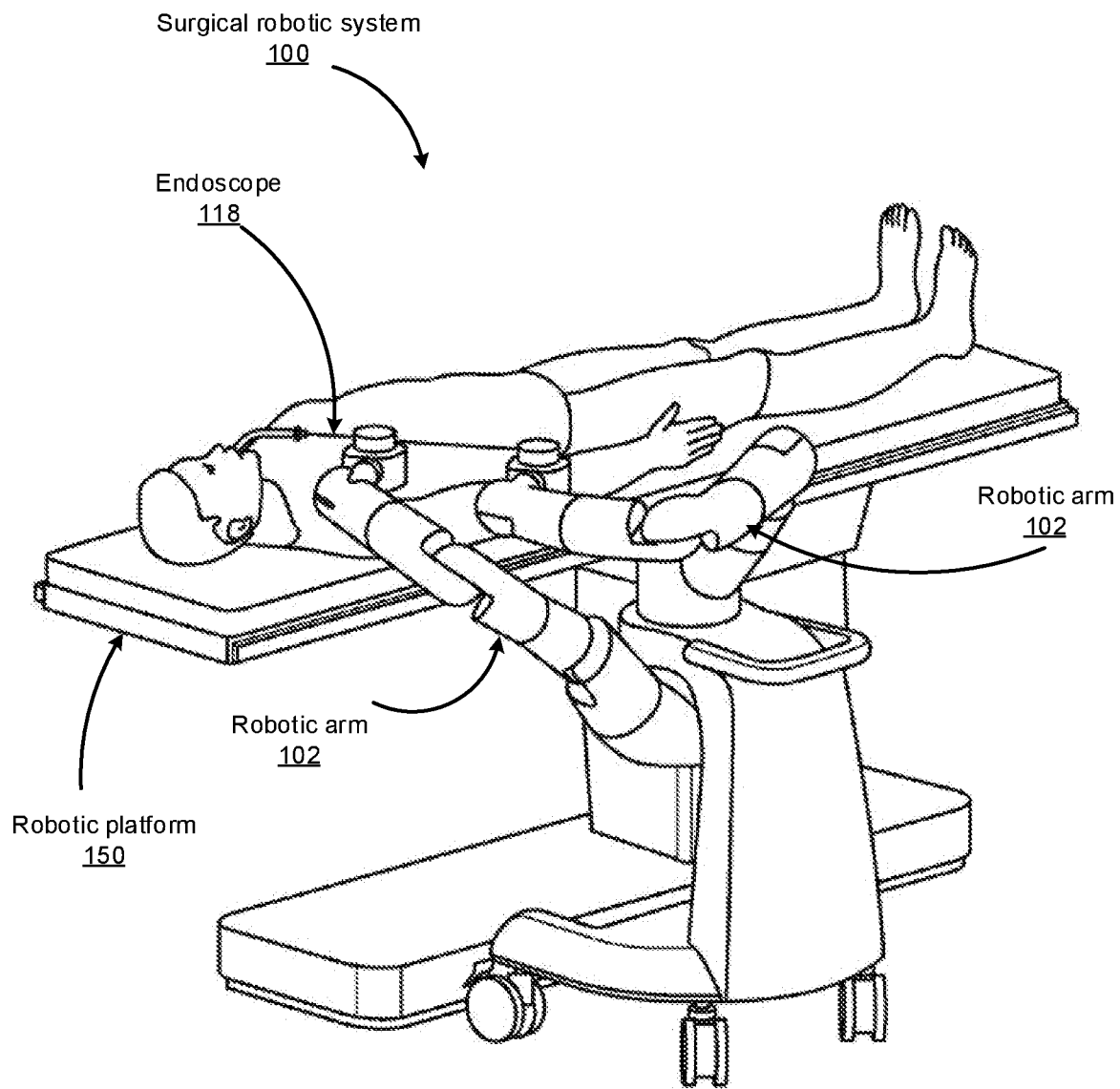
Figure 1E:
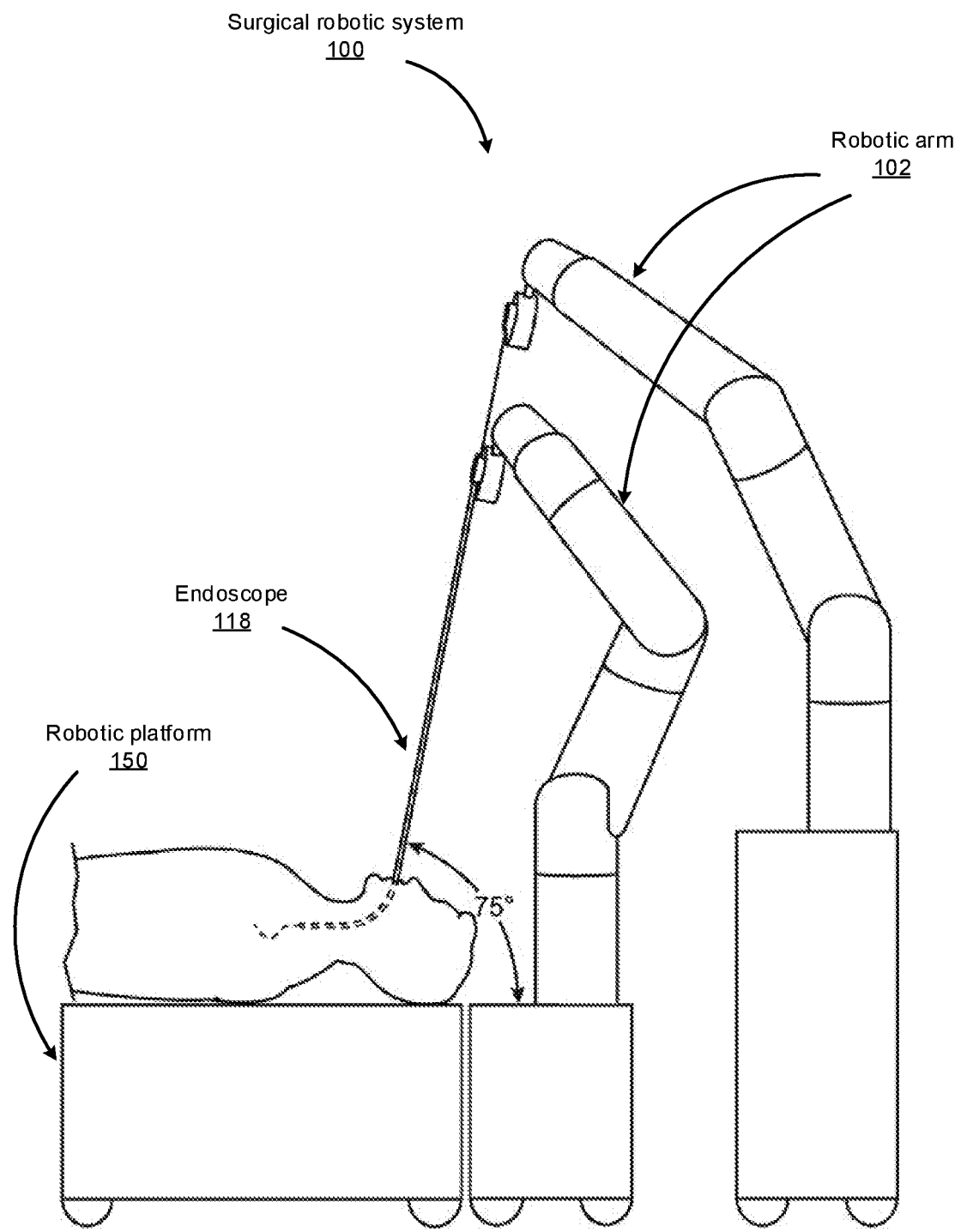
Figure 1F:
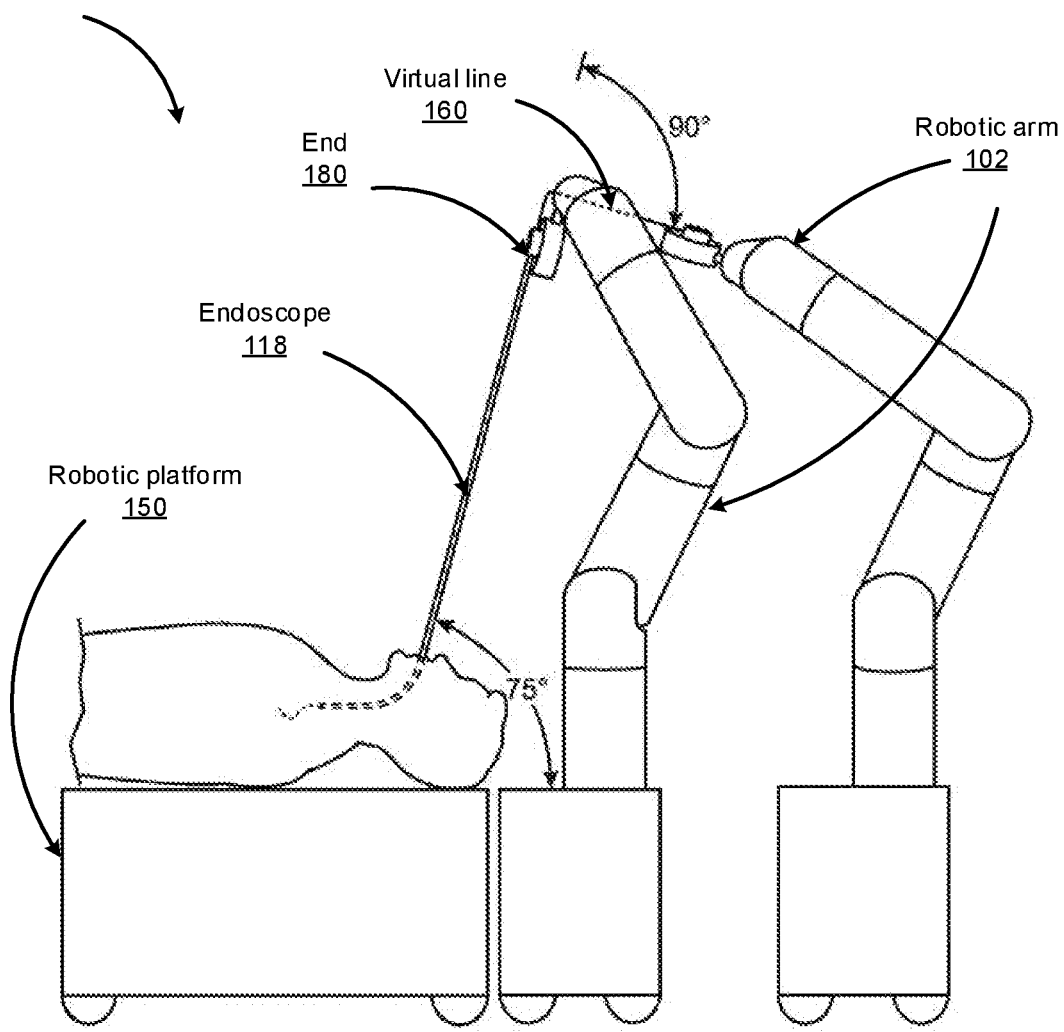

FIGS. 1B-1F show various perspective views of the surgical robotic system 100 coupled to a robotic platform 150 (or surgical bed), according to various embodiments. Specifically, FIG. 1B shows a side view of the surgical robotic system 100 with the robotic arms 102 manipulating the endoscope 118 to insert the endoscope inside a patient's body, and the patient is lying on the robotic platform 150. FIG. 1C shows a top view of the surgical robotic system 100 and the robotic platform 150, and the endoscope 118 manipulated by the robotic arms is inserted inside the patient's body. FIG. 1D shows a perspective view of the surgical robotic system 100 and the robotic platform 150, and the endoscope 118 is controlled to be positioned horizontally parallel with the robotic platform. FIG. 1E shows another perspective view of the surgical robotic system 100 and the robotic platform 150, and the endoscope 118 is controlled to be positioned relatively perpendicular to the robotic platform. In more detail, in FIG. 1E, the angle between the horizontal surface of the robotic platform 150 and the endoscope 118 is 75 degree. FIG. 1F shows the perspective view of the surgical robotic system 100 and the robotic platform 150 shown in FIG. 1E, and in more detail, the angle between the endoscope 118 and the virtual line 160 connecting one end 180 of the endoscope 118 and the robotic arm 102 that is positioned relatively farther away from the robotic platform is 90 degree.

II. Command Console

Figure 2:
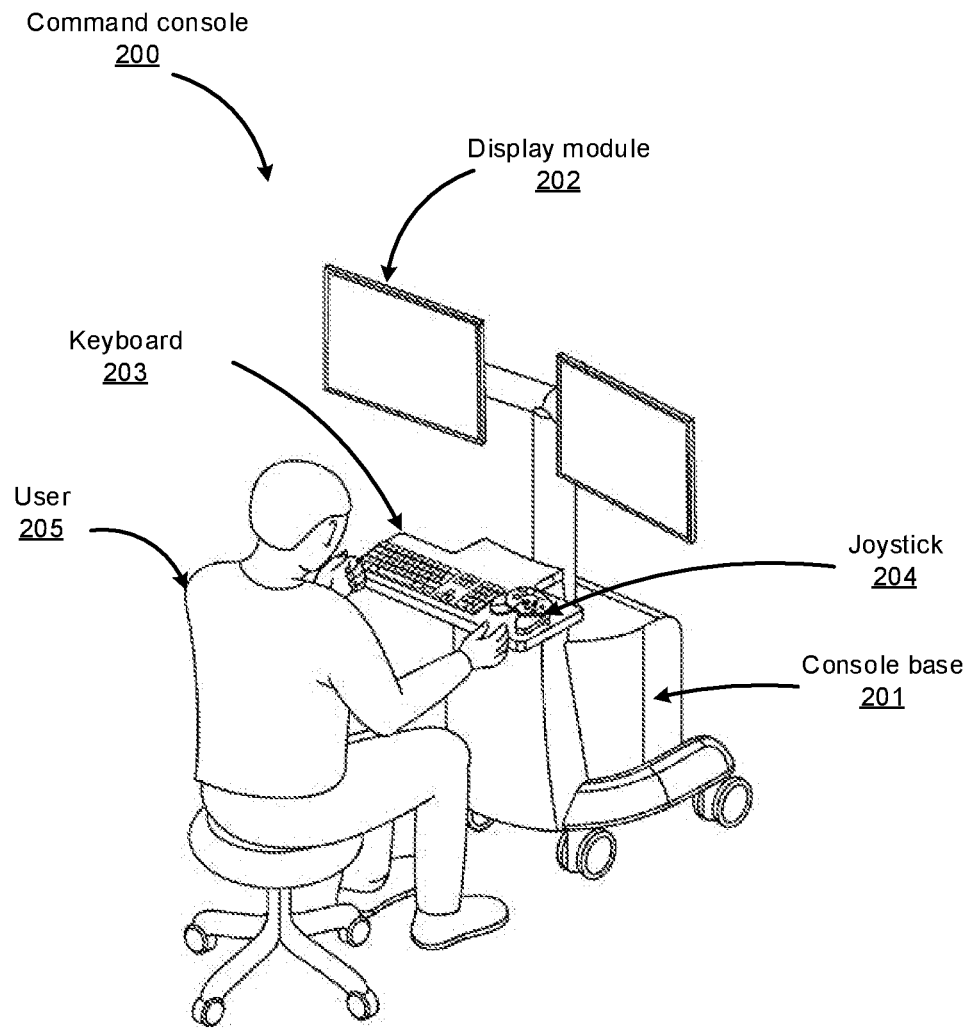
FIG. 2 shows an example command console for the example surgical robotic system, according to one embodiment.

FIG. 2 shows an example command console 200 for the example surgical robotic system 100, according to one embodiment. The command console 200 includes a console base 201, display modules 202, e.g., monitors, and control modules, e.g., a keyboard 203 and joystick 204. In some embodiments, one or more of the command console 200 functionality may be integrated into a base 101 of the surgical robotic system 100 or another system communicatively coupled to the surgical robotic system 100. A user 205, e.g., a physician, remotely controls the surgical robotic system 100 from an ergonomic position using the command console 200.

The console base 201 may include a central processing unit, a memory unit, a data bus, and associated data communication ports that are responsible for interpreting and processing signals such as camera imagery and tracking sensor data, e.g., from the endoscope 118 shown in FIG. 1. In some embodiments, both the console base 201 and the base 101 perform signal processing for load-balancing. The console base 201 may also process commands and instructions provided by the user 205 through the control modules 203 and 204. In addition to the keyboard 203 and joystick 204 shown in FIG. 2, the control modules may include other devices, for example, computer mice, trackpads, trackballs, control pads, video game controllers, and sensors (e.g., motion sensors or cameras) that capture hand gestures and finger gestures.

The user 205 can control a surgical instrument such as the endoscope 118 using the command console 200 in a velocity mode or position control mode. In velocity mode, the user 205 directly controls pitch and yaw motion of a distal end of the endoscope 118 based on direct manual control using the control modules. For example, movement on the joystick 204 may be mapped to yaw and pitch movement in the distal end of the endoscope 118. The joystick 204 can provide haptic feedback to the user 205. For example, the joystick 204 vibrates to indicate that the endoscope 118 cannot further translate or rotate in a certain direction. The command console 200 can also provide visual feedback (e.g., pop-up messages) and/or audio feedback (e.g., beeping) to indicate that the endoscope 118 has reached maximum translation or rotation.

In position control mode, the command console 200 uses a three-dimensional (3D) map of a patient and pre-determined computer models of the patient to control a surgical instrument, e.g., the endoscope 118. The command console 200 provides control signals to robotic arms 102 of the surgical robotic system 100 to manipulate the endoscope 118 to a target location. Due to the reliance on the 3D map, position control mode requires accurate mapping of the anatomy of the patient.

In some embodiments, users 205 can manually manipulate robotic arms 102 of the surgical robotic system 100 without using the command console 200. During setup in a surgical operating room, the users 205 may move the robotic arms 102, endoscopes 118, and other surgical equipment to access a patient. The surgical robotic system 100 may rely on force feedback and inertia control from the users 205 to determine appropriate configuration of the robotic arms 102 and equipment.

The display modules 202 may include electronic monitors, virtual reality viewing devices, e.g., goggles or glasses, and/or other means of display devices. In some embodiments, the display modules 202 are integrated with the control modules, for example, as a tablet device with a touchscreen. Further, the user 205 can both view data and input commands to the surgical robotic system 100 using the integrated display modules 202 and control modules.

The display modules 202 can display 3D images using a stereoscopic device, e.g., a visor or goggle. The 3D images provide an "endo view" (i.e., endoscopic view), which is a computer 3D model illustrating the anatomy of a patient. The "endo view" provides a virtual environment of the patient's interior and an expected location of an endoscope 118 inside the patient. A user 205 compares the "endo view" model to actual images captured by a camera to help mentally orient and confirm that the endoscope 118 is in the correct—or approximately correct—location within the patient. The "endo view" provides information about anatomical structures, e.g., the shape of an intestine or colon of the patient, around the distal end of the endoscope 118. The display modules 202 can simultaneously display the 3D model and computerized tomography (CT) scans of the anatomy the around distal end of the endoscope 118. Further, the display modules 202 may overlay the already determined navigation paths of the endoscope 118 on the 3D model and scans/images generated based on preoperative model data (e.g., CT scans).

In some embodiments, a model of the endoscope 118 is displayed with the 3D models to help indicate a status of a surgical procedure. For example, the CT scans identify a lesion in the anatomy where a biopsy may be necessary. During operation, the display modules 202 may show a reference image captured by the endoscope 118 corresponding to the current location of the endoscope 118. The display modules 202 may automatically display different views of the model of the endoscope 118 depending on user settings and a particular surgical procedure. For example, the display modules 202 show an overhead fluoroscopic view of the endoscope 118 during a navigation step as the endoscope 118 approaches an operative region of a patient.

III. Instrument Device Manipulator

Figure 3A:
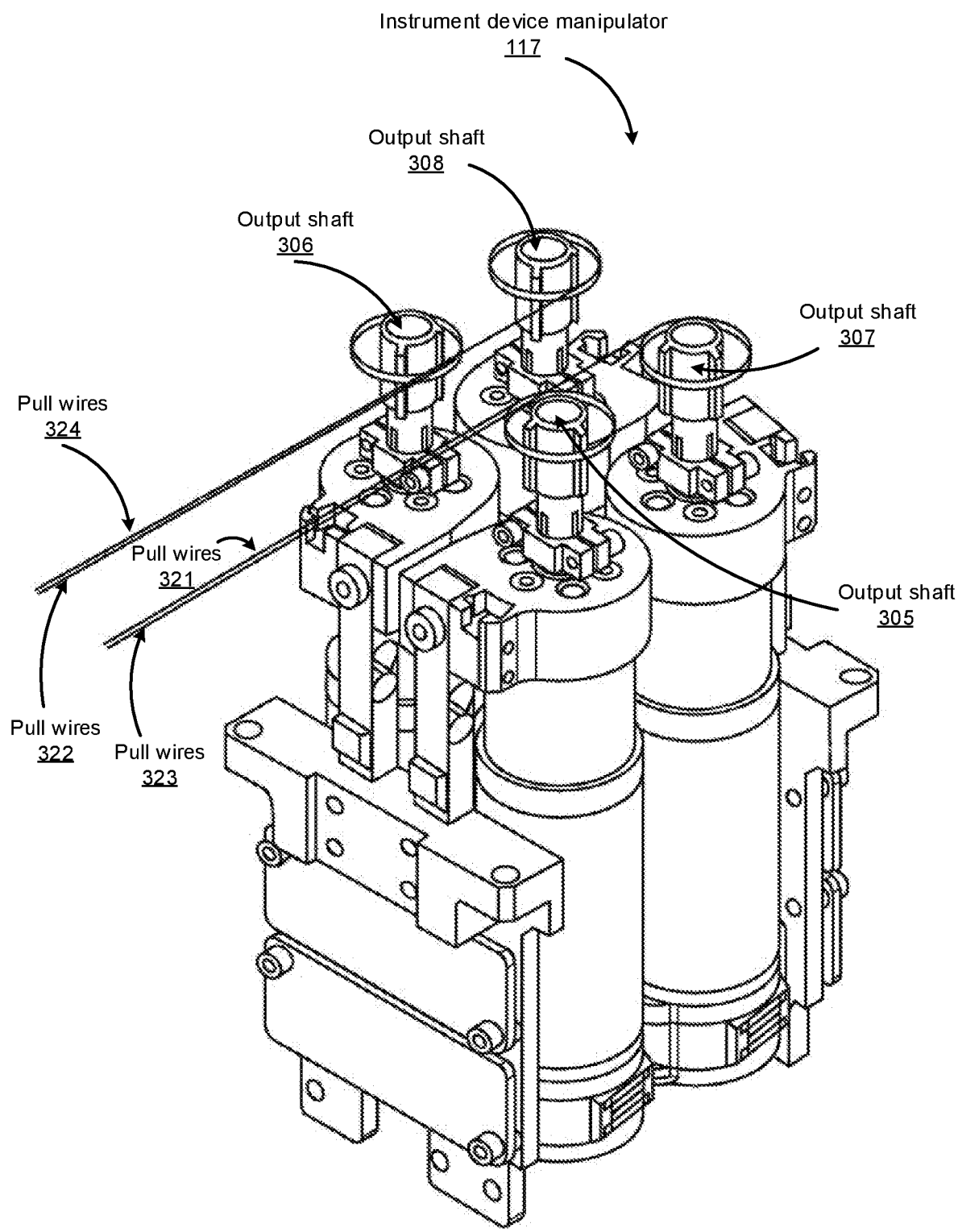
FIG. 3A shows an isometric view of an example independent drive mechanism of the instrument device manipulator (IDM) shown in FIG. 1A, according to one embodiment.

FIG. 3A shows an isometric view of an example independent drive mechanism of the IDM 117 shown in FIG. 1, according to one embodiment. The independent drive mechanism can tighten or loosen the pull wires 321, 322, 323, and 324 (e.g., independently from each other) of an endoscope by rotating the output shafts 305, 306, 307, and 308 of the IDM 117, respectively. Just as the output shafts 305, 306, 307, and 308 transfer force down pull wires 321, 322, 323, and 324, respectively, through angular motion, the pull wires 321, 322, 323, and 324 transfer force back to the output shafts. The IDM 117 and/or the surgical robotic system 100 can measure the transferred force using a sensor, e.g., a strain gauge further described below.

Figure 3B:
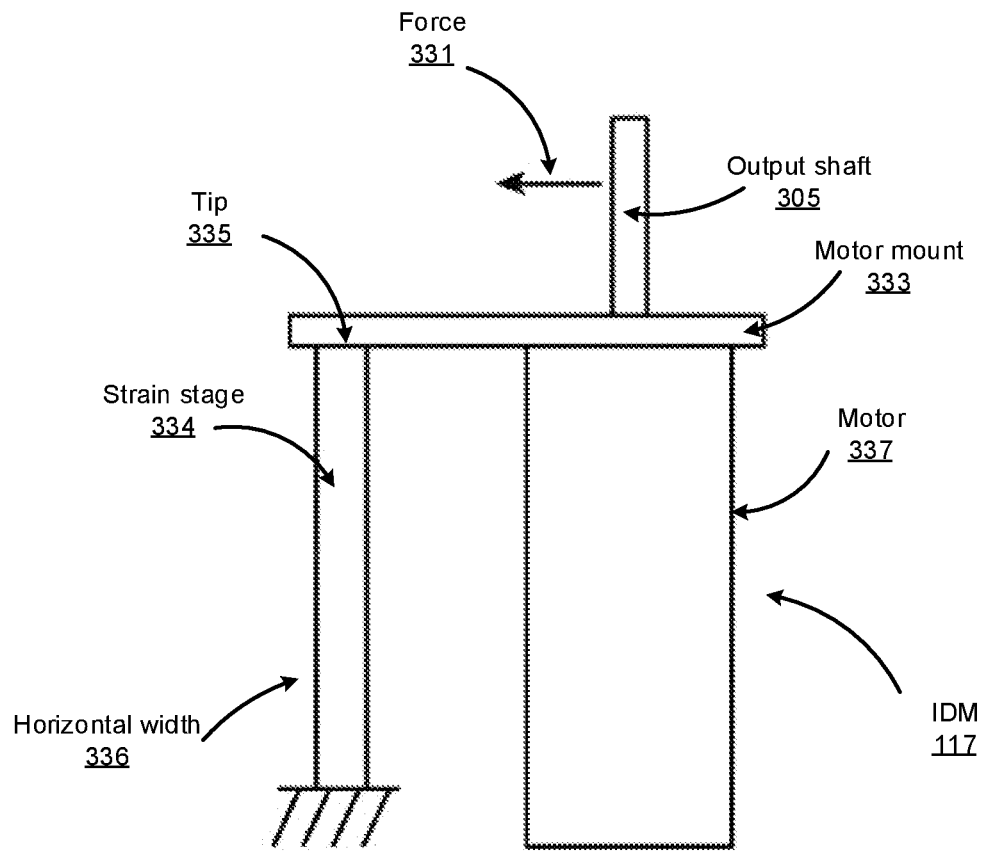
FIG. 3B shows a conceptual diagram that shows how forces may be measured by a strain gauge of the independent drive mechanism shown in FIG. 3A, according to one embodiment.

FIG. 3B shows a conceptual diagram that shows how forces may be measured by a strain gauge 334 of the independent drive mechanism shown in FIG. 3A, according to one embodiment. A force 331 may direct away from the output shaft 305 coupled to the motor mount 333 of the motor 337. Accordingly, the force 331 results in horizontal displacement of the motor mount 333. Further, the strain gauge 334 horizontally coupled to the motor mount 333 experiences strain in the direction of the force 331. The strain may be measured as a ratio of the horizontal displacement of the tip 335 of strain gauge 334 to the overall horizontal width 336 of the strain gauge 334.

In some embodiments, the IDM 117 includes additional sensors, e.g., inclinometers or accelerometers, to determine an orientation of the IDM 117. Based on measurements from the additional sensors and/or the strain gauge 334, the surgical robotic system 100 can calibrate readings from the strain gauge 334 to account for gravitational load effects. For example, if the IDM 117 is oriented on a horizontal side of the IDM 117, the weight of certain components of the IDM 117 may cause a strain on the motor mount 333. Accordingly, without accounting for gravitational load effects, the strain gauge 334 may measure strain that did not result from strain on the output shafts.

IV. Endoscope

IV. A. Endoscope Top View

Figure 4A:
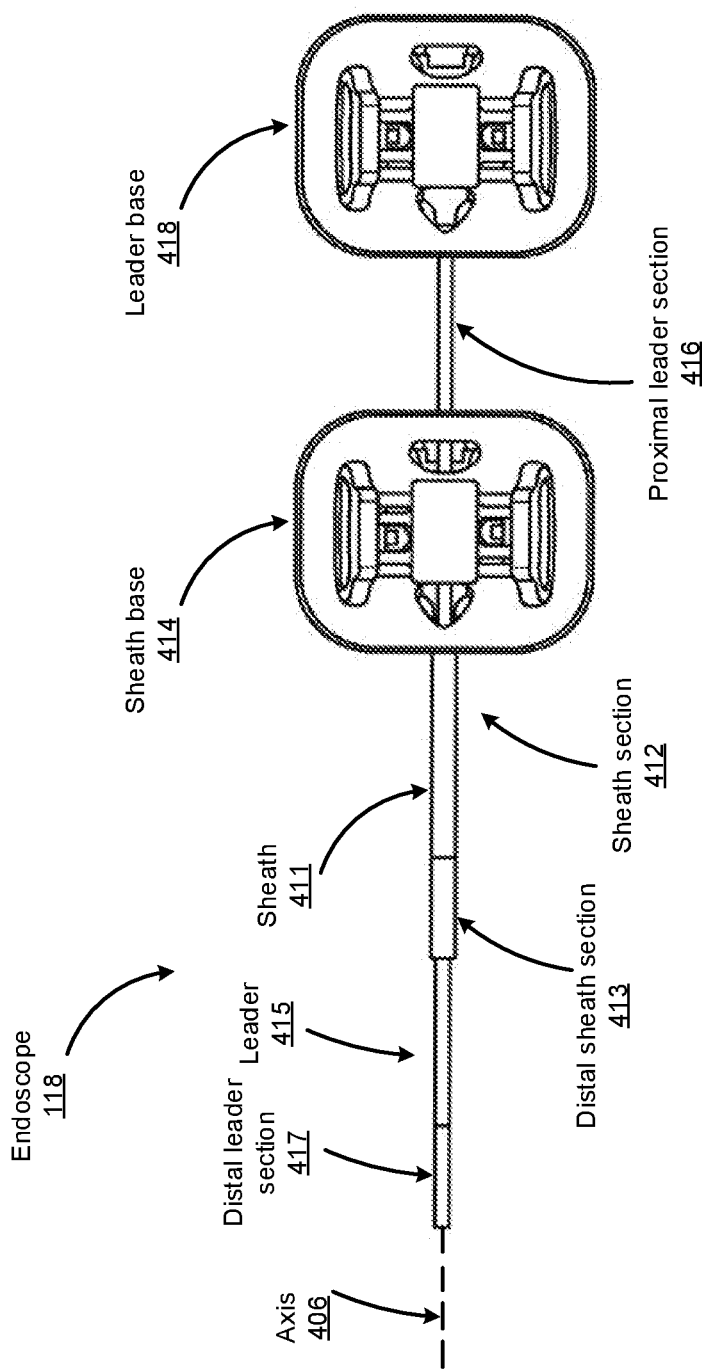
FIG. 4A shows a top view of an example endoscope, according to one embodiment.

FIG. 4A shows a top view of an example endoscope 118, according to one embodiment. The endoscope 118 includes a leader 415 tubular component nested or partially nested inside and longitudinally-aligned with a sheath 411 tubular component. The sheath 411 includes a proximal sheath section 412 and distal sheath section 413. The leader 415 has a smaller outer diameter than the sheath 411 and includes a proximal leader section 416 and distal leader section 417. The sheath base 414 and the leader base 418 actuate the distal sheath section 413 and the distal leader section 417, respectively, for example, based on control signals from a user of a surgical robotic system 100. The sheath base 414 and the leader base 418 are, e.g., part of the IDM 117 shown in FIG. 1.

Both the sheath base 414 and the leader base 418 include drive mechanisms (e.g., the independent drive mechanism further described with reference to FIG. 3A-B in Section III. Instrument Device Manipulator) to control pull wires coupled to the sheath 411 and leader 415. For example, the sheath base 414 generates tensile loads on pull wires coupled to the sheath 411 to deflect the distal sheath section 413. Similarly, the leader base 418 generates tensile loads on pull wires coupled to the leader 415 to deflect the distal leader section 417. Both the sheath base 414 and leader base 418 may also include couplings for the routing of pneumatic pressure, electrical power, electrical signals, or optical signals from IDMs to the sheath 411 and leader 415, respectively. A pull wire may include a steel coil pipe along the length of the pull wire within the sheath 411 or the leader 415, which transfers axial compression back to the origin of the load, e.g., the sheath base 414 or the leader base 418, respectively.

Figure 4B:
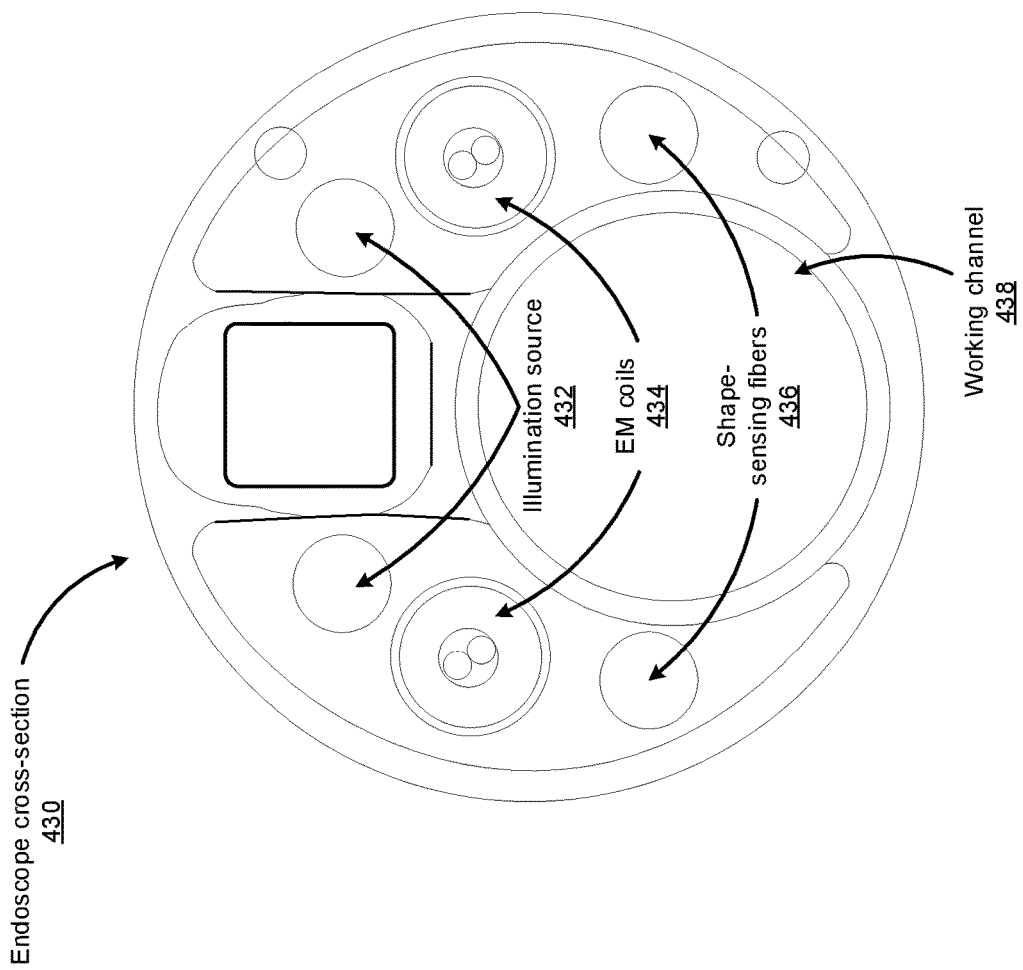
FIG. 4B shows an example endoscope cross-section of the endoscope shown in FIG. 4A, according to one embodiment.

The endoscope 118 can navigate the anatomy of a patient with ease due to the multiple degrees of freedom provided by pull wires coupled to the sheath 411 and the leader 415. For example, four or more pull wires may be used in either the sheath 411 and/or the leader 415, providing eight or more degrees of freedom. In other embodiments, up to three pull wires may be used, providing up to six degrees of freedom. The sheath 411 and leader 415 may be rotated up to 360 degrees along a longitudinal axis 406, providing more degrees of motion. The combination of rotational angles and multiple degrees of freedom provides a user of the surgical robotic system 100 with a user friendly and instinctive control of the endoscope 118. Although not illustrated in FIG. 4A, the endoscope 118 may include one or more optical fibers for sensing the shape in one or more portions of the endoscope 118. For example, as illustrated in FIG. 4B, the optical fiber(s) can be included in the leader portion of the endoscope 118. Alternatively or additionally, the optical fiber(s) can be included in the sheath portion of the endoscope 118. As will be explained in more detail below, information from the optical fibers can be used in combination with information from other input sources, such as other input sensors, modelling data, known properties and characteristics of the endoscope, and the like, to enhance performance of the navigation system, catheter control, or the like.

IV. B. Endoscope Cross-Sectional View

FIG. 4B illustrates an example endoscope cross-section 430 of the endoscope 118 shown in FIG. 4A, according to one embodiment. In FIG. 4B, the endoscope cross-section 430 includes illumination sources 432, electromagnetic (EM) coils 434, and shape-sensing fibers 436. The illumination sources 432 provide light to illuminate an interior portion of an anatomical space. The provided light may allow an imaging device provided at the tip of the endoscope 118 to record images of that space, which can then be transmitted to a computer system such as command console 200 for processing as described herein. EM coils 434 may be used with an EM tracking system to detect the position and orientation of the tip of the endoscope 118 while it is disposed within an anatomical system. In some embodiments, the coils may be angled to provide sensitivity to EM fields along different axes, giving the ability to measure a full 6 degrees of freedom: three positional and three angular. In other embodiments, only a single coil may be disposed within the tip of the endoscope 118, with its axis oriented along the endoscope shaft of the endoscope 118; due to the rotational symmetry of such a system, it is insensitive to roll about its axis, so only 5 degrees of freedom may be detected in such a case. The endoscope cross-section 430 further includes a working channel 438 through which surgical instruments, such as biopsy needles, may be inserted along the endoscope shaft, allowing access to the area near the endoscope tip. "Instruments" as used herein can refer to surgical instruments, medical instruments, and any other instrument or device that can be navigated in a luminal network.

While the illustrated embodiment is disclosed as including illumination sources 432 and EM coils 434 and corresponding imaging device and EM tracking system, it is anticipated that modified embodiments of the endoscopes described herein can be without one or more of such features. Further, while the shape-sensing fibers 436 are described as being integrated into the endoscope 118, in other embodiments, any of the one or more shape-sensing fibers 436 can instead be a removable working channel device that can be inserted into the working channel 438 and removed from the working channel 438 after shape sensing is performed. In other embodiments, the shape-sensing fibers 436 may be mounted external to the endoscope 118.

IV. C. Shape-Sensing Optical Fibers

Figure 4C:
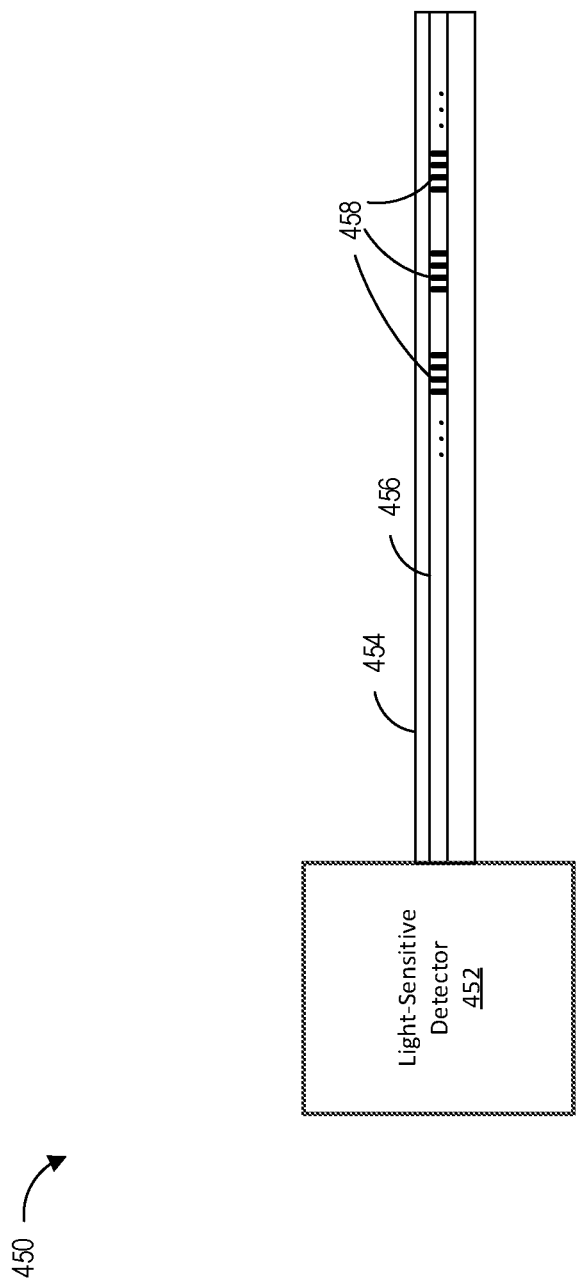
FIG. 4C shows an example strain-based shape sensing mechanism, according to one embodiment.

FIG. 4C shows a system 450 having a shape detector 452, which can be used to generate and detect light used for determining the shape of the instrument, an endoscope 454, and an optical fiber 456. The optical fiber 456 can include one or more segments of fiber Bragg gratings (FBG) 458, which reflect certain wavelengths of light while transmitting other wavelengths. The gratings 458 may comprise a series of modulations of refractive index so as to generate a spatial periodicity in the refraction index. During fabrication of the gratings 458, the modulations can be spaced by a known distance, thereby causing reflection of a known band of wavelengths. The shape detector 452 may transmit light through the optical fiber 456 and receive light reflected from the optical fiber 456. The shape detector 452 may further generate reflection spectrum data based on the wavelengths of light reflected by the gratings 458.

As shown in FIG. 4C, a single optical fiber may include multiple sets of fiber Bragg gratings. The endoscope 454 may include multiple optical fibers, and the shape detector 452 may detect and analyze signals from more than one fiber. One or more optical fibers may be included in the leader 415 of FIG. 4A, the sheath 411 of FIG. 4A, or both. Although the endoscope 454 is used as an example, the techniques described herein can be applied to any other elongated instrument. The shape detector 452 may be operatively coupled with a controller configured to determine a geometric shape or configuration of the optical fiber 456 and, therefore, at least a portion of the endoscope 454 (or other elongated instrument such as a catheter and the like) based on a spectral analysis of the detected reflected light signals.

The controller within or in communication with the shape detector 452 (e.g., the surgical robotic system 500) can analyze the reflection spectrum data to generate position and orientation data of the endoscope 454 in two or three dimensional space. In particular, as the endoscope 454 bends, the optical fiber 456 positioned inside also bends, which causes strain on the optical fiber 456. When strain is induced on the optical fiber 456, the spacing of the modulations will change, depending on the amount of strain on the optical fiber 456. To measure strain, light is sent down the optical fiber 456, and characteristics of the returning light are measured. For example, the gratings 458 may produce a reflected wavelength that is a function of the strain on the optical fiber 456 (and other factors such as temperature). Based on the specific wavelengths of light reflected by the gratings 458, the system can determine the amount of strain on the optical fiber 456 and further predict the shape of the optical fiber 456 based on the amount of strain (e.g., based on how the strain characteristics of a "straight" endoscope may differ from those of a "curved" endoscope). Thus, the system can determine, for example, how many degrees the endoscope 454 has bent in one or more directions (e.g., in response to commands from the surgical robotic system 500) by identifying differences in the reflection spectrum data.

In some embodiments, the optical fiber 456 includes multiple cores within a single cladding. In such embodiments, each core may operate as a separate optical fiber with sufficient distance and cladding separating the cores such that the light in each core does not interact significantly with the light carried in other cores. In other embodiments, the number of cores may vary or each core may be contained in a separate optical fiber. When the strain and shape analysis is applied to a multicore optical fiber, bending of the optical fiber 456 may induce strain on the cores that can be measured by monitoring the wavelength shifts in each core. By having two or more cores disposed off-axis in the optical fiber 456, bending of the optical fiber induces different strains on each of the cores. These strains are a function of the local degree of bending of the fiber. For example, regions of the cores containing the gratings 458, if located at points where the optical fiber 456 is bent, can thereby be used to determine the amount of bending at those points. These data, combined with the known spacings of the gratings 458, can be used to reconstruct the shape of the optical fiber 456.

The optical fiber is suitable for data collection inside the body of the patient because no line-of-sight to the shape sensing optical fiber is required. Various systems and methods for monitoring the shape and relative position of an optical fiber in three dimensions are described in U.S. Patent Application Publication No. 2006/0013523, filed Jul. 13, 2005, titled "FIBER OPTIC POSITION AND SHAPE SENSING DEVICE AND METHOD RELATING THERETO," and U.S. Pat. No. 6,389,187, filed on Jun. 17, 1998, entitled "OPTICAL FIBER BEND SENSOR," the contents of which are fully incorporated herein by reference.

While the illustrated embodiment utilizes a fiber with Bragg gratings, in a modified variation, an optical fiber can include slight imperfections that result in index of refraction variations along the fiber core. These variations can result in a small amount of backscatter that is called Rayleigh scatter. Changes in strain or temperature of the optical fiber cause changes to the effective length of the optical fiber. This change in the effective length results in variation or change of the spatial position of the Rayleigh scatter points. Cross correlation techniques can measure this change in the Rayleigh scattering and can extract information regarding the strain. These techniques can include using optical frequency domain reflectometer techniques in a manner that is very similar to that associated with low reflectivity fiber gratings.

Methods and devices for calculating birefringence in an optical fiber based on Rayleigh scatter as well as apparatus and methods for measuring strain in an optical fiber using the spectral shift of Rayleigh scatter can be found in PCT Publication No. WO 2006/099056 filed on Mar. 9, 2006 and U.S. Pat. No. 6,545,760 filed on Mar. 24, 2000, both of which are fully incorporated herein by reference. Birefringence can be used to measure axial strain and/or temperature in a waveguide.

IV. D. Improving Strain-Based Shape Data

Strain-based shape sensing can allow reconstruction of the shape of an endoscope or other instrument by measuring the strain along the optical fibers that run inside the instrument. The measurement of the strain captures the spatiotemporal variations of the reflection of light on gratings inside the optical fibers. The distance between each grating affects the reflection and can therefore be used to measure the strain at a precise location along the optical fiber (or the instrument). However, in some cases, strain-based shape sensing can be negatively affected by noise. In such cases, it can be difficult to distinguish between a real change in strain and a false one.

An improved strain-based shape sensing system can utilize other data available to the system (e.g., robotic data, image data, EM data, etc.) to improve the precision of (or adjust the confidence in) its strain-based shape sensing or state estimations determined based on such strain-based shape sensing. Alternatively or additionally, an improved strain-based shape sensing system can utilize the shape data determined based on its strain-based shape sensing to improve the precision of (or adjust the confidence in) its other data (e.g., robotic data, image data, EM data, etc.) or state estimations determined based on such data.

Figure 4D:
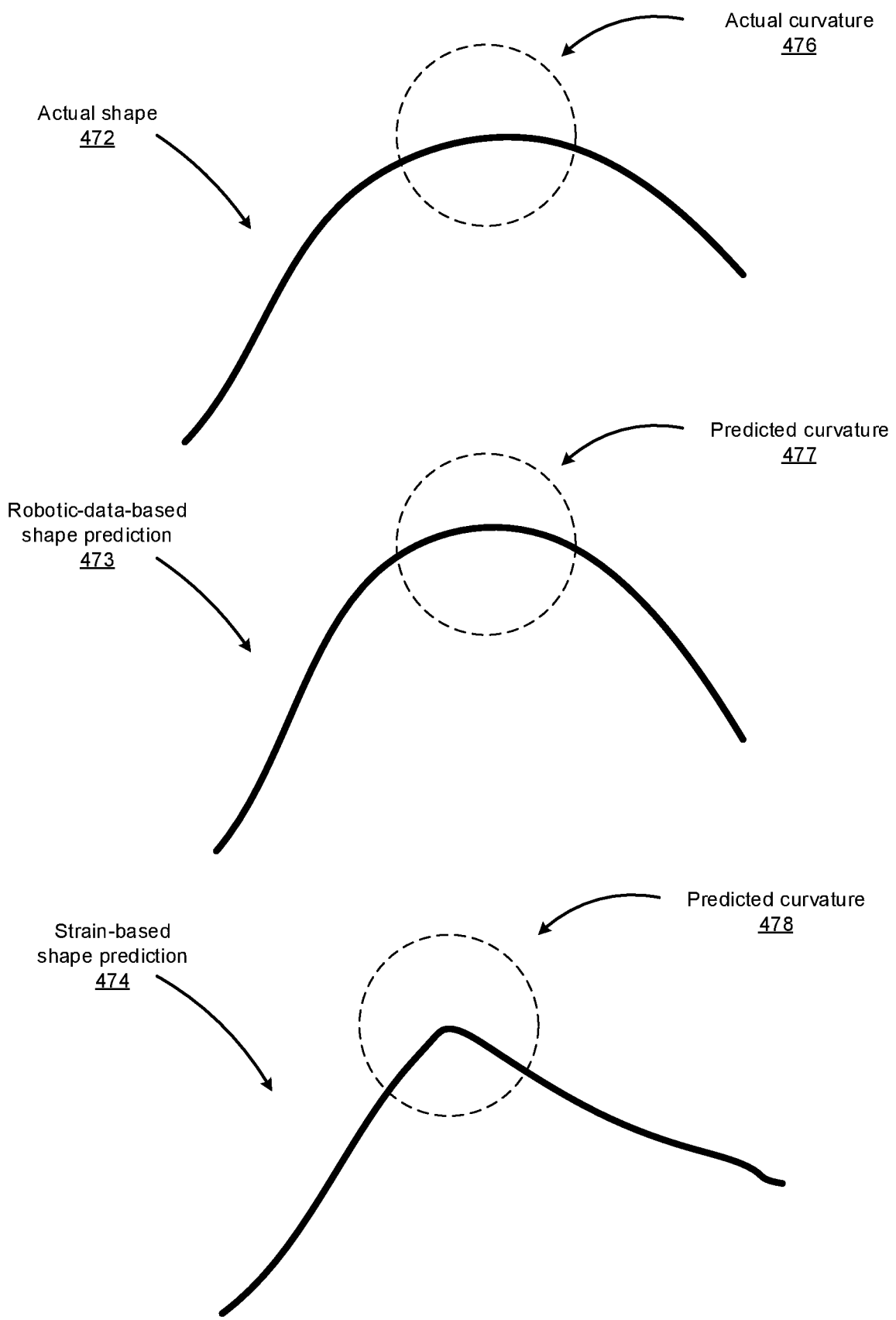
FIGS. 4D-4E show actual shapes of an example endoscope and strain-based predictions of the endoscope, according to one embodiment.
Figure 4E:
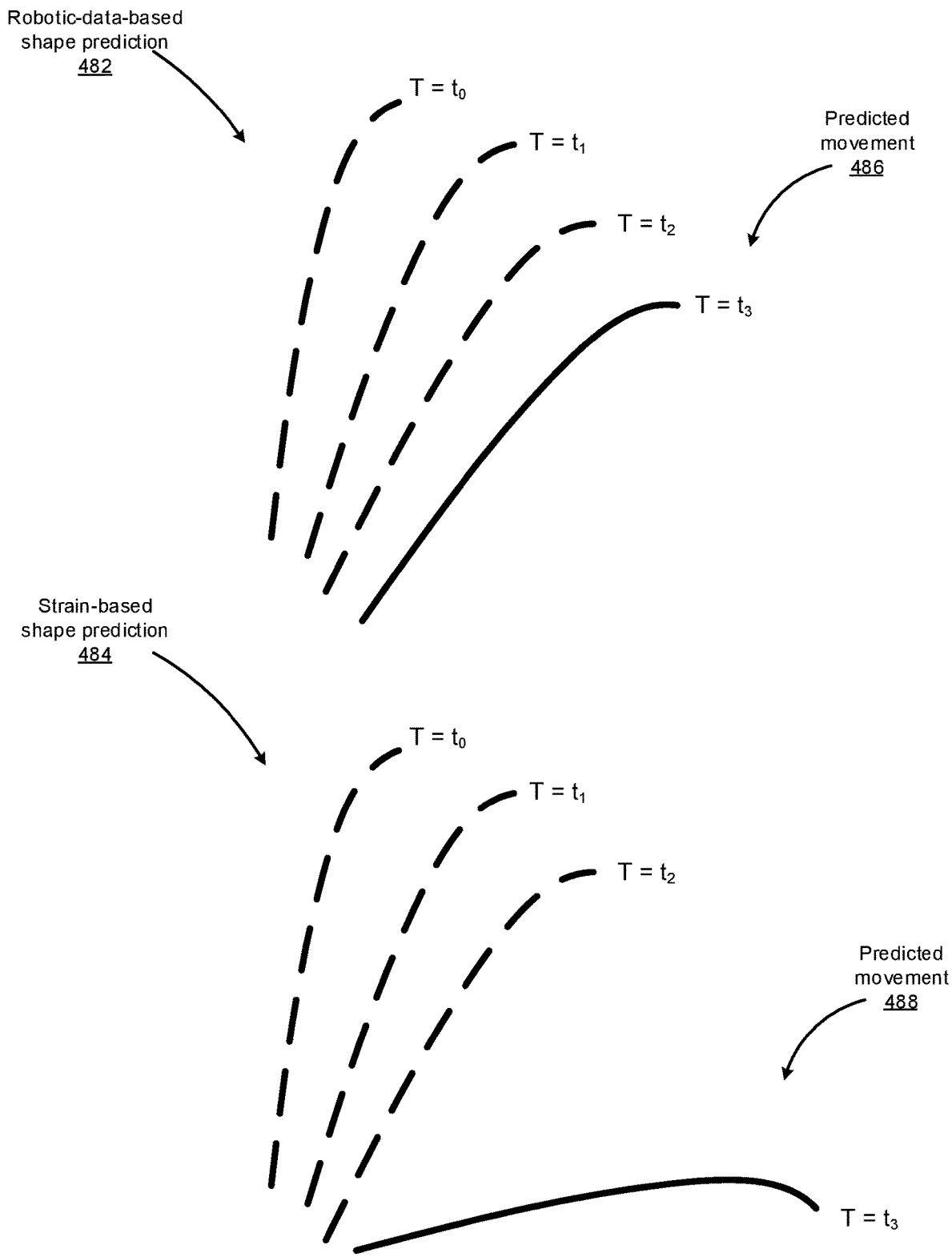

FIGS. 4D-4E illustrate how the system may utilize information available to the system to improve, adjust, or weight its strain-based shape sensing. The system may access data available to the system such as robotic data (e.g., command data, force and distance data, mechanical model data, kinematic model data, etc.) and determine, based on such data, certain characteristics about the shape of the instrument (or specific portions thereof) navigated within a patient's body. Such characteristics may include curvature information (e.g., maximum curvature that the instrument is capable of exhibiting, or a range of acceptable curvature values given the current force and distance data indicated by the robotic data), movement information (e.g., maximum speed at which the instrument is capable of moving, or a range of acceptable speed values given the current force and distance data indicated by the robotic data), sheath information (e.g., current shape of the sheath covering one or more portions of the instrument), and the like. Upon determining that the strain-based shape prediction does not satisfy one or more constraints indicated by these characteristics determined based on the robotic data, the system can adjust the strain-based shape prediction such that the adjusted strain-based shape prediction satisfies the constraints, reduce the confidence or weight associated with the particular strain-based shape prediction, or disregard the strain-based shape prediction.

FIG. 4D shows actual shape 472 of the endoscope 118, robotic-data-based shape prediction 473, and strain-based shape prediction 474 of the endoscope 118. The actual shape 472 exhibits an actual curvature 476, whereas the robotic-data-based shape prediction 473 exhibit a predicted curvature 477, and the strain-based shape prediction 474 exhibits a predicted curvature 478. In the example of FIG. 4D, the system may determine, based on the robotic data, one or more conditions that the endoscope 118 is expected to satisfy (e.g., the curvature value at a given point along the endoscope 118 should be within a predetermined range of values, or should be within a range of values determined based on the pull force on the pull wires and/or the distances that the pull wires have been actuated). Upon determining that a portion of the strain-based shape prediction 474 does not satisfy such conditions (e.g., by indicating a predicted curvature value that is outside an expected curvature value range as determined based on the robotic data corresponding to the endoscope 118), the system can adjust the strain-based shape prediction 474 such that the portion of the strain-based shape prediction 474 satisfies the conditions (e.g., such that the shape data no longer indicates a predicted curvature value that is outside the expected curvature value range), reduce the confidence or weight associated with the portion of the strain-based shape prediction 474, or disregard the portion of the strain-based shape prediction 474 (e.g., refrain from using the portion of the strain-based shape prediction 474 in estimating the current state of the endoscope 118). For example, as shown in FIG. 4D, the system may determine, based on the robotic data (e.g., pull force and distances), the robotic-data-based shape prediction 473 exhibiting the predicted curvature 477 at a given point. The system may compare the predicted curvature 477 to the predicted curvature 478 exhibited by the strain-based shape prediction 474. Upon determining that the predicted curvature 478 is different from the predicted curvature 477, the system may adjust the predicted curvature 487 to equal the predicted curvature 477. Alternatively, upon determining that the predicted curvature 478 is not within a given threshold range (e.g., ±10 percent) from the predicted curvature 477, the system may adjust the predicted curvature 487 to be within the threshold range (e.g., set to the upper bound of the threshold range if the predicted curvature 478 exceeds the range, and set to the lower bound of the threshold range if the predicted curvature 478 falls short of the range). Additionally or alternatively, the system may lower the confidence value associated with the strain-based shape prediction 474 based on a determination that the predicted curvature 478 is different from the predicted curvature 477 (or that the predicted curvature 478 is not within the given threshold range), and/or increase the confidence value associated with the strain-based shape prediction 474 based on a determination that the predicted curvature 478 equals the predicted curvature 477 (or that the predicted curvature 478 is within the given threshold range).

FIG. 4E shows robotic-data-based shape prediction 482 of the endoscope 118 and strain-based shape prediction 484 of the endoscope 118. The robotic-data-based shape prediction 482 exhibits a predicted movement 486, whereas the strain-based shape prediction 484 exhibits a predicted movement 488. As described with reference to FIG. 4D, the system may determine, based on the robotic data, one or more conditions that the endoscope 118 is expected to satisfy. For example, based on the robotic data, the system may determine that the speed at which the endoscope 118 moves should be within a certain range of values). Upon determining that a portion of the strain-based shape prediction 484 does not satisfy such conditions, the system can adjust the strain-based shape prediction 484 such that the portion of the strain-based shape prediction 484 satisfies the conditions (e.g., such that the shape data no longer indicates a predicted speed value that is outside the expected speed value range), reduce the confidence or weight associated with the portion of the strain-based shape prediction 484, or disregard the portion of the strain-based shape prediction 484 (e.g., refrain from using the portion of the strain-based shape prediction 484 in estimating the current state of the endoscope 118). For example, as shown in FIG. 4E, the system may determine, based on the robotic data (e.g., pull force and/or distances as a function of time), the robotic-data-based shape prediction 482 exhibiting the predicted movement 486. The system may compare the predicted movement 486 to the predicted movement 488 exhibited by the strain-based shape prediction 484. Upon determining that the predicted movement 488 is different from the predicted movement 486, the system may adjust the predicted movement 488 to be identical to the predicted movement 486. Alternatively, upon determining that the predicted movement 488 is not within a given threshold range (e.g., movement speed being within ±10 percent of the movement speed of the predicted movement 486), the system may adjust the predicted movement 488 to be within the threshold range (e.g., set to the upper bound of the threshold movement speed range if the predicted movement speed of the strain-based shape prediction 484 exceeds the movement speed range, and set to the lower bound of the threshold movement speed range if the predicted movement speed of the strain-based shape prediction 484 falls short of the movement speed range). Additionally or alternatively, the system may lower the confidence value associated with the strain-based shape prediction 484 based on a determination that the predicted movement 488 is different from the predicted movement 486 (or that the predicted movement 488 is not within the given threshold), and/or increase the confidence value associated with the strain-based shape prediction 484 based on a determination that the predicted movement 488 is identical to the predicted movement 486 (or that the predicted movement 488 is within the given threshold).

The process of collecting strain data and other data (some or all of which can be utilized to improve the strain-based shape data) and determining state estimations is described in greater detail below with reference to FIGS. 8-11.

V. Registration Transform of EM System to 3D Model

V. A. Schematic Setup of an EM Tracking System

Figure 5:
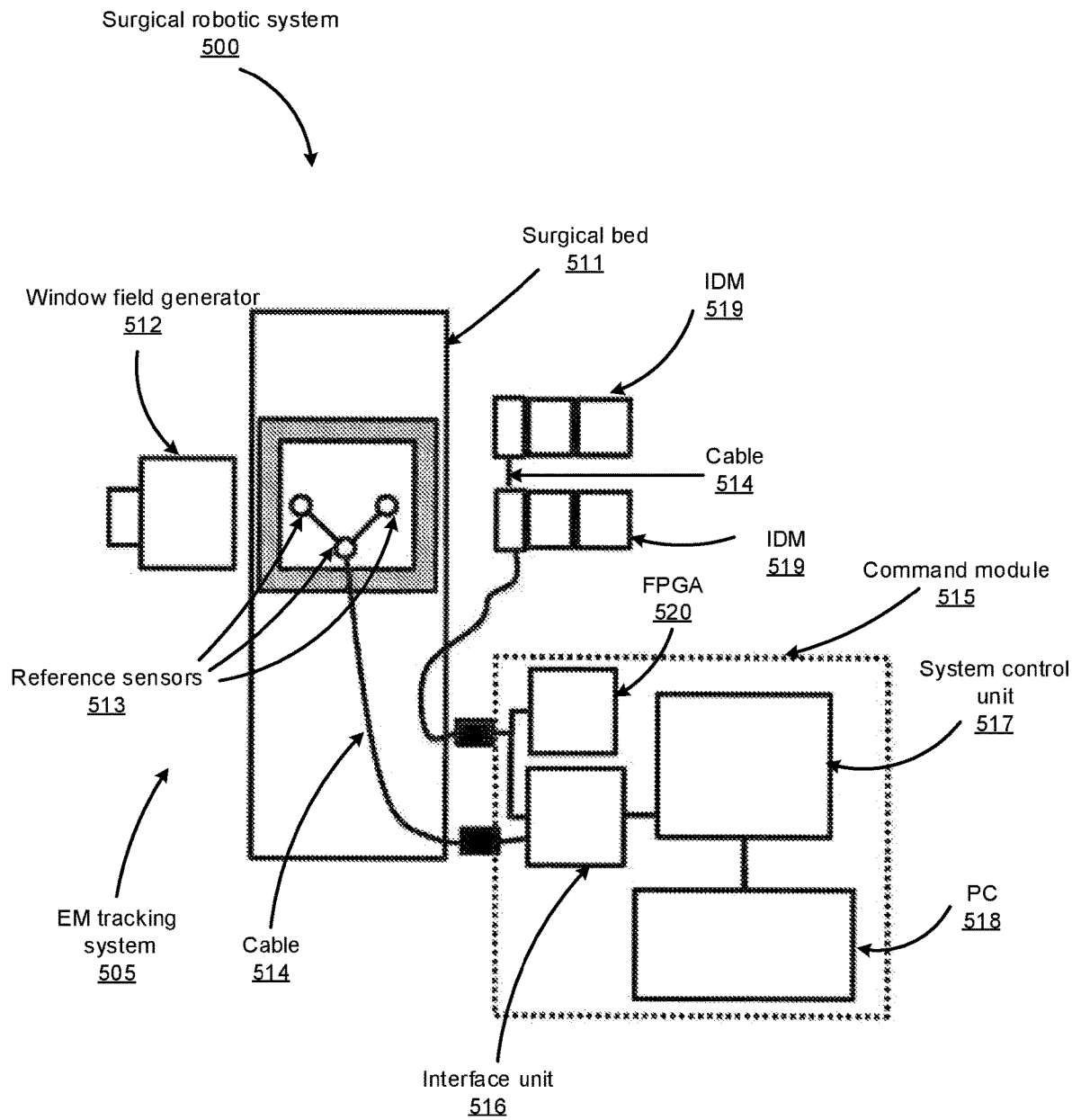
FIG. 5 shows an example schematic setup of an EM tracking system included in a surgical robotic system, according to one embodiment.

In certain embodiments an EM tracking system can be used in combination with the systems described herein. FIG. 5 shows an example schematic setup of such an EM tracking system 505 that can be included in a surgical robotic system 500, according to one embodiment. In FIG. 5, multiple robot components (e.g., window field generator, reference sensors as described below) are included in the EM tracking system 505. The surgical robotic system 500 includes a surgical bed 511 to hold a patient's body. Beneath the bed 511 is the window field generator (WFG) 512 configured to sequentially activate a set of EM coils (e.g., the EM coils 434 shown in FIG. 4B). The WFG 512 generates an alternating current (AC) magnetic field over a wide volume; for example, in some cases it may create an AC field in a volume of about 0.5×0.5×0.5 m.

Additional fields may be applied by further field generators to aid in tracking instruments within the body. For example, a planar field generator (PFG) may be attached to a system arm adjacent to the patient and oriented to provide an EM field at an angle. Reference sensors 513 may be placed on the patient's body to provide local EM fields to further increase tracking accuracy. Each of the reference sensors 513 may be attached by cables 514 to a command module 515. The cables 514 are connected to the command module 515 through interface units 516 which handle communications with their respective devices as well as providing power. The interface unit 516 is coupled to a system control unit (SCU) 517 which acts as an overall interface controller for the various entities mentioned above. The SCU 517 also drives the field generators (e.g., WFG 512), as well as collecting sensor data from the interface units 516, from which it calculates the position and orientation of sensors within the body. The SCU 517 may be coupled to a personal computer (PC) 518 to allow user access and control.

The command module 515 is also connected to the various IDMs 519 coupled to the surgical robotic system 500 as described herein. The IDMs 519 are typically coupled to a single surgical robotic system (e.g., the surgical robotic system 500) and are used to control and receive data from their respective connected robotic components; for example, robotic endoscope tools or robotic arms. As described above, as an example, the IDMs 519 are coupled to an endoscopic tool (not shown here) of the surgical robotic system 500.

The command module 515 receives data passed from the endoscopic tool. The type of received data depends on the corresponding type of instrument attached. For example, example received data includes sensor data (e.g., image data, EM data), robotic data (e.g., command data, force and distance data, mechanical model data, kinematic model data, etc.), control data, and/or video data. To better handle video data, a field-programmable gate array (FPGA) 520 may be configured to handle image processing. Comparing data obtained from the various sensors, devices, and field generators allows the SCU 517 to precisely track the movements of different components of the surgical robotic system 500, and for example, positions and orientations of these components.

In order to track a sensor through the patient's anatomy, the EM tracking system 505 may require a process known as "registration," where the system finds the geometric transformation that aligns a single object between different coordinate systems. For instance, a specific anatomical site on a patient has two different representations in the 3D model coordinates and in the EM sensor coordinates. To be able to establish consistency and common language between these two different coordinate systems, the EM tracking system 505 needs to find the transformation that links these two representations, i.e., registration. For example, the position of the EM tracker relative to the position of the EM field generator may be mapped to a 3D coordinate system to isolate a location in a corresponding 3D model.

V. B. 3D Model Representation

Figure 6A:
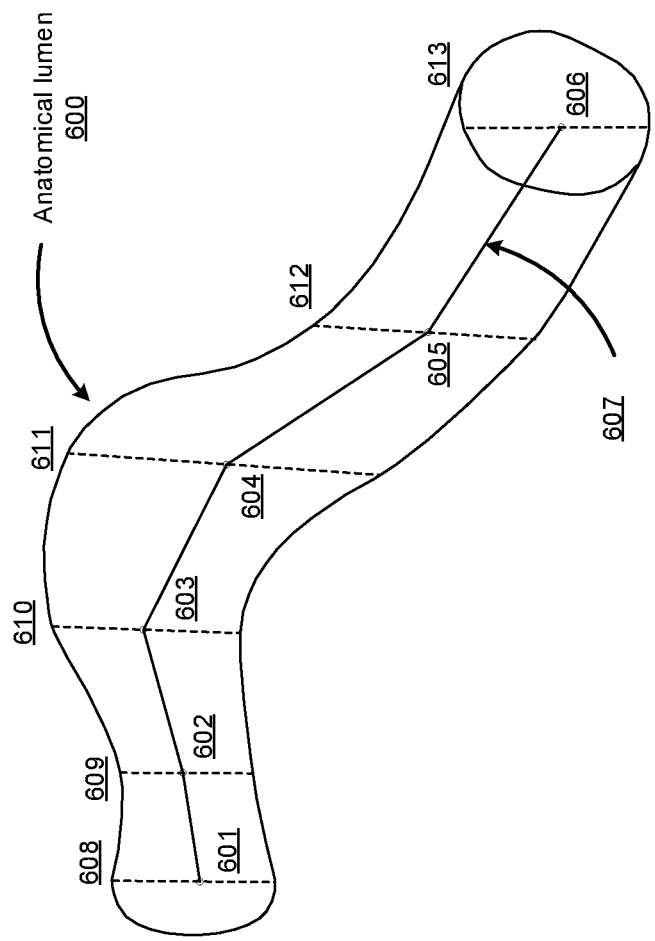
FIGS. 6A-6B show an example anatomical lumen and an example 3D model of the anatomical lumen, according to one embodiment.
Figure 6B:
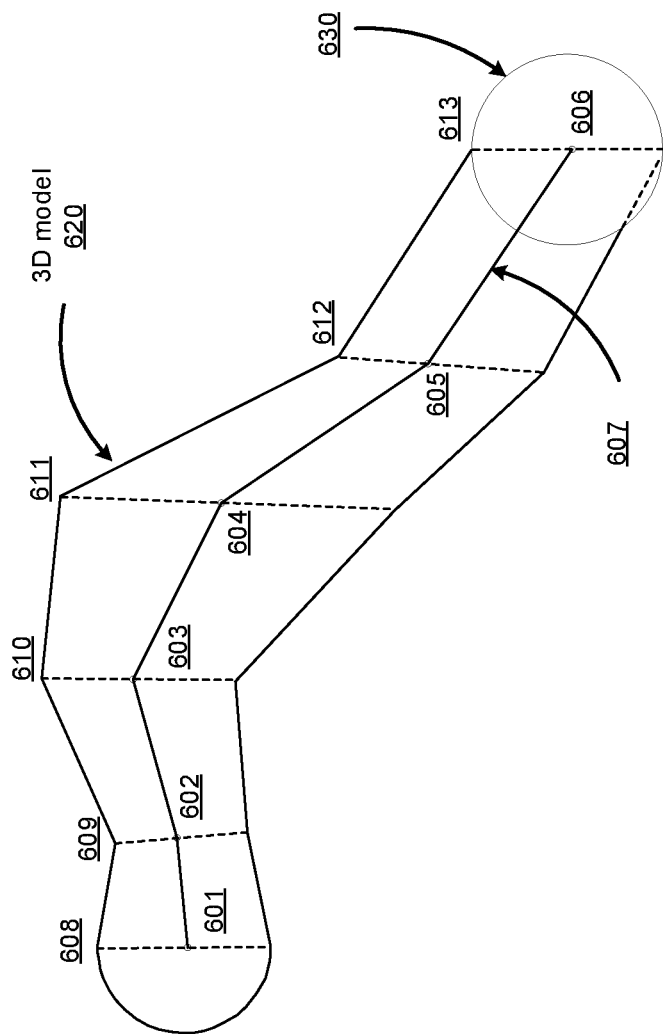

FIGS. 6A-6B show an example anatomical lumen 600 and an example 3D model 620 of the anatomical lumen, according to one embodiment. More specifically, FIGS. 6A-6B illustrate the relationships of centerline coordinates, diameter measurements and anatomical spaces between the actual anatomical lumen 600 and its 3D model 620. In FIG. 6A, the anatomical lumen 600 is roughly tracked longitudinally by centerline coordinates 601, 602, 603, 604, 605, and 606 where each centerline coordinate roughly approximates the center of the tomographic slice of the lumen. The centerline coordinates are connected and visualized by a centerline 607. The volume of the lumen can be further visualized by measuring the diameter of the lumen at each centerline coordinate, e.g., diameters 608, 609, 610, 611, 612, and 613 represent the measurements of the anatomical lumen 600 corresponding to coordinates 601, 602, 603, 604, 605, and 606.

FIG. 6B shows the example 3D model 620 of the anatomical lumen 600 shown in FIG. 6A, according to one embodiment. In FIG. 6B, the anatomical lumen 600 is visualized in 3D space by first locating the centerline coordinates 601, 602, 603, 604, 605, and 606 in 3D space based on the centerline 607. As one example, at each centerline coordinate, the lumen diameter is visualized as a 2D circular space (e.g., the 2D circular space 630) with diameters 608, 609, 610, 611, 612, and 613. By connecting those 2D circular spaces to form a 3D space, the anatomical lumen 600 is approximated and visualized as the 3D model 620. More accurate approximations may be determined by increasing the resolution of the centerline coordinates and measurements, i.e., increasing the density of centerline coordinates and measurements for a given lumen or subsection. Centerline coordinates may also include markers to indicate point of interest for the physician, including lesions.

In some embodiments, a pre-operative software package is also used to analyze and derive a navigation path based on the generated 3D model of the anatomical space. For example, the software package may derive a shortest navigation path to a single lesion (marked by a centerline coordinate) or to several lesions. This navigation path may be presented to the operator intra-operatively either in two-dimensions or three-dimensions depending on the operator's preference. In certain implementations, the navigation path (or at a portion thereof) may be pre-operatively selected by the operator. The path selection may include identification of one or more target locations (also simply referred to as a "target") within the patient's anatomy.

Figure 7:
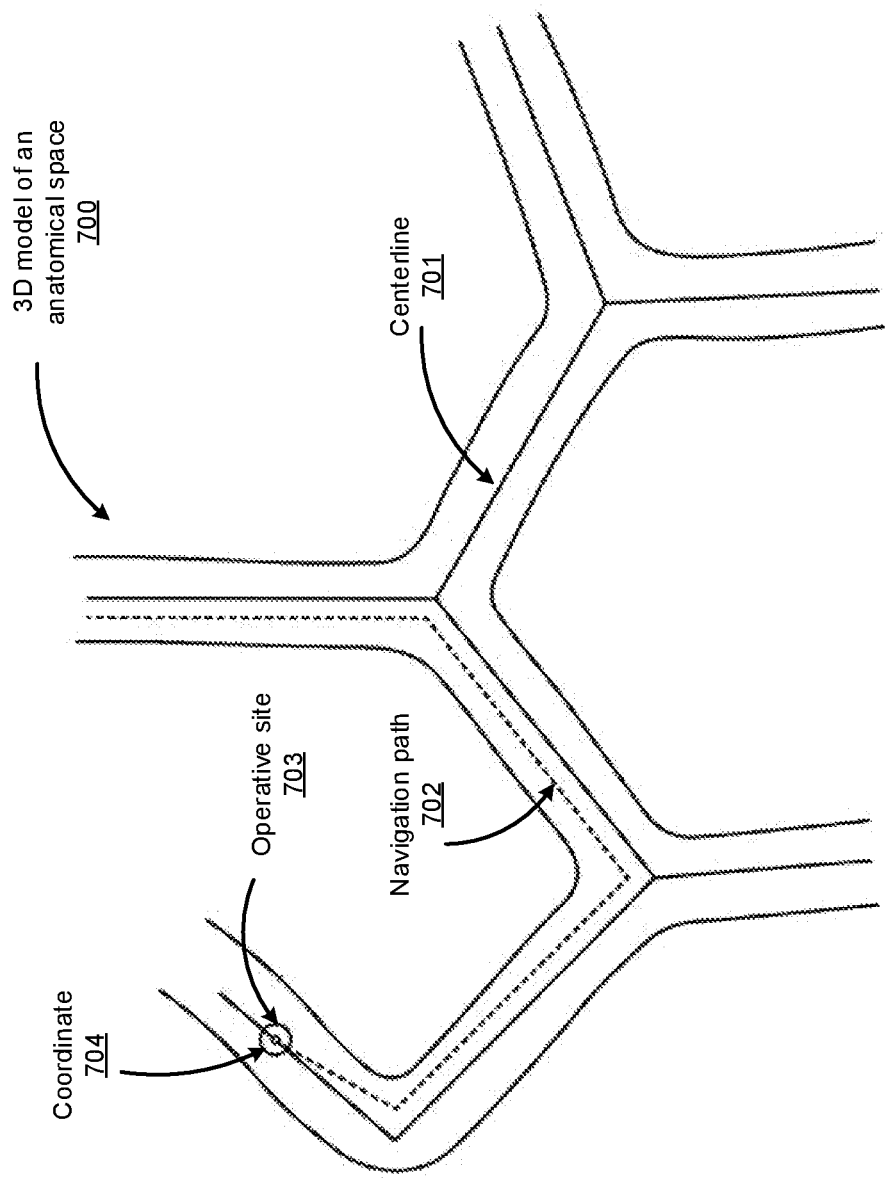
FIG. 7 shows a computer-generated 3D model representing an anatomical space, according to one embodiment.

FIG. 7 shows a computer-generated 3D model 700 representing an anatomical space, according to one embodiment. As discussed above in FIGS. 6A-6B, the 3D model 700 may be generated using a centerline 701 that was obtained by reviewing CT scans that were generated preoperatively. In some embodiments, computer software may be able to map a navigation path 702 within the tubular network to access an operative site 703 (or other target) within the 3D model 700. In some embodiments, the operative site 703 may be linked to an individual centerline coordinate 704, which allows a computer algorithm to topologically search the centerline coordinates of the 3D model 700 for the optimum path 702 within the tubular network. In certain embodiments, the topological search for the path 702 may be constrained by certain operator selected parameters, such as the location of one or more targets, one or more waypoints, etc.

In some embodiments, the distal end of the endoscopic tool within the patient's anatomy is tracked, and the tracked location of the endoscopic tool within the patient's anatomy is mapped and placed within a computer model, which enhances the navigational capabilities of the tubular network. In order to track the distal working end of the endoscopic tool, i.e., location and orientation of the working end, a number of approaches may be employed, either individually or in combination.

In a sensor-based approach to localization, a sensor, such as an EM tracker, may be coupled to the distal working end of the endoscopic tool to provide a real-time indication of the progression of the endoscopic tool. In EM-based tracking, an EM tracker, embedded in the endoscopic tool, measures the variation in the electromagnetic field created by one or more EM transmitters. The transmitters (or field generators), may be placed close to the patient (e.g., as part of the surgical bed) to create a low intensity magnetic field. This induces small-currents in sensor coils in the EM tracker, which are correlated to the distance and angle between the sensor and the generator. The electrical signal may then be digitized by an interface unit (on-chip or PCB) and sent via cables/wiring back to the system cart and then to the command module. The data may then be processed to interpret the current data and calculate the precise location and orientation of the sensor relative to the transmitters. Multiple sensors may be used at different locations in the endoscopic tool, for instance in leader and sheath in order to calculate the individual positions of those components. Accordingly, based on readings from an artificially-generated EM field, the EM tracker may detect changes in field strength as it moves through the patient's anatomy.

Figure 8A:
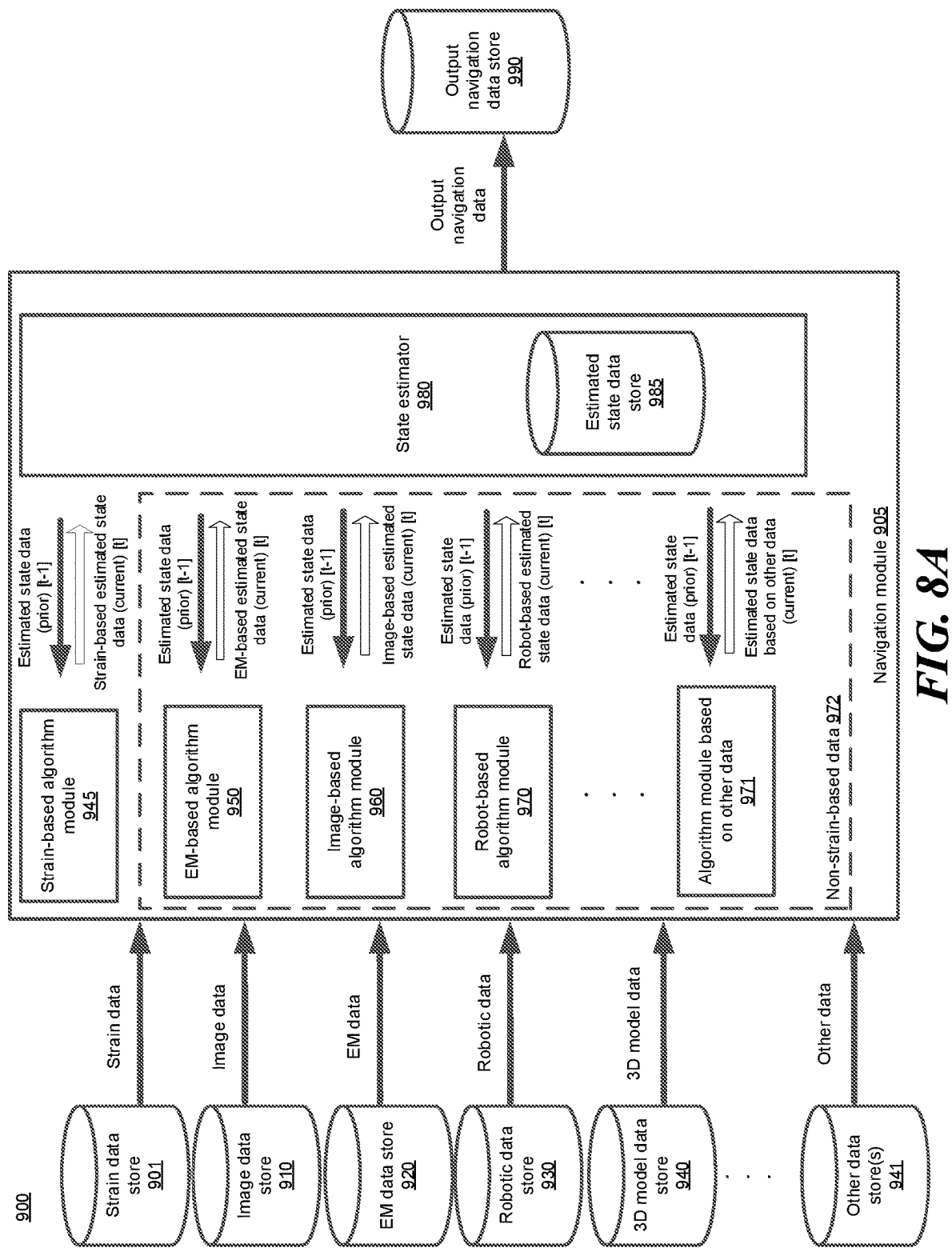
FIG. 8A shows a high-level overview of an example block diagram of a navigation configuration system, according to one embodiment.

VI. Navigation Configuration System
VI. A. High-Level Overview of Navigation Configuration System FIG. 8A shows an example block diagram of a navigation configuration system 900, according to one embodiment. In FIG. 8A, the navigation configuration system 900 includes multiple input data stores, a navigation module 905 that receives various types of input data from the multiple input data stores, and an output navigation data store 990 that receives output navigation data from the navigation module 905. The block diagram of the navigation configuration system 900 shown in FIG. 8A is merely one example, and in alternative embodiments not shown, the navigation configuration system 900 can include different and/or additional elements or not include one or more of the elements shown in FIG. 8A. Likewise, functions performed by various elements of the navigation configuration system 900 may differ according to different embodiments. The navigation configuration system 900 may be similar to the navigational system described in U.S. Pat. No. 9,727,963, issued on Aug. 8, 2017, the entirety of which is incorporated herein by reference.

The input data, as used herein, refers to raw or processed data gathered from input devices (e.g., command module, optical sensor, EM sensor, IDM) for generating estimated state information for the endoscope 118 (or other instrument) as well as output navigation data. The multiple input data stores 901-941 can include a strain data store 901, an image data store 910, an EM data store 920, a robotic data store 930, a 3D model data store 940, and other data store(s) 941. Each type of the input data stores 901-941 stores the name-indicated type of data for access and use by the navigation module 905. Strain data may include one or more measurements of strain along the endoscope 118 (e.g., generated and/or stored by the shape detector 452 of FIG. 4C).

Image data may include one or more image frames captured by the imaging device at the instrument tip, as well as information such as frame rates or timestamps that allow a determination of the time elapsed between pairs of frames.

Robotic data may include data typically used by the system for functions related to the control of the instrument (e.g., endoscope 118 and/or its sheath), and/or physical movement of the instrument or part of the instrument (e.g., the instrument tip or sheath) within the tubular network. Robotic data may allow the state of the instrument to be inferred based on the data measured while navigating the instrument within the tubular network. The kinematic and dynamic models may be generated based on a priori information gathered during a calibration stage. This a priori information can be stored on the device and read and utilized by the robot to improve the drive, control, and navigation of the instrument and to improve other types of data available to the robot (e.g., EM data, image data, strain-based shape data, etc.). The robotic data may include parameters that are specific to each instrument.

Figure 8B:
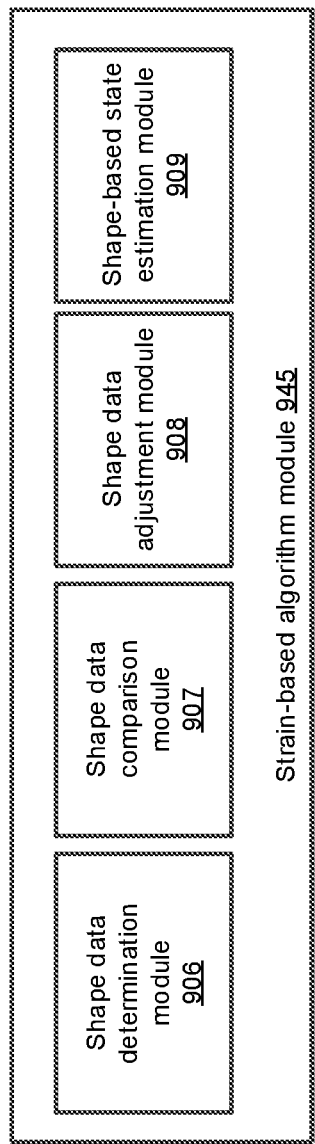
FIG. 8B shows a block diagram illustrating example modules included in the strain-based algorithm module, according to one embodiment.
Figure 8C:
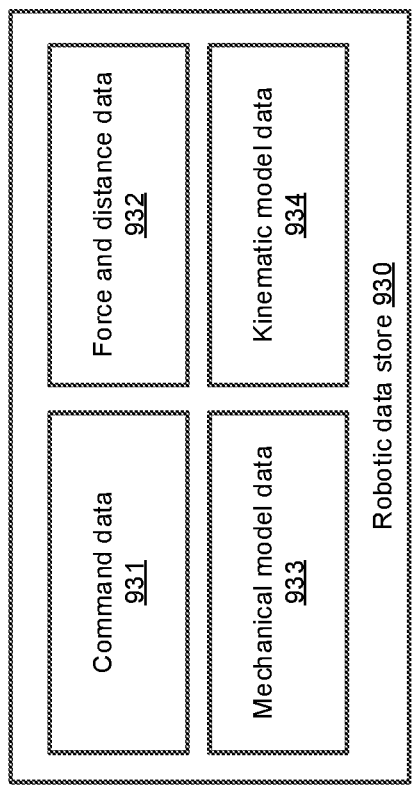
FIG. 8C shows a block diagram illustrating examples of robotic data stored in the robotic data store, according to one embodiment.

FIG. 8C illustrates examples of the robotic data that may be stored in the robotic data store 930 of FIG. 8A. As shown in FIG. 8C, the robotic data may include command data 931 instructing the instrument tip to reach a specific anatomical site and/or change its orientation (e.g., articulation data instructing the instrument to exhibit a desired articulation with a specific pitch, roll, and yaw, insertion and retraction data instructing the insertion and retraction for one or both of a leader and a sheath, etc.) force and distance data 932 (e.g., the distances that the pull wires have been actuated since the device was loaded on the robot, the amount of force being applied to the pull wires as measured by the torque sensors in the IDM, the amount of insertion force exerted by the robot arm to insert or retract the instruments, etc.), mechanical model data 933 representing mechanical movement of an elongate member of the instrument (e.g. motion of one or more pull wires, tendons, or shafts of the endoscope that drive the actual movement of the medical instrument within the tubular network, kinematic model data 934 representing the motion and shape of an instrument (e.g., geometric parameters indicative of a position of the instrument, and/or any changes to the geometric parameters relative to a pre-determined or reference position or set of coordinates), and the like.

EM data may be collected by one or more EM sensors (e.g., located proximal to a tip of the instrument) and/or the EM tracking system as described above. 3D model data may be derived from, among other things, 2D CT scans as described above.

The output navigation data store 990 receives and stores output navigation data provided by the navigation module 905. Output navigation data indicates information to assist in directing the instrument through a patient's anatomy and in one example through a tubular network to arrive at a particular destination within the tubular network, and is based on estimated state information for the instrument at each instant time. The estimated state information can include the location and orientation of the instrument within the tubular network. In one embodiment, as the instrument moves inside the tubular network, the output navigation data indicating updates of movement and location/orientation information of the instrument is provided in real time, which better assists its navigation through the tubular network.

To determine the output navigation data, the navigation module 905 locates (or determines) the estimated state of the instrument within the tubular network. As shown in FIG. 8A, the navigation module 905 further includes various algorithm modules, such as a strain-based algorithm module 945, an EM-based algorithm module 950, an image-based algorithm module 960, a robot-based algorithm module 970, an algorithm module 971 based on other data, etc. These modules may each consume mainly certain types of input data and contribute a different type of data to a state estimator 980. As illustrated in FIG. 8A, the different kinds of data output by these modules, (labeled strain-based estimated state data, EM-based estimated state data, the image-based estimated state data, and the robot-based estimated state data, and estimated state data based on other data) may be generally referred to as "intermediate data" for the sake of explanation. In some cases, the navigation module 905 determines, based on the estimated state of the instrument, that a damage to the instrument or a malfunction is imminent (e.g., buckling, prolapse, etc.). In such cases, the navigation module 905 may cause the instrument to be controlled in a way to avoid the damage or malfunction. The detailed composition of each algorithm module and the state estimator 980 is described in greater detail below.

VI. B. Navigation Module
VI. B. 1. State Estimator

As introduced above, the navigation module 905 further includes a state estimator 980 as well as multiple algorithm modules that employ different algorithms for navigating through a tubular network. For clarity of description, the state estimator 980 is described first, followed by the description of the various modules that exchange data with the state estimator 980.

The state estimator 980 included in the navigation module 905 receives various intermediate data and provides the estimated state of the instrument tip (or other portions of the instrument) as a function of time, where the estimated state indicates the estimated location and orientation information of the instrument tip (or other portions of the instrument) within the tubular network. The estimated state data are stored in the estimated state data store 985 that is included in the state estimator 980. While the description herein is described within the context of determining the estimated location and orientation information of the instrument tip (or other portions of the instrument) within a tubular network, in other arrangements, the information can be used to determine estimated location and orientation information of the instrument tip (or other portions of the instrument) with respect to the patient, in general.

VI. B. 2. Estimated State Data Store

The estimated state data store 985 may include a bifurcation data store, a position data store, a depth data store, and an orientation data store. However this particular breakdown of data storage is merely one example, and in alternative embodiments not shown, different and/or additional data stores can be included in the estimated state data store 985.

The various stores introduced above represent estimated state data in a variety of ways. Bifurcation data may refer to the location of the instrument with respect to the set of branches (e.g., bifurcation, trifurcation or a division into more than three branches) within the tubular network. For example, the bifurcation data can be set of branch choices elected by the instrument as it traverses through the tubular network, based on a larger set of available branches as provided, for example, by the 3D model which maps the entirety of the tubular network. The bifurcation data can further include information in front of the location of the instrument tip, such as branches (bifurcations) that the instrument tip is near but has not yet traversed through, but which may have been detected, for example, based on the tip's current position information relative to the 3D model, or based on images captured of the upcoming bifurcations.

Position data may indicate three-dimensional position of some part of the instrument within the tubular network or some part of the tubular network itself. Position data can be in the form of absolute locations or relative locations relative to, for example, the 3D model of the tubular network. As one example, position data can include an indication of the position of the location of the instrument being within a specific branch. The identification of the specific branch may also be stored as a segment identification (ID) which uniquely identifies the specific segment of the model in which the instrument tip is located.

Depth data may indicate depth information of the instrument tip within the tubular network. Example depth data includes the total insertion (absolute) depth of the instrument into the patient as well as the (relative) depth within an identified branch (e.g., the segment identified by the position data store 1087). Depth data may be determined based on position data regarding both the tubular network and instrument.

Orientation data may indicate orientation information of the instrument tip, and may include overall roll, pitch, and yaw in relation to the 3D model as well as pitch, roll, yaw within an identified branch.

VI. B. 3. Data Output to Algorithm Modules

As illustrated in FIG. 8A, the state estimator 980 provides the estimated state data back to the algorithm modules for generating more accurate intermediate data, which the state estimator uses to generate improved and/or updated estimated states, and so on forming a feedback loop. The state estimator 980 receives estimated state data from one or more algorithm modules shown in FIG. 8A. The state estimator 980 uses this data to generate "estimated state data (prior)" that is associated with timestamp "t−1." The state estimator 980 then provides the data to one or more (which can be a different combination of algorithm modules than the one from which estimated state data was received previously) of the algorithm modules. The "estimated state data (prior)" may be based on a combination of different types of intermediate data (e.g., image data, mechanical model data, command data, kinematic model data, and the like) that is associated with timestamp "t−1" as generated and received from different algorithm modules. For example, estimated state data based on a combination of the non-strain-based data 972 may be provided to the strain-based algorithm module 945, and the strain-based algorithm module 945 may determine and output strain-based estimated state data to the state estimator 980.

Next, the one or more of the algorithm modules run their respective algorithms using the received estimated state data (prior) to output to the state estimator 980 improved and updated estimated state data, which is represented by "estimated state data (current)" shown for the respective algorithm modules and associated with timestamp "t." This process can be repeated for future timestamps to generate estimated state data.

As the state estimator 980 may use several different kinds of intermediate data to arrive at its estimates of the state of the instrument within the tubular network, the state estimator 980 is configured to account for the various different kinds of errors and uncertainty in both measurement and analysis that each type of underlying data (robotic, EM, image) and each type of algorithm module may create or carry through into the intermediate data used for consideration in determining the estimated state. To address these, two concepts are discussed, that of a probability distribution and that of confidence value.

The term "probability" in the phrase "probability distribution", as used herein, refers to a likelihood of an estimation of a possible location and/or orientation of the instrument being correct. For example, different probabilities may be calculated by one of the algorithm modules indicating the relative likelihood that the instrument is in one of several different possible branches within the tubular network. In one embodiment, the type of probability distribution (e.g., discrete distribution or continuous distribution) is chosen to match features of an estimated state (e.g., type of the estimated state, for example continuous position information vs. discrete branch choice). As one example, estimated states for identifying which segment the instrument is in for a trifurcation may be represented by a discrete probability distribution, and may include three discrete values of 20%, 30% and 50% representing chance as being in the location inside each of the three branches as determined by one of the algorithm modules. As another example, the estimated state may include a roll angle of the instrument of 40±5 degrees and a segment depth of the instrument tip within a branch may be is 4±1 mm, each represented by a Gaussian distribution which is a type of continuous probability distribution. Different methods or modalities can be used to generate the probabilities, which will vary by algorithm module as more fully described below with reference to later figures.

In contrast, the "confidence value," as used herein, reflects a measure of confidence in the estimation of the state provided by one of the algorithms based one or more factors. For strain-based algorithms using shape-sensing fibers, factors such as temperature, proximity to the proximal end of the catheter, and the like may affect the confidence in estimation of the state. For example, thermal expansion and contraction of the optical fiber portions may erroneously indicate that the instrument is bending. Further, in some embodiments, strain measurements of distal portions of the instrument rely on shape/position data determined based on strain measurements of proximal portions of the instrument (e.g., closer to the shape detector 452), and any errors in the strain measurements of proximal portions may be magnified in the strain measurements of distal portions. For the EM-based algorithms, factors such as distortion to EM field, inaccuracy in EM registration, shift or movement of the patient, and respiration of the patient may affect the confidence in estimation of the state. Particularly, the confidence value in estimation of the state provided by the EM-based algorithms may depend on the respiration cycle of the patient, movement of the patient or the EM field generators, and the location within the anatomy where the instrument tip locates. For the image-based algorithms, examples factors that may affect the confidence value in estimation of the state include illumination condition for the location within the anatomy where the images are captured, presence of fluid, tissue, or other obstructions against or in front of the optical sensor capturing the images, respiration of the patient, condition of the tubular network of the patient itself (e.g., lung) such as the general fluid inside the tubular network and occlusion of the tubular network, and specific operating techniques used in, e.g., navigating or image capturing.

For example one factor may be that a particular algorithm has differing levels of accuracy at different depths in a patient's lungs, such that relatively close to the airway opening, a particular algorithm may have a high confidence in its estimations of instrument location and orientation, but the further into the bottom of the lung the instrument travels that confidence value may drop. Generally, the confidence value is based on one or more systemic factors relating to the process by which a result is determined, whereas probability is a relative measure that arises when trying to determine the correct result from multiple possibilities with a single algorithm based on underlying data.

As one example, a mathematical equation for calculating results of an estimated state represented by a discrete probability distribution (e.g., branch/segment identification for a trifurcation with three values of an estimated state involved) can be as follows:

$$S_1 = C_{EM} * P_{1,EM} + C_{Image} * P_{1,Image} + C_{Robot} * P_{1,Robot};$$

$$S_2 = C_{EM} * P_{2,EM} + C_{Image} * P_{2,Image} + C_{Robot} * P_{2,Robot};$$

$$S_3 = C_{EM} * P_{3,EM} + C_{Image} * P_{3,Image} + C_{Robot} * P_{3,Robot}.$$

In the example mathematical equation above, $S_i$ (i=1,2,3) represents possible example values of an estimated state in a case where 3 possible segments are identified or present in the 3D model, $C_{EM}$, $C_{Image}$, and $C_{Robot}$ represents confidence value corresponding to EM-based algorithm, image-based algorithm, and robot-based algorithm and $P_{i,EM}$, $P_{i,Image}$, and $P_{i,Robot}$ represent the probabilities for segment i.

To better illustrate the concepts of probability distributions and confidence value associated with estimate states, a detailed example is provided here. In this example, a user is trying to identify segment where an instrument tip is located in a certain trifurcation within a central airway (the predicted region) of the tubular network, and three algorithms modules are used including EM-based algorithm, image-based algorithm, and robot-based algorithm. In this example, a probability distribution corresponding to the EM-based algorithm may be 20% in the first branch, 30% in the second branch, and 50% in the third (last) branch, and the confidence value applied to this EM-based algorithm and the central airway is 80%. For the same example, a probability distribution corresponding to the image-based algorithm may be 40%, 20%, 40% for the first, second, and third branch, and the confidence value applied to this image-based algorithm is 30%; while a probability distribution corresponding to the robot-based algorithm may be 10%, 60%, 30% for the first, second, and third branch, and the confidence value applied to this image-based algorithm is 20%.

The difference of confidence values applied to the EM-based algorithm and the image-based algorithm indicates that the EM-based algorithm may be a better choice for segment identification in the central airway, compared with the image-based algorithm. An example mathematical calculation of a final estimated state can be: for the first branch: 20%*80%+40%*30%+10%*20%=30%; for the second branch: 30%*80%+20%*30%+60%*20%=42%; and for the third branch: 50%*80%+40%*30%+30%*20%=58%.

In this example, the output estimated state for the instrument tip can be the result values (e.g., the resulting 30%, 42%, and 58%), or derivative value from these result values such as the determination that the instrument tip is in the third branch.

As above the estimated state may be represented in a number of different ways. For example, the estimated state may further include an absolute depth from airway to location of the tip of the instrument, as well as a set of data representing the set of branches traversed by the instrument within the tubular network, the set being a subset of the entire set of branches provided by the 3D model of the patient's lungs, for example. The application of probability distribution and confidence value on estimated states allows improved accuracy of estimation of location and/or orientation of the instrument tip within the tubular network.

VI. B. 4. Strain-Based Algorithm Module
VI. B. 4. i. Elements of Strain-Based Algorithm Module The strain-based algorithm module 945 uses strain data to determine the estimated state of the instrument within the tubular network. FIGS. 8B and 9-11 illustrate the modules that may be included in the strain-based algorithm module 945. As illustrated in FIG. 8B, the strain-based algorithm module 945 may include (i) shape data determination module 906 for determining the shape data based on strain data, (ii) shape data comparison module 907 for comparing the shape data to robotic data, (iii) shape data adjustment module 908 for adjusting the shape data (or the confidence in the shape data) based on the comparison between the shape data and the robotic data, and (iv) shape-based state estimation module 909 for determining shape-based estimated state data based on the adjusted shape data (or adjusted confidence in the shape data). Although illustrated as separate components, the modules 906-909 may be implemented as one or more hardware components (e.g., a single component, individual components, or any number of components), one or more software components (e.g., a single component, individual components, or any number of components), or any combination thereof. The modules 906-909 are described in greater detail below with reference to FIGS. 9-11.

VI. B. 4. ii. Determining Shape Data

Figure 9:
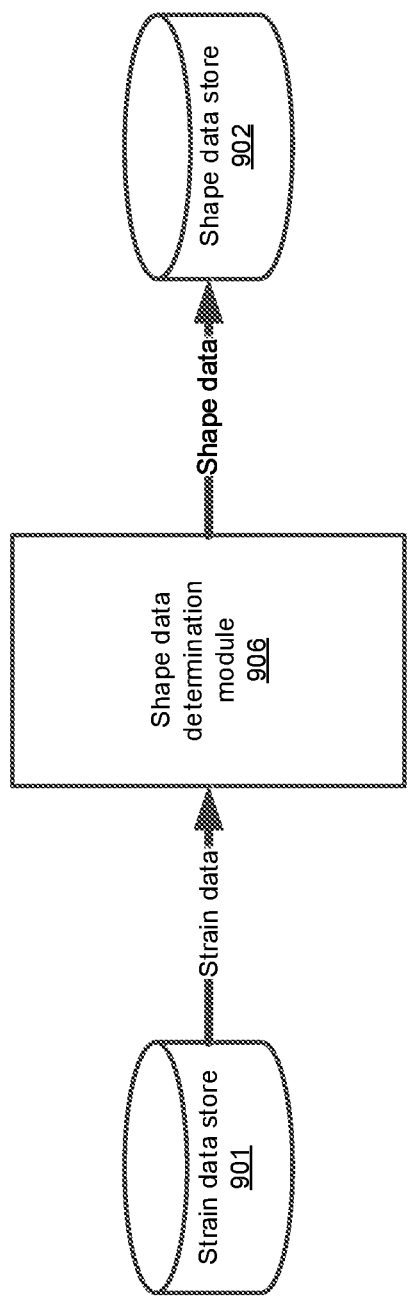
FIG. 9 shows an example block diagram of a shape data determination module, according to one embodiment.

FIG. 9 shows an example shape data determination module that may be included in the strain-based algorithm module 945. As shown in FIG. 9, the shape data determination module 906 receives strain data from the strain data store 901 and outputs shape data to shape data store 902. The shape data determination module 906 may determine the shape data based on the strain data received from the strain data store 901. As discussed with reference to FIG. 8A, the strain data may include one or more measurements of strain along the one or more optical fibers 456 (or one or more cores therein) that are generated and/or stored by the shape detector 452 of FIG. 4C. The shape data may include angles, coordinates, or a combination thereof indicative of the current shape of the instrument. In some cases, the shape data may include curvature information (e.g., curvature value of one or more portion of the instrument), orientation information (e.g., roll, pitch, and/or yaw of one or more portions of the instrument), position information (e.g., position of one or more portions of the instrument in a reference coordinate system, which is, for example, used by the system to navigate the instrument), and/or other information that can be used to indicate the shape of the instrument.

VI. B. 4. iii. Improving Shape Data Using Robotic Data

Figure 10:
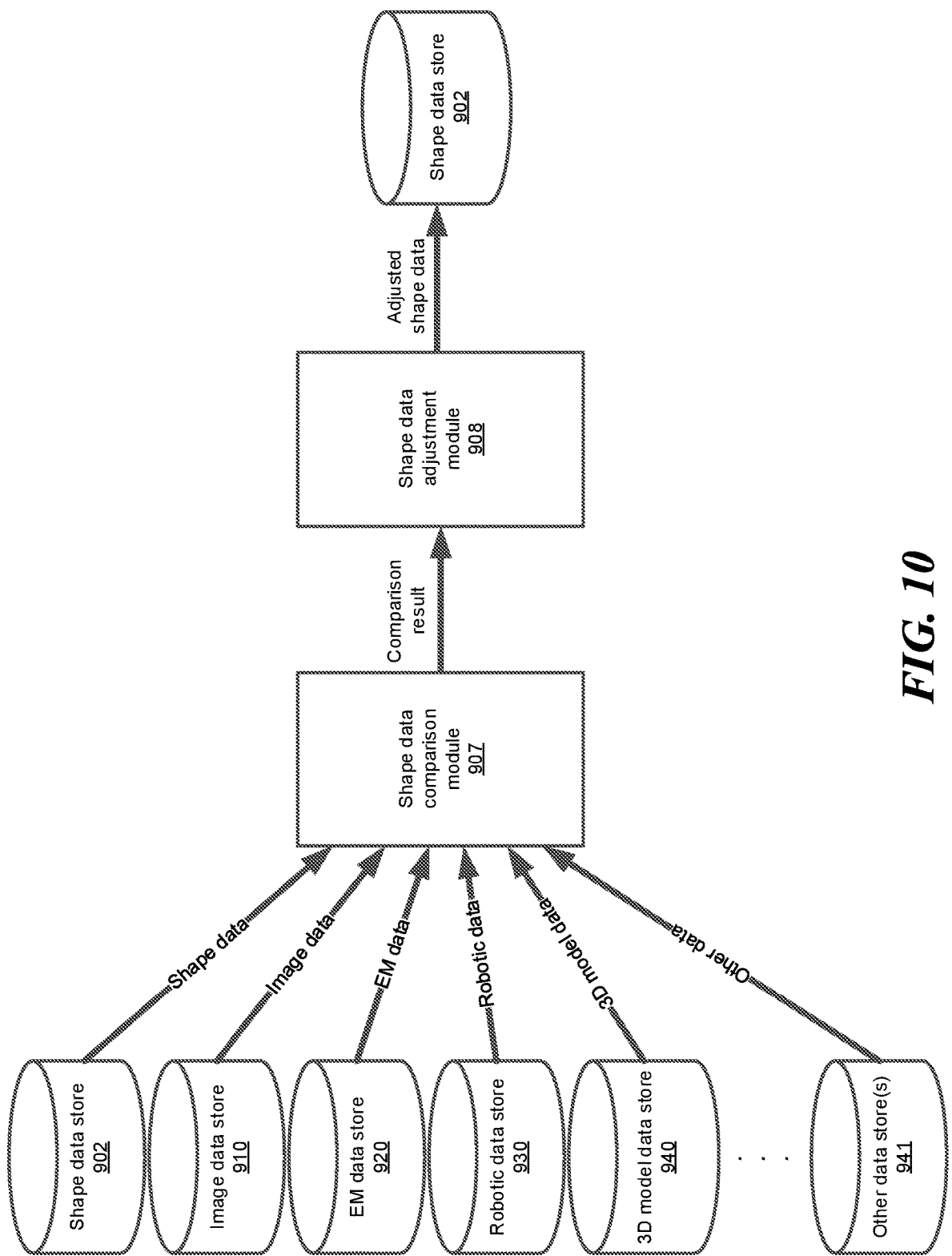
FIG. 10 shows an example block diagram of a shape data comparison module and a shape data adjustment module, according to one embodiment.

FIG. 10 shows an example shape data comparison module and shape data adjustment module that may be included in the strain-based algorithm module 945. As shown in FIG. 10, the shape data comparison module 907 receives data from a plurality of data stores 902-941. For example, the received data can include shape data from the shape data store 902 and robotic data from the robotic data store 930. The shape data comparison module 907 may compare the received shape data to the received robotic data and determine whether the received shape data is consistent with the received robotic data.

As described herein, the robotic data may include, as one example, kinematic model data that indicates the movement of the instrument expected to result from a given set of control commands. The shape data comparison module 907 may compare the movement indicated by the robotic data with the movement indicated by the shape data received from the shape data determination module 906. Based on the comparison, the shape data comparison module 907 may output a comparison result that indicates whether or not the shape data is consistent with the robotic data and the extent of the difference between the shape data and the robotic data. For example, the comparison result may indicate that the curvature of the instrument indicated by the shape data is outside the range of acceptable curvature indicated by the robotic data (e.g., exceeds the highest acceptable curvature by a specific amount). As another example, the comparison result may indicate that the shape data corresponding to a specific portion of the instrument is not consistent with the torque measurements included in the robotic data (e.g., measurements of the torque applied to the pull wires).

VI. B. 4. iv. Improving Shape Data Using Data Other than Robotic Data

In other embodiments, the shape data comparison module 907 can compare the shape data to the image data received from the image data store 910, the shape data to the EM data received from the EM data store 920, the shape data to the 3D model data received from the 3D model data store 940, the shape data to other data received from other data store(s) 941, and/or any combination of data received from two or more of the data stores 910-941.

For example, the shape data comparison module 907 may determine, based on the image data received from the image data store 910, an expected orientation of the instrument (e.g., at or near the distal end of the instrument). The shape data comparison module 907 may then determine whether the shape data is inconsistent with the expected orientation of the instrument (e.g., the image data indicates that the tip of the instrument is pointing in a direction parallel to the anatomical lumen, but the shape data indicates that the tip of the instrument is pointing at an inner wall of the anatomical lumen).

In another example, the shape data comparison module 907 may determine, based on the 3D model data received from the 3D model data store 940, that the anatomical lumen in which the instrument is located has a range of possible coordinate values. The shape data comparison module 907 may then determine whether the shape data indicates that the instrument is located outside the range of possible coordinate values or whether the shape data indicates that the instrument is shaped in a way that would not fit in the anatomical lumen.

In yet another example, the shape data comparison module 907 may determine, based on the EM data received from the EM data store 920, a set of coordinate values corresponding to the current location of the instrument in a reference coordinate system. The shape data comparison module 907 may then determine whether the shape data is inconsistent with the expected orientation of the instrument (e.g., the set of coordinate values indicated by the shape data is different from the set of coordinate values indicated by the EM data, or deviates from the set of coordinate values indicated by the EM data by more than a threshold amount).

In yet another example, fluoroscopy (X-ray) images can be analyzed by a computer vision algorithm to extract the silhouette of the instrument, and the shape data comparison module 907 may then determine whether the shape data is inconsistent with the extracted silhouette of the instrument.

In yet another example, different sensing modalities can be fit into the working channel 438 and may be connected to work with the system. These sensing modalities include radial endobronchial ultrasound (REBUS) probes, multi-spectral imaging (spectroscopes), tomography imaging (optical coherence tomography, confocal microscopy, two-photon excitation microscopy, etc.). Using the sensor data generated by these sensing modalities, the shape data comparison module 907 can determine whether the shape data is inconsistent with the sensor data.

VI. B. 4. v. Other Examples of Shape Data Comparison

In some embodiments, the shape data comparison module 907 determines that a mismatch between the shape data and the robotic data has been detected for over a threshold amount of time, and outputs an alert indicating that the instrument may be damaged. For example, the shape data comparison module 907 may determine that the last five comparison results output to the shape data adjustment module 908 indicated that the shape data was inconsistent with the robotic data, and output an alert (e.g., indicating that the instrument may be damaged, stuck, or otherwise malfunctioning).

Although not illustrated in FIG. 10, the shape data comparison module 907 can, additionally or alternatively, compare the shape data to the estimated state data received from the state estimator 980. In some cases, the shape of the sheath may be known (e.g., based on shape-sensing using optical fibers inside the sheath, or robotic data corresponding to the sheath). In such cases, the shape data comparison module 907 may access the shape data corresponding to the sheath surrounding the instrument, and compare the shape data of the instrument to the shape data of the sheath.

In some cases, the shape data comparison module 907 determines that the robotic data has a higher confidence value than the shape data, and based on the determination, compares the shape data to the robotic data. Alternatively, in some cases, the shape data comparison module 907 determines that robotic data has a lower confidence value than the shape data, and based on the determination, refrains from comparing the shape data to the robotic data.

For example, at or near the distal end of the instrument, the confidence value assigned to the shape data or strain data may be lower than those assigned to the robotic data, because as discussed above, strain measurements of distal portions of the instrument may rely on shape/position data determined based on strain measurements of proximal portions of the instrument (e.g., closer to the shape detector 452), and any errors in the strain measurements of proximal portions may be magnified in the strain measurements of distal portions. On the other hand, at or near the proximal end of the instrument, the confidence value assigned to the shape data or strain data may be higher than those assigned to the robotic data.

In some embodiments, the shape data is compared to the robotic data at or near the distal end of the instrument and adjusted as needed, but the shape data is not compared to the robotic data at or near the proximal end of the instrument. In other embodiments, the shape data is compared to the robotic data at or near both the distal end and the proximal end of the instrument and adjusted as needed.

VI. B. 4. vi. Adjusting Shape Data Using Comparison Result

The shape data comparison module 907 outputs the result of the comparison to the shape data adjustment module 908. The result of the comparison may indicate which portion of the shape data, if any, does not satisfy one or more conditions indicated by the data to which the shape data is compared (e.g., the robotic data). For example, as discussed with reference to FIG. 4D, the comparison result may indicate that the shape data corresponding to a portion of the endoscope 118 indicates that the portion exhibits a curvature value that is not consistent with the robotic data. In another example, as discussed with reference to FIG. 4E, the comparison result may indicate that the shape data corresponding to a portion of the endoscope 118 indicates that the portion is moving at a speed that is not consistent with the robotic data.

In other cases, the comparison result may indicate that the direction of the instrument tip indicated by the shape data deviates from the direction of the instrument tip indicated by the robotic data by more than a threshold amount, that the shape data indicates that the shape of the instrument is such that a portion of the instrument would be outside the anatomical lumen, or that the location of the instrument indicated by the shape data deviates from the location of the instrument indicated by the robotic data by more than a threshold amount. The comparison result may indicate any error or deviation from what the system expects based on one or more of the data from various sources and/or estimated states from the state estimator 980.

Based on the received comparison result, the shape data adjustment module 908 adjusts the shape data and outputs the adjusted shape data to the shape data store 902. For example, upon determining that the curvature value indicated by the shape data is not consistent with the robotic data, the shape data adjustment module 908 may modify the shape data such that the curvature value is within the acceptable curvature range indicated by the robotic data. As another example, upon determining that the current speed indicated by the shape data is not consistent with the robotic data, the shape data adjustment module 908 may modify the shape data such that the current speed is within the acceptable speed range indicated by the robotic data. In yet another example, upon determining that a portion or all of the shape data does not satisfy one or more conditions indicated by the robotic data, the shape data adjustment module 908 may, instead of adjusting the shape data, discard such shape data. In yet another example, upon determining that a portion or all of the shape data does not satisfy one or more conditions indicated by the robotic data, the shape data adjustment module 908 may, instead of adjusting the shape data, reduce the confidence in the shape data (e.g., by decreasing the confidence value associated with the shape data). The adjusted shape data is stored in the shape data store 902. In some cases, the adjusted shape data is stored in another data store different from the shape data store 902.

In some cases, the shape data adjustment module 908 may make alternative or additional adjustments based on other factors. For example, the shape data adjustment module 908 may adjust the shape data (or adjust the confidence in the shape data) based on a change in temperature. In such an example, the shape data adjustment module 908 may adjust the shape data (or adjust the confidence in the shape data) based on thermal expansion and contraction properties of the optical fibers. The shape data adjustment module 908 may make such an adjustment in response to determining that the received comparison result indicates that the shape data is at odds with at least one other data. In other cases, the shape data determination module 906 takes the current temperature into account when determining the shape data based on the received strain data, and the shape data adjustment module 908 does not make additional temperature-based adjustments to the shape data.

In some embodiments, the shape data adjustment module 908 may adjust the shape data (or adjust the confidence in the shape data) based on whether the tip of the instrument is being articulated or not. Alternatively or additionally, the shape data adjustment module 908 may adjust the shape data (or adjust the confidence in the shape data) based on whether non-shape-changing strain (e.g., temperature, articulation mode, etc.) is being applied to the instrument. The shape data adjustment module 908 may make one or both of these adjustments in response to determining that the received comparison result indicates that the shape data is at odds with at least one other data.

Figure 11:
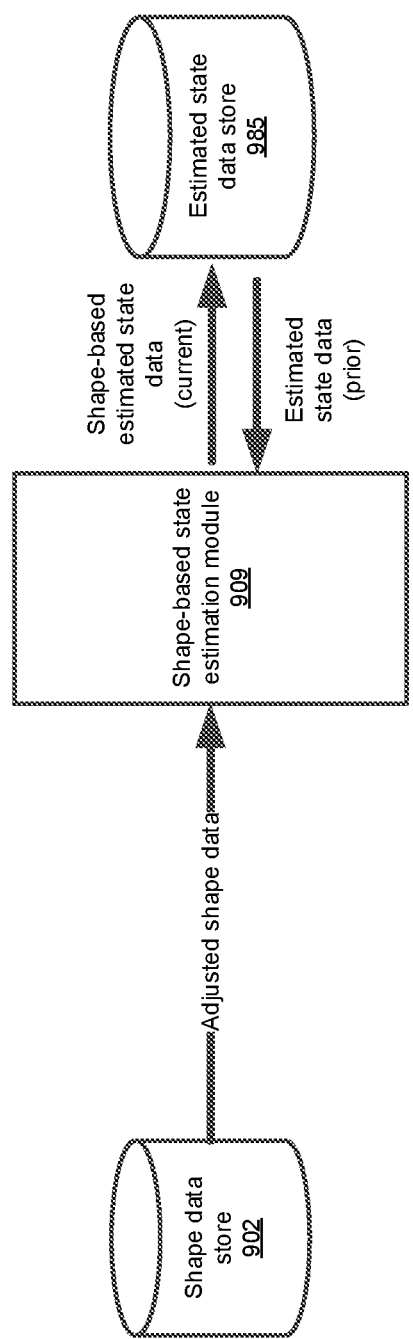
FIG. 11 shows an example block diagram of a shape-based state estimation module, according to one embodiment.

FIG. 11 shows an example shape-based state estimation module that may be included in the strain-based algorithm module 945. As shown in FIG. 11, the shape-based state estimation module 909 receives the adjusted shape data from the shape data store 902 and determines shape-based estimated state data based on the adjusted shape data and prior estimated state data received from the estimated state data store 985. The shape-based state estimation module 909 outputs the shape-based estimated state data to the estimated state data store 985. This process can be repeated to generate estimated state data for future timestamps. In some cases, the shape-based state estimation module 909 determines an estimated state of a sheath covering the instrument based on the estimated state of the instrument.

VII. A. Overview of Shape Data Adjustment Based on Robotic Data

Figure 12:
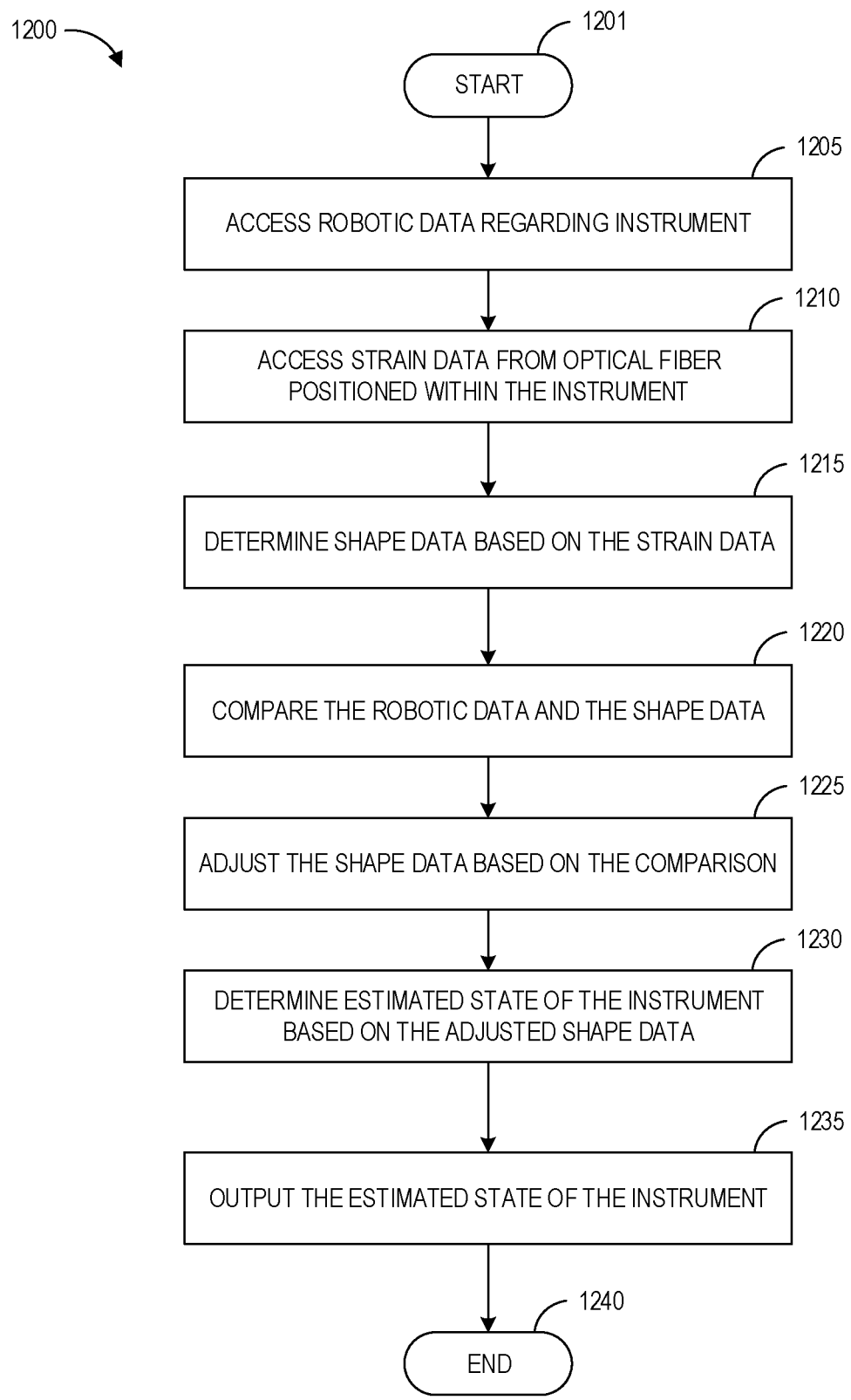
FIG. 12 shows a flowchart illustrating an example method operable by a surgical robotic system, or component(s) thereof, for determining and adjusting shape data, according to one embodiment.

FIG. 12 is a flowchart illustrating an example method operable by a surgical robotic system, or component(s) thereof, for determining and adjusting shape data based on other data available to the surgical robotic system, such as robotic data, according to one embodiment. For example, the steps of method 1200 illustrated in FIG. 12 may be performed by processor(s) and/or other component(s) of a medical robotic system (e.g., surgical robotic system 500) or associated system(s) (e.g., the strain-based algorithm module 945 of the navigation configuration system 900). For convenience, the method 1200 is described as performed by the surgical robotic system, also referred to simply as the "system" in connection with the description of the method 1200.

The method 1200 begins at block 1201. At block 1205, the system accesses robotic data regarding an instrument navigated (or to be navigated) within an interior region of a body. The robotic data can include data related to the control of the instrument (e.g., endoscope 118 and/or its sheath), and/or physical movement of the instrument or part of the instrument (e.g., the instrument tip or sheath) within the tubular network. As described above, the robotic data can include command data, force and distance data, mechanical model data, kinematic model data, and the like.

At block 1210, the system accesses strain data from an optical fiber positioned within the instrument. The strain data may be indicative of a strain on a portion of the instrument positioned within the interior region of the body. In some cases, the strain data indicates one or both of a strain on the distal end of the instrument and a strain on the proximal end of the instrument. The strain data may be generated by the shape detector 452 and stored in the strain data store 901, and the system may access the strain data from the strain data store 901.

At block 1215, the system determines shape data based on the strain data. For example, based on the strain on a specific portion of the instrument indicated by the strain data, the system may predict the shape of the specific portion of the instrument. The shape data may include angles, coordinates, or a combination thereof indicative of the current shape of the instrument. In some cases, the shape data may include curvature information (e.g., curvature value of one or more portion of the instrument), orientation information (e.g., roll, pitch, and/or yaw of one or more portions of the instrument), position information (e.g., position of one or more portions of the instrument in a reference coordinate system, which is, for example, used by the system to navigate the instrument), and/or other information that can be used to indicate the shape of the instrument.

At block 1220, the system compares the robotic data and the shape data. In some embodiments, the comparison includes determining whether a specific value included in the shape data satisfies a corresponding condition indicated by the robotic data. For example, the robotic data accessed by the system may indicate that the instrument is not capable of being controlled in a way that results in a curvature value greater than a maximum curvature value or outside a given range of curvature values. In such an example, the system may determine whether the curvature value of a given portion of the instrument indicated by the shape data exceeds the maximum curvature value or is outside the given range of curvature values indicated by the robotic data for the given portion of the instrument. In another example, the robotic data accessed by the system may indicate that the instrument is not capable of being moved faster than a maximum speed or outside a specific movement range. In such an example, the system may determine whether the movement (e.g., speed, movement path, or other time history data) of a given portion of the instrument indicated by the shape data satisfies a movement condition (e.g., maximum speed, movement speed range, etc.) indicated by the robotic data for the given portion of the instrument. A similar technique can be applied in other cases such that the system can determine whether any parameter value indicated by the shape data satisfies a corresponding shape condition (e.g., minimum, maximum, and/or range values that can indicate whether a given parameter value in the shape data is or is likely to be erroneous) indicated by the robotic data.

At block 1225, the system adjusts the shape data based on the comparison of the robotic data and the shape data. In some embodiments, the adjustment includes modifying at least a portion of the shape data such that the determination of the estimated state of the instrument (at block 1230) is based on the modified portion of the shape data. For example, upon determining that the curvature value indicated by the shape data exceeds the maximum curvature value indicated by the robotic data, the system may modify the shape data such that the curvature value is less than or equal to the maximum curvature value indicated by the robotic data. As another example, upon determining that the current speed indicated by the shape data exceeds the maximum speed indicated by the robotic data, the system may modify the shape data such that the current speed is less than or equal to the maximum speed indicated by the robotic data. In other embodiments, the adjustment includes removing at least a portion of the shape data such that the determination of the estimated state of the instrument (at block 1230) is not based on the removed portion of the shape data. For example, upon determining that a portion or all of the shape data does not satisfy one or more conditions indicated by the robotic data, the system may discard such shape data or disregard such shape data in the determination of the estimated state at block 1230.

Adjusting the shape data may also include assigning a confidence value or weight to the shape data or adjusting such confidence value or weight assigned to the shape data. For example, upon determining that the shape data satisfies one or more conditions indicated by the robotic data, the system may increase the confidence value or weight associated with the shape data. Alternatively, upon determining that the shape data does not satisfy one or more conditions indicated by the robotic data, the system may decrease the confidence value or weight associated with the shape data.

At block 1230, the system determines an estimated state of the instrument based on the adjusted shape data. In some cases, the system may determine the estimated state of the instrument based on a combination of the adjusted shape data and data from one or more data stores shown in FIG. 8A and/or one or more estimated state data from the state estimator 980 in FIG. 8A. At block 1235, the system outputs the estimated state of the instrument. The method 1200 ends at block 1240.

VII. B. Overview of Shape Data Adjustment Process

Figure 13:
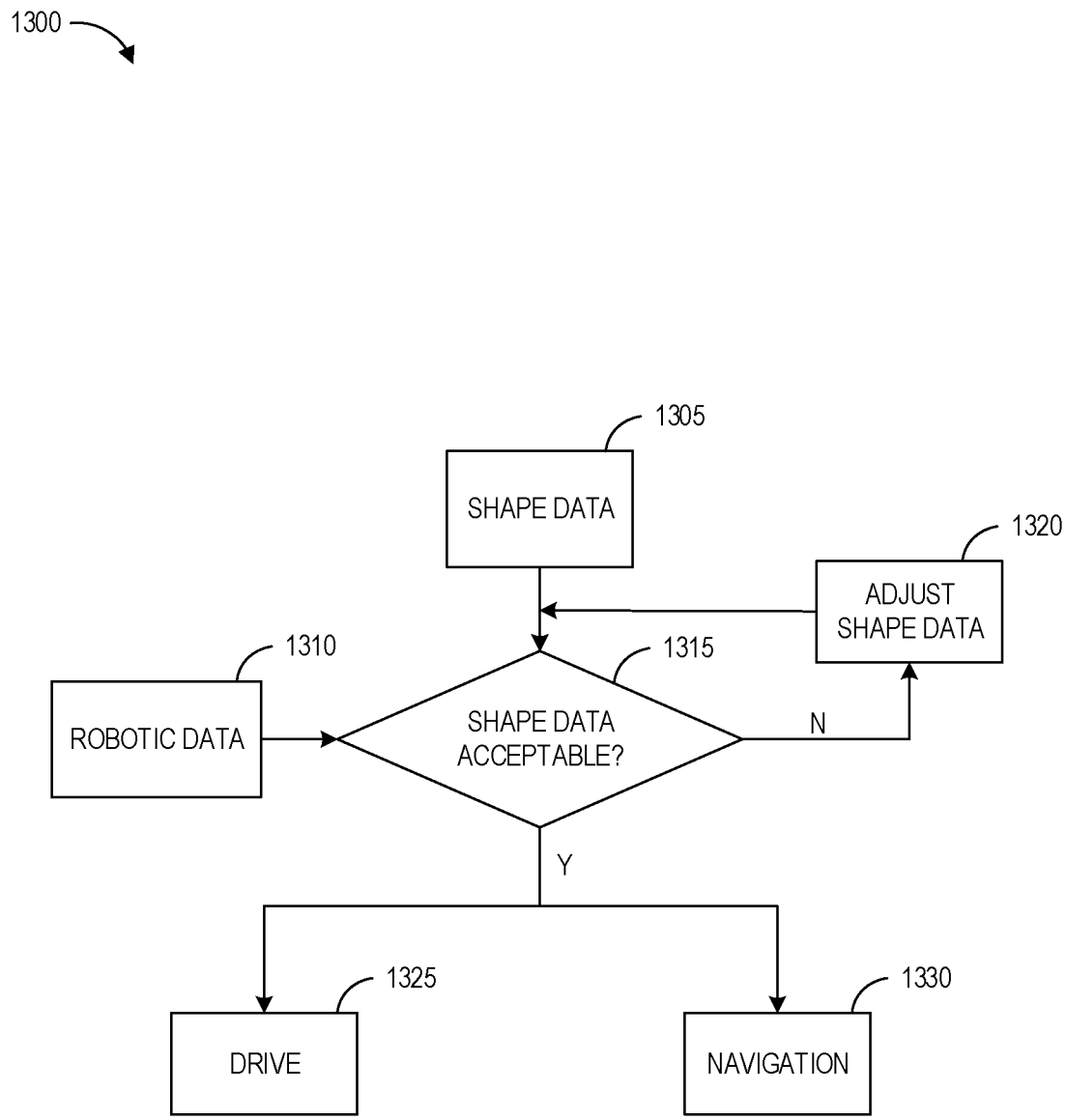
FIG. 13 shows a conceptual diagram illustrating an example method operable by a surgical robotic system, or component(s) thereof, for operating an instrument, according to one embodiment.

FIG. 13 is a conceptual diagram illustrating an example method operable by a surgical robotic system, or component(s) thereof, for operating an instrument, according to one embodiment. For example, the steps shown in diagram 1300 illustrated in FIG. 13 may be performed by processor(s) and/or other component(s) of a medical robotic system (e.g., surgical robotic system 500) or associated system(s) (e.g., the strain-based algorithm module 945 of the navigation configuration system 900). For convenience, the processes illustrated in diagram 1300 are described as performed by the surgical robotic system, also referred to simply as the "system."

As shown in FIG. 13, shape data 1305 and robotic data 1310 are fed into the decision block 1315. At block 1315, the system determines whether the shape data 1305 is acceptable in view of the robotic data 1310. Upon determining that the shape data is not acceptable, the system proceeds to block 1320 and adjusts the shape data. Upon determining that the shape data is acceptable, the system proceeds to block 1325 to drive the instrument based at least on the shape data (or adjusted shape data) and/or to block 1330 to navigate the instrument based at least on the shape data (or adjusted shape data).

VII. C. Overview of Shape Data Confidence Adjustment Process

Figure 14:
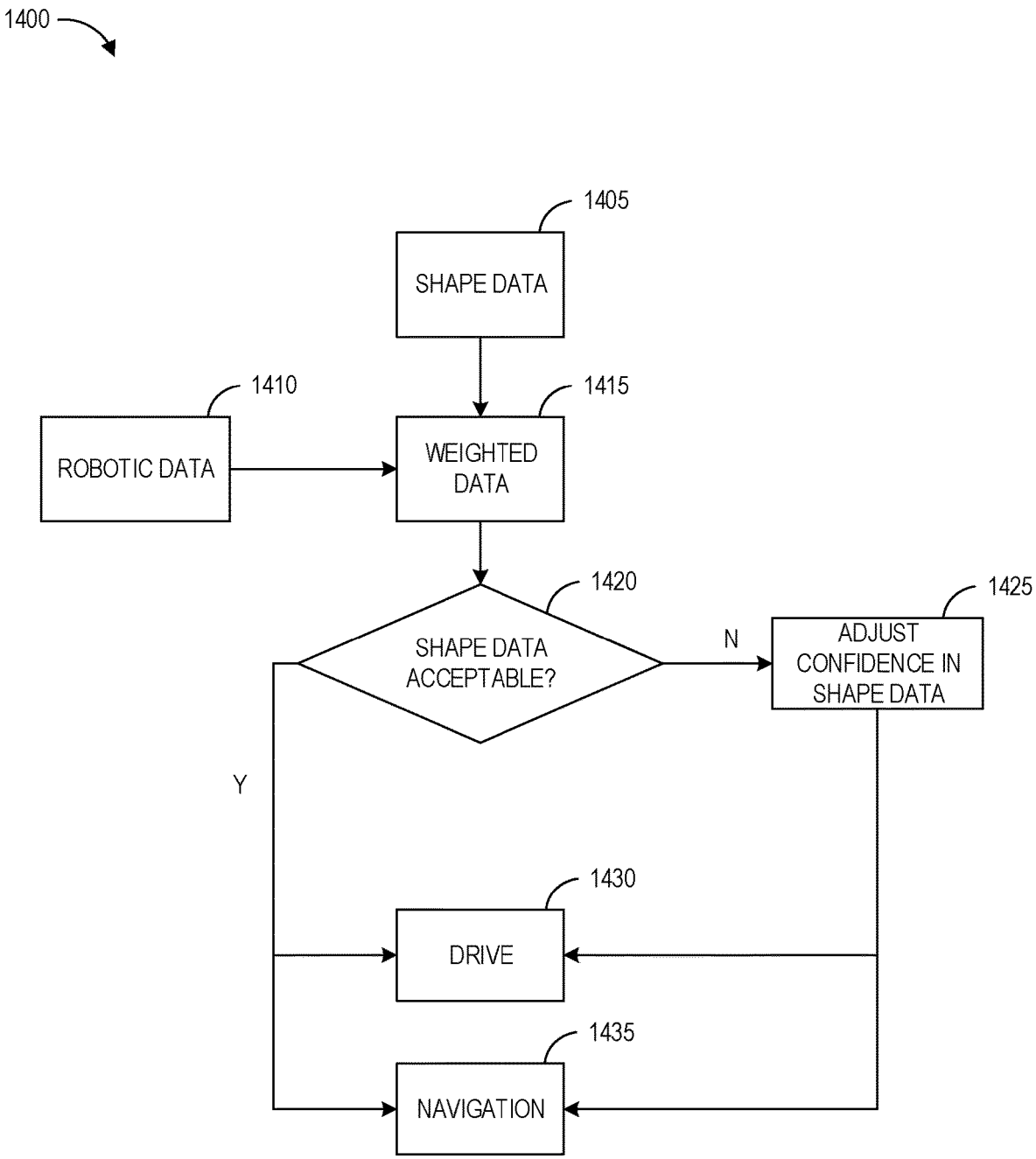
FIG. 14 shows a conceptual diagram illustrating an example method operable by a surgical robotic system, or component(s) thereof, for operating an instrument, according to one embodiment.

FIG. 14 is a conceptual diagram illustrating an example method operable by a surgical robotic system, or component(s) thereof, for operating an instrument, according to one embodiment. For example, the steps shown in diagram 1400 illustrated in FIG. 14 may be performed by processor(s) and/or other component(s) of a medical robotic system (e.g., surgical robotic system 500) or associated system(s) (e.g., the strain-based algorithm module 945 of the navigation configuration system 900). For convenience, the processes illustrated in diagram 1400 are described as performed by the surgical robotic system, also referred to simply as the "system."

As shown in FIG. 14, the system takes shape data 1405 and robotic data 1410 and generates weighted data 1415. The weighted data 1415 may be a weighted sum of the shape data 1405 and the robotic data 1410, where the shape data 1405 and the robotic data 1410 are weighted based on their respective confidence values. If the confidence value associated with the shape data 1405 is higher than that of the robotic data 1410, the shape represented by the weighted data 1415 may be closer to that represented by the shape data 1405. On the other hand, if the confidence value associated with the robotic data 1410 is higher than that of the shape data 1405, the shape represented by the weighted data 1415 may be closer to that represented by the robotic data 1410. At block 1420, the system determines whether the shape data 1405 is acceptable in view of the robotic data 1410. Upon determining that the shape data 1405 is not acceptable, the system proceeds to block 1425 and adjusts the confidence value associated with the shape data 1405. The system then proceeds to block 1430 to drive the instrument based at least on the weighted data reflecting the adjusted confidence value and/or to block 1435 to navigate the instrument based at least on the weighted data reflecting the adjusted confidence value. On the other hand, upon determining that the shape data 1405 is acceptable, the system proceeds to block 1430 to drive the instrument based at least on the weighted data 1415 and/or to block 1435 to navigate the instrument based at least on the weighted data 1415.

As just discussed with respect to FIG. 14, a number of embodiments described herein may adjust confidence values to improve navigation or the control of the medical instrument. For example, in some cases, a navigation system may use the adjusted confidence value to lower the weight given to the strain-based shape data to determine the location of the medical instrument relative to anatomy of a patient, as may be represented by a preoperative model of the patient. As discussed in other portions of this disclosure, a navigation system (see, e.g., FIG. 8A) may receive a number of different state estimates of the medical instruments from corresponding state estimators and, according to the embodiment shown in FIG. 14, the navigation system may lower the weight given to the state derived from the strain-based shape data based on the comparison. Depending on the adjusted confidence, the navigation system may disregard the state estimate derived from state estimators using the strain-based shape data or may lower the impact the state estimator has on determining the estimated state of the medical device.

It is to be appreciated that the converse is also possible for embodiments contemplated by this disclosure. That is, if the comparison between the strain-based shape data and the robotic data-based shape data determines that the two types of data closely matches (as may be determined by a threshold amount) then the navigation system may increase the confidence or weight of the state estimate derived from the strain-based shape data.

Similarly described in FIG. 14, some embodiments may include a control system that controls the drive of the medical instrument based on the comparison between the strain-based shape data and the robotic data. Such control systems may, based on the comparison, use or disregard the strain-based shape data when controlling the pose of the medical instrument.

While FIGS. 4D, 4E, and 9-14 are described herein with respect to robotic data, in other embodiments, other data can be used instead of robotic data or in combination with robotic data. Also, although some techniques described herein are described with reference to surgical robotic systems, in other embodiments, such techniques can be applied to non-surgical systems such as medical robotic systems and systems for controlling an instrument within interior regions of a body that do not involve a surgery.

VIII. Implementing Systems and Terminology

Implementations disclosed herein provide systems, methods and apparatuses for detecting physiological noise during navigation of a luminal network.

It should be noted that the terms "couple," "coupling," "coupled," or other variations of the word couple as used herein may indicate either an indirect connection or a direct connection. For example, if a first component is "coupled" to a second component, the first component may be either indirectly connected to the second component via another component or directly connected to the second component.

The functions described herein may be stored as one or more instructions on a processor-readable or computer-readable medium. The term "computer-readable medium" refers to any available medium that can be accessed by a computer or processor. By way of example, and not limitation, such a medium may comprise random access memory (RAM), read-only memory (ROM), electrically erasable programmable read-only memory (EEPROM), flash memory, compact disc read-only memory (CD-ROM) or other optical disk storage may comprise RAM, ROM, EEPROM, flash memory, CD-ROM or other optical disk storage, magnetic disk storage or other magnetic storage devices, or any other medium that can be used to store desired program code in the form of instructions or data structures and that can be accessed by a computer. It should be noted that a computer-readable medium may be tangible and non-transitory. As used herein, the term "code" may refer to software, instructions, code or data that is/are executable by a computing device or processor.

The methods disclosed herein comprise one or more steps or actions for achieving the described method. The method steps and/or actions may be interchanged with one another without departing from the scope of the claims. In other words, unless a specific order of steps or actions is required for proper operation of the method that is being described, the order and/or use of specific steps and/or actions may be modified without departing from the scope of the claims.

As used herein, the term "plurality" denotes two or more. For example, a plurality of components indicates two or more components. The term "determining" encompasses a wide variety of actions and, therefore, "determining" can include calculating, computing, processing, deriving, investigating, looking up (e.g., looking up in a table, a database or another data structure), ascertaining and the like. Also, "determining" can include receiving (e.g., receiving information), accessing (e.g., accessing data in a memory) and the like. Also, "determining" can include resolving, selecting, choosing, establishing and the like.

The phrase "based on" does not mean "based only on," unless expressly specified otherwise. In other words, the phrase "based on" describes both "based only on" and "based at least on."

The previous description of the disclosed implementations is provided to enable any person skilled in the art to make or use the present invention. Various modifications to these implementations will be readily apparent to those skilled in the art, and the generic principles defined herein may be applied to other implementations without departing from the scope of the invention. For example, it will be appreciated that one of ordinary skill in the art will be able to employ a number corresponding alternative and equivalent structural details, such as equivalent ways of fastening, mounting, coupling, or engaging tool components, equivalent mechanisms for producing particular actuation motions, and equivalent mechanisms for delivering electrical energy. Thus, the present invention is not intended to be limited to the implementations shown herein but is to be accorded the widest scope consistent with the principles and novel features disclosed herein.

What is claimed is:

1. A method of controlling an instrument, the method comprising:
    measuring strain of one or more optical fibers associated with an elongate shaft of an instrument;
    determining a first shape estimation of the elongate shaft based on the measured strain and a first weight associated therewith;
    determining, based on the measured strain, a strain-indicated characteristic of the elongate shaft with respect to a mechanical condition of the elongate shaft;
    determining an expected range of the mechanical condition of the elongate shaft;
    determining that the strain-indicated characteristic is outside of the expected range of the mechanical condition;
    in response to the determination that the strain-indicated characteristic is outside of the expected range, determining a second shape estimation of the elongate shaft based on the measured strain and a second weight associated therewith, the second weight lower than the first weight; and
    outputting the second shape estimation of the elongate shaft.

2. The method of claim 1, wherein the mechanical condition is one of curvature of the elongate shaft or speed of motion of the elongate shaft.

3. The method of claim 1, wherein the expected range of the mechanical condition is based on robotic command data used to control movement of the instrument.

4. The method of claim 3, wherein the robotic command data indicates a commanded pitch, roll, yaw, and insertion of the instrument.

5. The method of claim 1, wherein the expected range of the mechanical condition is based on at least one of:
    pull force on one or more articulation pull wires associated with the elongate shaft; or
    actuation position of the one or more articulation pull wires.

6. The method of claim 1, wherein the expected range of the mechanical condition is based on image data received from a camera associated with a distal portion of the elongate shaft.

7. The method of claim 6, further comprising determining that the image data indicates an orientation of the elongate shaft relative to an anatomical lumen, wherein said determining that the strain-indicated characteristic is outside of the expected range of the mechanical condition is based on the indicated orientation of the elongate shaft.

8. The method of claim 1, wherein said determining that the strain-indicated characteristic is outside of the expected range of the mechanical condition involves:
    determining a position of at least a portion of the elongate shaft relative to a virtual model of an anatomical lumen in which at least a portion of the elongate shaft is disposed; and determining that the position of the at least a portion of the elongate shaft is outside of a boundary of the virtual model of the anatomical lumen.

9. The method of claim 1, wherein said determining the second shape estimation of the elongate shaft involves decreasing a confidence value associated with the measured strain.

10. The method of claim 1, wherein said determining the second shape estimation of the elongate shaft involves adjusting the measured strain to bring the strain-indicated characteristic within the expected range.

11. A robotic system for controlling an instrument, the system comprising:
an interface configured to receive signals from one or more optical fibers disposed at least partially within an elongate shaft of an instrument; and
control circuitry configured to:
determine a measured strain of the one or more optical fibers based on the received signals;
determine a first shape estimation of the elongate shaft based on the measured strain and a first weight associated therewith;
determine, based on the measured strain, a strain-indicated characteristic of the elongate shaft with respect to a mechanical condition of the elongate shaft;
determine an expected range of the mechanical condition of the elongate shaft;
determine that the strain-indicated characteristic is outside of the expected range of the mechanical condition;
in response to the determination that the strain-indicated characteristic is outside of the expected range, determine a second shape estimation of the elongate shaft based on the measured strain and a second weight associated therewith, the second weight lower than the first weight; and
output the second shape estimation of the elongate shaft.

12. The robotic system of claim 11, wherein the mechanical condition is one of curvature of the elongate shaft or speed of motion of the elongate shaft.

13. The robotic system of claim 11, wherein the expected range of the mechanical condition is based on robotic command data that indicates at least one of a commanded pitch, roll, yaw, or insertion of the instrument.

14. The robotic system of claim 11, wherein the expected range of the mechanical condition is based on at least one of:
pull force on one or more articulation pull wires associated with the elongate shaft; or
actuation position of the one or more articulation pull wires.

15. The robotic system of claim 11, wherein:
the expected range of the mechanical condition is based on image data received from a camera associated with a distal portion of the elongate shaft;
the control circuitry is further configured to determine that the image data indicates an orientation of the elongate shaft relative to an anatomical lumen; and
said determining that the strain-indicated characteristic is outside of the expected range of the mechanical condition is based on the indicated orientation of the elongate shaft.

16. The robotic system of claim 11, wherein said determining that the strain-indicated characteristic is outside of the expected range of the mechanical condition involves:
determining a position of at least a portion of the elongate shaft relative to a virtual model of an anatomical lumen in which at least a portion of the elongate shaft is disposed; and
determining that the position of the at least a portion of the elongate shaft is outside of a boundary of the virtual model of the anatomical lumen.

17. The robotic system of claim 11, wherein said determining the second shape estimation of the elongate shaft involves adjusting the measured strain to bring the strain-indicated characteristic within the expected range.

18. A non-transitory computer-readable storage medium having stored thereon instructions that, when executed, cause one or more processors of a device to at least:
measure strain of one or more optical fibers associated with an elongate shaft of an instrument;
determine a first shape estimation of the elongate shaft based on the measured strain and a first weight associated therewith;
determine, based on the measured strain, a strain-indicated characteristic of the elongate shaft with respect to a mechanical condition of the elongate shaft;
determine an expected range of the mechanical condition of the elongate shaft;
determine that the strain-indicated characteristic is outside of the expected range of the mechanical condition;
in response to the determination that the strain-indicated characteristic is outside of the expected range, determining a second shape estimation of the elongate shaft based on the measured strain and a second weight associated therewith, the second weight lower than the first weight; and
output the second shape estimation of the elongate shaft.

19. The non-transitory computer-readable storage medium of claim 18, wherein the expected range of the mechanical condition is based on at least one of:
pull force on one or more articulation pull wires associated with the elongate shaft; or
actuation position of the one or more articulation pull wires.

20. The non-transitory computer-readable storage medium of claim 18, wherein said determining the second shape estimation of the elongate shaft involves adjusting the measured strain to bring the strain-indicated characteristic within the expected range.

* * * * *